United States Patent
Li et al.

(10) Patent No.: US 10,254,291 B2
(45) Date of Patent: Apr. 9, 2019

(54) QUATERNARY AMMONIUM CONTAINING ISOBARIC TAG FOR QUANTITATIVE GLYCAN PROFILING

(71) Applicant: University of Maryland, College Park, College Park, MD (US)

(72) Inventors: Shuwei Li, Clarksburg, MD (US); Hui Zhang, Ellicott City, MD (US); Shuang Yang, Ellicott City, MD (US)

(73) Assignees: UNIVERSITY OF MARYLAND, COLLEGE PARK, College Park, MD (US); THE JOHNS HOPKINS UNIVERSITY, Baltimore, MD (US)

( * ) Notice: Subject to any disclaimer, the term of this patent is extended or adjusted under 35 U.S.C. 154(b) by 371 days.

(21) Appl. No.: 14/880,972

(22) Filed: Oct. 12, 2015

(65) Prior Publication Data

US 2016/0252518 A1    Sep. 1, 2016

Related U.S. Application Data

(60) Provisional application No. 62/063,111, filed on Oct. 13, 2014, provisional application No. 62/239,576, filed on Oct. 9, 2015.

(51) Int. Cl.
*G01N 33/68* (2006.01)

(52) U.S. Cl.
CPC ..... *G01N 33/6848* (2013.01); *G01N 2458/15* (2013.01); *G01N 2560/00* (2013.01)

(58) Field of Classification Search
None
See application file for complete search history.

(56) References Cited

U.S. PATENT DOCUMENTS 8,486,712 B2    7/2013  Li et al.
2015/0241437 A1    8/2015  Zhang et al.

OTHER PUBLICATIONS

"Amines," IUPAC. Compendium of Chemical Terminology, 2nd ed. (the "Gold Book"). Compiled by A. D. McNaught and A. Wilkinson. Blackwell Scientific Publications, Oxford (1997).*
"Quaternary ammonium compounds," IUPAC. Compendium of Chemical Terminology, 2nd ed. (the "Gold Book"). Compiled by A. D. McNaught and A. Wilkinson. Blackwell Scientific Publications, Oxford (1997).*
"Isotopes," IUPAC. Compendium of Chemical Terminology, 2nd ed. (the "Gold Book"). Compiled by A. D. McNaught and A. Wilkinson. Blackwell Scientific Publications, Oxford (1997).*
Aldredge, D., et al., "Annotation of a Serum N-Glycan Library for Rapid Identification of Structures", "J. Proteome Res.", Feb. 9, 2012, pp. 1958-1968, vol. 11.

(Continued)

*Primary Examiner* — Christopher Adam Hixson
*Assistant Examiner* — Michelle Adams
(74) *Attorney, Agent, or Firm* — Hultquist, PLLC; Steven J. Hultquist

(57) ABSTRACT

The disclosure provides quaternary ammonium containing isobaric tag reagents useful in the analysis of biomolecules and methods of making and using the quaternary ammonium containing isobaric tag reagents. The quaternary ammonium containing isobaric tag reagents are particularly useful for glycan analysis, especially quantitative glycan profiling such as glycan quantitation by tandem mass spectrometry.

20 Claims, 23 Drawing Sheets

| Tag | 1 | 2 | 3 | 4 |
|-----|---|---|---|---|
| 176 | CH₃ | CH₃ | C | ¹³CHD₂ |
| 177 | CH₃ | CH₃ | ¹³C | CHD₂ |
| 178 | ¹³CH₃ | ¹³CH₃ | C | ¹³CH₃ |
| 179 | ¹³CH₃ | ¹³CH₃ | ¹³C | CH₃ |

(56) References Cited

OTHER PUBLICATIONS

Alvarez-Manilla, G., et al., "Tools for glycomics: relative quantitation of glycans by isotopic permethylation using 13CH3I", "Glycobiology", Mar. 23, 2007, pp. 677-687, vol. 17, No. 7.
Bigge, J., et al., "Nonselective and Efficient Fluorescent Labeling of Glycans Using 2-Amino Benzamide and Anthranilic Acid", "Analytical Biochemistry", Sep. 20, 1995, pp. 229-238, vol. 230.
Bork, K., et al., "Increasing the Sialylation of Therapeutic Glycoproteins: The Potential of the Sialic Acid Biosynthetic Pathway", "Journal of Pharmaceutical Sciences", Feb. 6, 2009, pp. 3499-3508, vol. 98, No. 10.
Bowman, M., et al., "Novel Tags for the Stable Isotopic Labeling of Carbohydrates and Quantitative Analysis by Mass Spectrometry", "Anal Chem.", Jul. 3, 2007, pp. 5777-5784, vol. 79.
Bragonzi, A., et al., "A new Chinese hamster ovary cell line expressing alpha2,6-sialyltransferase used as universal host for the production of human-like sialylated recombinant glycoproteins", "Biochimica et Biophysica Acta", May 1, 2000, pp. 273-282, vol. 1474.
Cai, Y., et al., "Facile approach to 2-acetamido-2-deoxy-beta-D-glucopyranosides via a furanosyl oxazoline", "Organic Letters", Sep. 1, 2005, pp. 4021-4024, vol. 7, No. 18.
Ceroni, A., et al., "GlycoWorkbench: A Tool for the Computer-Assisted Annotation of Mass Spectra of Glycans", "Journal of Proteome Research", Mar. 1, 2008, pp. 1650-1659, vol. 7.
Chen, Z., et al., "Comparative Evaluation of Two Isobaric Labeling Tags, DiART and iTRAQ", "Analytical chemistry", Feb. 29, 2012, pp. 2908-2915, vol. 84.
Dennis, J., et al., "Metabolism, Cell Surface Organization, and Disease", "Cell", Dec. 24, 2009, pp. 1229-1241, vol. 139.
Dove, A., "The bittersweet promise of glycobiology", "Nature Biotechnology", Oct. 19, 2001, pp. 913-917, vol. 19.
Egrie, J., et al., "Darbepoetin alfa has a longer circulating half-life and greater in vivo potency than recombinant human erythropoietin", "Experimental Hematology", Apr. 2003, pp. 290-299, vol. 31.
Hahne, H., et al., "Carbonyl-Reactive Tandem Mass Tags for the Proteome-Wide Quantification of N-Linked Glycans", "Analytical Chemistry", Mar. 28, 2012, pp. 3716-3724, vol. 84.
Kang, P., et al., "High-throughput solid-phase permethylation of glycans prior to mass spectrometry", "Rapid Communications in Mass Spectrometry", Feb. 11, 2008, pp. 721-734, vol. 22.
Kang, P., et al., "Solid-phase permethylation of glycans for mass spectrometric analysis", "Rapid Communications in Mass Spectrometry", Oct. 27, 2005, pp. 3421-3428, vol. 19.
Kita, Y., et al., "Quantitative Glycomics of Human Whole Serum Glycoproteins Based on the Standardized Protocol for Liberating N-Glycans", "Molecular & Cellular Proteomics", May 23, 2007, pp. 1437-1445, vol. 6.
Marino, K, et al., "A systematic approach to protein glycosylation analysis: a path through the maze", "Nature Chemical Biology", Sep. 17, 2010, pp. 713-723, vol. 6.
McAlister, G., et al., "Increasing the Multiplexing Capacity of TMTs Using Reporter Ion Isotopologues with Isobaric Masses", "Analytical Chemistry", Aug. 2, 2012, pp. 7469-7478, vol. 84.

Miura Y., et al., "BlotGlycoABCTM, an integrated glycoblotting technique for rapid and large scale clinical glycomics", "Molecular & Cellular Proteomics", Nov. 5, 2007, pp. 370-377, vol. 7.
Morell, A., et al., "The Role of Sialic Acid in Determining the Survival of Glycoproteins in the Circulation", "The Journal of Biological Chemistry", Mar. 10, 1971, pp. 1461-1467, vol. 246, No. 5.
Prien, J., et al., "Mass Spectrometric-Based Stable Isotopic 2-Aminobenzoic Acid Glycan Mapping for Rapid Glycan Screening of Biotherapeutics", "Analytical Chemistry", Feb. 15, 2010, pp. 1498-1508, vol. 82.
Rask-Andersen, M., et al., "The Druggable Genome: Evaluation of Drug Targets in Clinical Trials Suggests Major Shifts in Molecular Class and Indication", "Annu. Rev. Pharmacol. Toxicol.", Aug. 30, 2013, pp. 9-26, vol. 54.
Ruhaak, L., et al., "Glycan labeling strategies and their use in identification and quantification", "Anal Bioanal Chem", Aug. 2010, pp. 3457-3481, vol. 397.
Shah, P., et al., "Mass Spectrometric Analysis of Sialylated Glycans with Use of Solid-Phase Labeling of Sialic Acids", "Analytical Chemistry", Feb. 27, 2013, pp. 3606-3613, vol. 85.
Stumpo, K., et al., "The N-Glycome of Human Plasma", "Journal of Proteome Research", Jul. 23, 2010, pp. 4823-4830, vol. 9.
Walsh, G., et al., "Post-translational modifications in the context of therapeutic proteins", "Nature Biotechnology", Oct. 2006, pp. 1241-1252, vol. 24, No. 10.
Yang, S., et al., "Glycomic Analysis Using Glycoprotein Immobilization for Glycan Extraction", "Analytical Chemistry", pp. 5555-5561, vol. 85, 2013.
Yang, S., et al., "The Use of QABIT-ESI-HPLC-MS/MS for Quantitation of Tissue Sialylation in a Mouse Model of GNE Myopathy", Oct. 10-14, 2014, p. 1 Publisher: Poster Presentation, 30th Asilomar Conference on Mass Spectrometry Advances in Glycomics and Glycoproteomics: Methods and Applications.
Yang, S., et al., "Glycan Analysis by Reversible Reaction to Hydrazide Beads and Mass Spectrometry", "Analytical Chemistry", Jan. 25, 2012, pp. 2232-2238, vol. 84.
Yang, S., et al., "Glycan Analysis by Isobaric Aldehyde Reactive Tags and Mass Spectrometry", "Analytical Chemistry", Sep. 3, 2013, pp. 8188-8195, vol. 85.
Yuan, W., et al., "Subsecond Absolute Quantitation of Amine Metabolites Using Isobaric Tags for Discovery of Pathway Activation in Mammalian Cells", "Analytical Chemistry", Feb. 21, 2012, pp. 2892-2899, vol. 84.
Yuan, W., et al., "Amine Metabolomics of Hyperglycemic Endothelial Cells using Capillary LC-MS with Isobaric Tagging", "J. Proteome Res.", Oct. 3, 2011, pp. 5242-5250, vol. 10.
Zambrowicz, B., et al., "Knockouts model the 100 best-selling drugs—will they model the next 100?", "Nature Reviews Drug Discovery", Jan. 2003, pp. 38-51, vol. 2.
Zeng, D., et al., "Revival of deuterium-labeled reagents for protein quantitation", "Chem. Commun. (Camb)", May 19, 2009, pp. 3369-3371.
Zhang, J., et al., "Deuterium Isobaric Amine-Reactive Tags for Quantitative Proteomics", "Analytical Chemistry", Sep. 15, 2010, pp. 7588-7595, vol. 82, No. 18.

\* cited by examiner

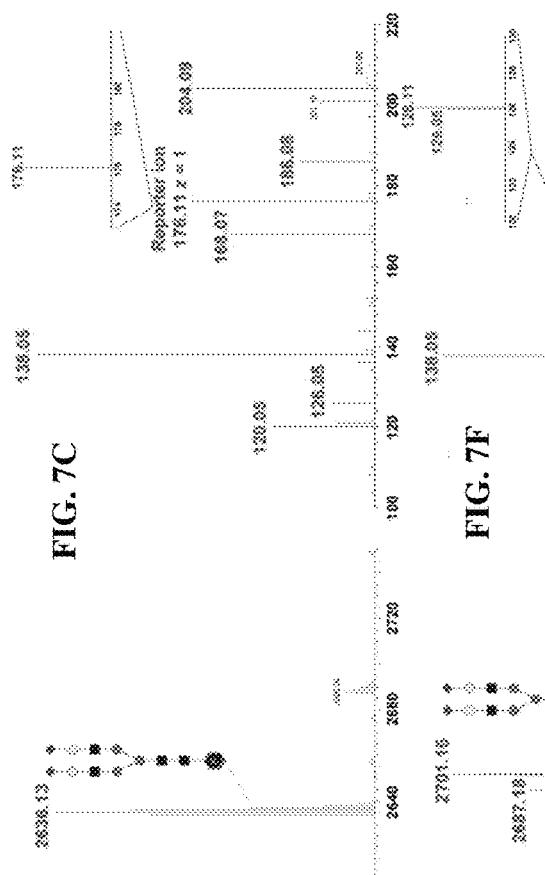
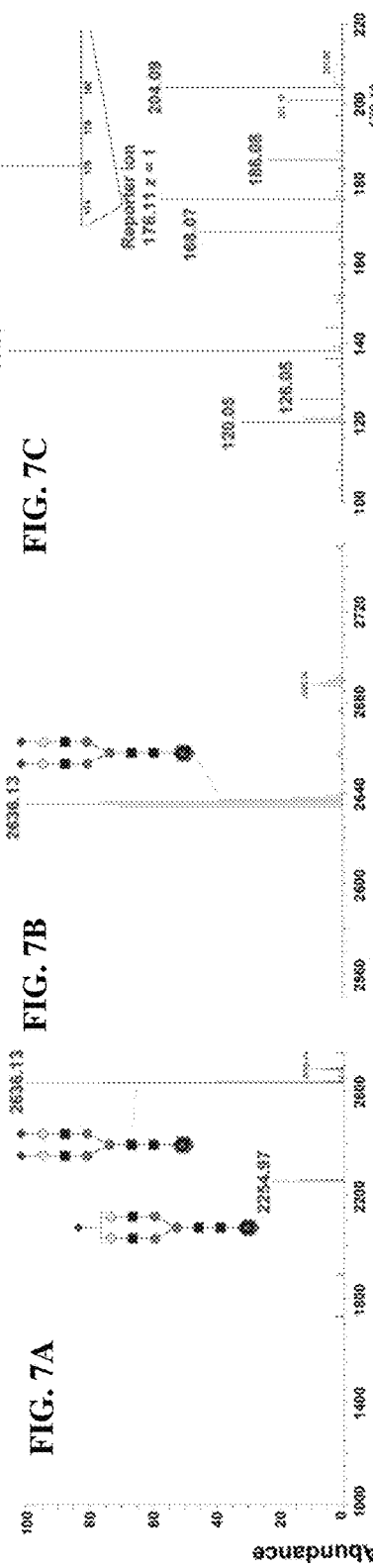
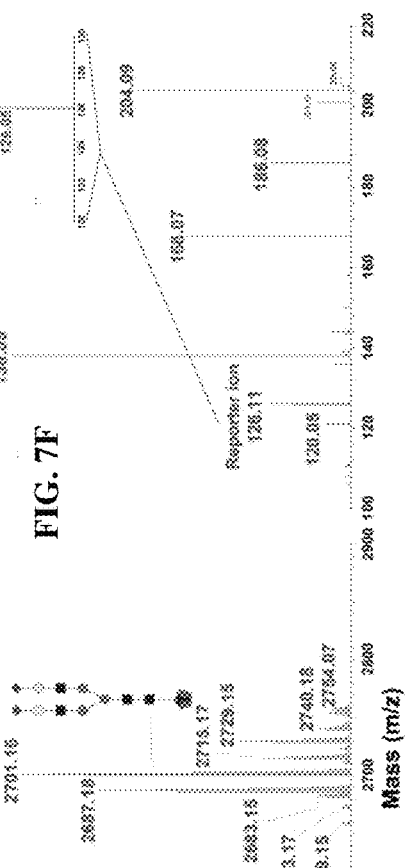
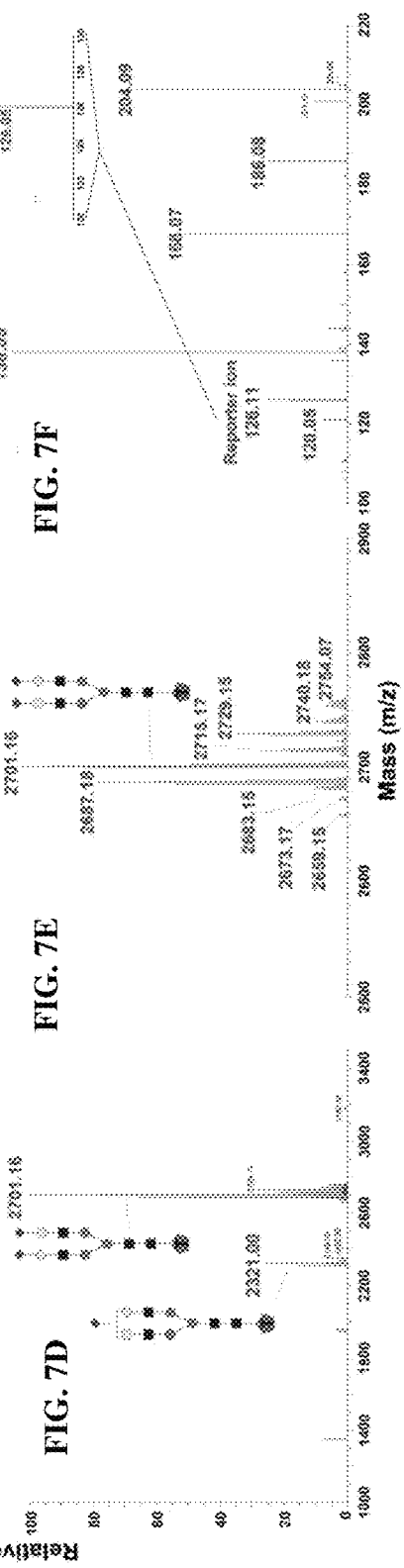
FIG. 7A  FIG. 7B  FIG. 7C
FIG. 7D  FIG. 7E  FIG. 7F

FIG. 11A

| List | Symbol | F a | N b | H c | S d | G | G-pT | M | WT | ST6Gal1 (+) | ST3Gal4 (-) |
|---|---|---|---|---|---|---|---|---|---|---|---|
| 1 | H$_2$ | 0 | 0 | 2 | 0 | 1257.4 | 1257.4 | 1468.7 | 0.00E+00 | 0.00E+00 | 0.00E+00 |
| 2 | FN | 1 | 1 | 0 | 0 | 1282.5 | 1282.5 | 1493.7 | 1.86E-03 | 4.74E-03 | 4.48E-03 |
| 3 | NH | 0 | 1 | 1 | 0 | 1298.5 | 1298.5 | 1509.7 | 1.36E-03 | 1.90E-02 | 3.39E-03 |
| 4 | F$_2$H | 2 | 0 | 1 | 0 | 1387.5 | 1387.5 | 1598.7 | 0.00E+00 | 0.00E+00 | 0.00E+00 |
| 5 | H$_3$ | 0 | 0 | 3 | 0 | 1419.5 | 1419.5 | 1630.7 | 0.00E+00 | 0.00E+00 | 0.00E+00 |
| 6 | FNH | 1 | 1 | 1 | 0 | 1444.5 | 1444.5 | 1655.8 | 2.97E-03 | 3.84E-03 | 3.25E-03 |
| 7 | N$_2$H | 0 | 2 | 1 | 0 | 1501.6 | 1501.6 | 1712.8 | 0.00E+00 | 1.32E-02 | 0.00E+00 |
| 8 | NS | 0 | 1 | 0 | 1 | 1449.5 | 1516.6 | 1727.8 | 1.24E-02 | 0.00E+00 | 8.38E-03 |
| 9 | F$_3$H | 3 | 0 | 1 | 0 | 1533.6 | 1533.6 | 1744.8 | 0.00E+00 | 3.97E-02 | 0.00E+00 |
| 10 | FH$_3$ | 1 | 0 | 3 | 0 | 1565.5 | 1565.5 | 1776.8 | 1.80E-03 | 0.00E+00 | 0.00E+00 |
| 11 | H$_4$ | 0 | 0 | 4 | 0 | 1581.5 | 1581.5 | 1792.8 | 0.00E+00 | 7.62E-03 | 0.00E+00 |
| 12 | FNH$_2$ | 1 | 1 | 2 | 0 | 1606.6 | 1606.6 | 1817.8 | 0.00E+00 | 1.03E-02 | 0.00E+00 |
| 13 | FHS | 1 | 0 | 1 | 1 | 1554.5 | 1621.6 | 1832.9 | 0.00E+00 | 9.99E-03 | 0.00E+00 |
| 14 | FN$_2$H | 1 | 2 | 1 | 0 | 1647.6 | 1647.6 | 1858.9 | 0.00E+00 | 1.90E-02 | 0.00E+00 |
| 15 | FNS | 1 | 1 | 0 | 1 | 1595.6 | 1662.7 | 1873.9 | 6.40E-02 | 1.08E-02 | 4.22E-02 |
| 16 | N$_2$H$_2$ | 0 | 2 | 2 | 0 | 1663.6 | 1663.6 | 1874.9 | 1.12E-02 | 1.34E-02 | 1.07E-02 |
| 17 | NHS | 0 | 1 | 1 | 1 | 1611.6 | 1678.7 | 1889.9 | 9.90E-03 | 4.54E-02 | 5.31E-03 |
| 18 | FN$_3$ | 1 | 3 | 0 | 0 | 1688.7 | 1688.7 | 1899.9 | 0.00E+00 | 0.00E+00 | 0.00E+00 |
| 19 | N$_3$H | 0 | 3 | 1 | 0 | 1704.7 | 1704.7 | 1915.9 | 0.00E+00 | 5.40E-03 | 1.54E-02 |
| 20 | FN$_2$H$_2$ | 1 | 2 | 2 | 0 | 1809.7 | 1809.7 | 2020.9 | 1.40E-02 | 4.73E-03 | 2.15E-02 |
| 21 | FNHS | 1 | 1 | 1 | 1 | 1757.6 | 1824.7 | 2035.9 | 9.48E-03 | 1.54E-02 | 7.28E-03 |
| 22 | NH$_2$S | 0 | 1 | 2 | 1 | 1773.6 | 1840.7 | 2051.9 | 1.68E-03 | 2.41E-02 | 1.83E-03 |
| 23 | N$_2$HS | 0 | 2 | 1 | 1 | 1814.7 | 1881.8 | 2093.0 | 6.63E-03 | 1.90E-02 | 3.56E-03 |
| 24 | FNH$_2$S | 1 | 1 | 2 | 1 | 1919.7 | 1986.8 | 2198.0 | 9.23E-03 | 1.70E-02 | 1.01E-02 |
| 25 | NH$_3$S | 0 | 1 | 3 | 1 | 1935.7 | 2002.8 | 2214.0 | 0.00E+00 | 0.00E+00 | 0.00E+00 |
| 26 | FN$_2$HS | 1 | 2 | 1 | 1 | 1960.7 | 2027.8 | 2239.0 | 9.06E-03 | 9.61E-03 | 7.02E-03 |
| 27 | N$_3$H$_3$ | 0 | 3 | 3 | 0 | 2028.8 | 2028.8 | 2240.0 | 1.39E-03 | 1.00E-02 | 1.30E-03 |
| 28 | N$_2$H$_2$S | 0 | 2 | 2 | 1 | 1976.7 | 2043.8 | 2255.0 | 9.15E-03 | 6.30E-02 | 9.39E-03 |
| 29 | FN$_4$H | 1 | 4 | 1 | 0 | 2053.8 | 2053.8 | 2265.1 | 0.00E+00 | 0.00E+00 | 0.00E+00 |
| 30 | NHS$_2$ | 0 | 1 | 1 | 2 | 1924.7 | 2058.8 | 2270.1 | 0.00E+00 | 4.40E-02 | 0.00E+00 |
| 31 | F$_3$NH$_3$ | 3 | 1 | 3 | 0 | 2060.8 | 2060.8 | 2272.0 | 0.00E+00 | 1.82E-02 | 0.00E+00 |
| 32 | H$_7$ | 0 | 0 | 7 | 0 | 2067.7 | 2067.7 | 2278.9 | 1.98E-03 | 0.00E+00 | 3.68E-03 |
| 33 | N$_3$HS | 0 | 3 | 1 | 1 | 2017.8 | 2084.8 | 2296.1 | 0.00E+00 | 1.02E-02 | 0.00E+00 |
| 34 | FN$_5$ | 1 | 5 | 0 | 0 | 2094.9 | 2094.9 | 2306.1 | 1.11E-02 | 1.19E-02 | 8.47E-03 |
| 35 | N$_5$H | 0 | 5 | 1 | 0 | 2110.9 | 2110.9 | 2322.1 | 8.93E-04 | 5.48E-02 | 4.57E-03 |
| 36 | F$_3$NHS | 3 | 1 | 1 | 1 | 2049.7 | 2116.8 | 2328.1 | 0.00E+00 | 0.00E+00 | 0.00E+00 |
| 37 | F$_2$N$_2$HS | 2 | 2 | 1 | 1 | 2106.8 | 2173.9 | 2385.1 | 0.00E+00 | 4.34E-03 | 0.00E+00 |
| 38 | FN$_2$H$_2$S | 1 | 2 | 2 | 1 | 2122.8 | 2189.9 | 2401.1 | 2.86E-02 | 5.53E-02 | 3.01E-02 |
| 39 | FNHS$_2$ | 1 | 1 | 1 | 2 | 2070.7 | 2204.9 | 2416.1 | 0.00E+00 | 3.21E-02 | 1.67E-03 |
| 40 | N$_2$H$_3$S | 0 | 2 | 3 | 1 | 2138.8 | 2205.9 | 2417.1 | 0.00E+00 | 2.64E-02 | 0.00E+00 |
| 41 | FN$_3$HS | 1 | 3 | 1 | 1 | 2163.8 | 2230.9 | 2442.1 | 2.06E-03 | 0.00E+00 | 0.00E+00 |
| 42 | F$_2$N$_5$ | 2 | 5 | 0 | 0 | 2240.9 | 2240.9 | 2452.2 | 1.80E-02 | 1.49E-02 | 2.30E-02 |
| 43 | FN$_5$H | 1 | 5 | 1 | 0 | 2256.9 | 2256.9 | 2468.1 | 0.00E+00 | 4.33E-02 | 0.00E+00 |
| 44 | FN$_3$H$_4$ | 1 | 3 | 4 | 0 | 2336.9 | 2336.9 | 2548.1 | 0.00E+00 | 2.47E-02 | 0.00E+00 |

FIG. 11B

| # | Formula | F | N | H | S | Col1 | Col2 | Col3 | Col4 | Col5 | Col6 |
|---|---|---|---|---|---|---|---|---|---|---|---|
| 45 | $FN_3H_2S$ | 1 | 3 | 2 | 1 | 2325.9 | 2393.0 | 2604.2 | 0.00E+00 | 4.52E-03 | 0.00E+00 |
| 46 | $N_3H_3S$ | 0 | 3 | 3 | 1 | 2341.9 | 2409.0 | 2620.2 | 1.96E-03 | 9.62E-03 | 1.05E-03 |
| 47 | $N_2H_2S_2$ | 0 | 2 | 2 | 2 | 2289.8 | 2424.0 | 2635.2 | 1.80E-02 | 5.37E-02 | 1.35E-02 |
| 48 | $F_2N_6$ | 2 | 6 | 0 | 0 | 2444.0 | 2444.0 | 2655.2 | 0.00E+00 | 1.66E-02 | 0.00E+00 |
| 49 | $FN_6H$ | 1 | 6 | 1 | 0 | 2460.0 | 2460.0 | 2671.2 | 0.00E+00 | 6.19E-03 | 0.00E+00 |
| 50 | $N_3HS_2$ | 0 | 3 | 1 | 2 | 2330.9 | 2465.0 | 2676.3 | 1.63E-02 | 0.00E+00 | 1.48E-02 |
| 51 | $N_6H_2$ | 0 | 6 | 2 | 0 | 2476.0 | 2476.0 | 2687.2 | 2.11E-02 | 6.01E-02 | 1.80E-02 |
| 52 | $F_2N_3H_4$ | 2 | 3 | 4 | 0 | 2482.9 | 2482.9 | 2694.2 | 0.00E+00 | 0.00E+00 | 0.00E+00 |
| 53 | $F_4N_4H$ | 4 | 4 | 1 | 0 | 2492.0 | 2492.0 | 2703.2 | 1.36E-03 | 2.66E-02 | 4.26E-03 |
| 54 | $F_2N_2H_3S$ | 2 | 2 | 3 | 1 | 2430.9 | 2498.0 | 2709.2 | 0.00E+00 | 3.44E-03 | 0.00E+00 |
| 55 | $FN_7$ | 1 | 7 | 0 | 0 | 2501.1 | 2501.1 | 2712.3 | 0.00E+00 | 4.80E-03 | 0.00E+00 |
| 56 | $F_3N_4H_2$ | 3 | 4 | 2 | 0 | 2508.0 | 2508.0 | 2719.2 | 0.00E+00 | 2.03E-02 | 0.00E+00 |
| 57 | $FN_4H_4$ | 1 | 4 | 4 | 0 | 2540.0 | 2540.0 | 2751.2 | 0.00E+00 | 2.71E-02 | 0.00E+00 |
| 58 | $FN_3H_3S$ | 1 | 3 | 3 | 1 | 2487.9 | 2555.0 | 2766.2 | 0.00E+00 | 9.83E-03 | 0.00E+00 |
| 59 | $N_4H_5$ | 0 | 4 | 5 | 0 | 2556.0 | 2556.0 | 2767.2 | 2.37E-03 | 7.13E-03 | 3.63E-03 |
| 60 | $FN_2H_2S_2$ | 1 | 2 | 2 | 2 | 2435.9 | 2570.0 | 2781.3 | 4.51E-02 | 1.15E-01 | 3.65E-02 |
| 61 | $N_3H_4S$ | 0 | 3 | 4 | 1 | 2503.9 | 2571.0 | 2782.2 | 1.77E-03 | 1.62E-02 | 1.81E-03 |
| 62 | $F_4N_2H_4$ | 4 | 2 | 4 | 0 | 2572.0 | 2572.0 | 2783.2 | 2.35E-03 | 9.12E-03 | 1.61E-03 |
| 63 | $N_2H_3S_2$ | 0 | 2 | 3 | 2 | 2451.9 | 2586.0 | 2797.3 | 8.77E-03 | 3.60E-02 | 9.26E-03 |
| 64 | $F_3N_2H_5$ | 3 | 2 | 5 | 0 | 2588.0 | 2588.0 | 2799.2 | 0.00E+00 | 0.00E+00 | 0.00E+00 |
| 65 | $FN_4H_2S$ | 1 | 4 | 2 | 1 | 2529.0 | 2596.1 | 2807.3 | 1.01E-02 | 7.42E-02 | 1.55E-02 |
| 66 | $N_4H_3S$ | 0 | 4 | 3 | 1 | 2545.0 | 2612.0 | 2823.3 | 1.53E-03 | 1.17E-02 | 5.56E-03 |
| 67 | $FN_6H_2$ | 1 | 6 | 2 | 0 | 2622.1 | 2622.1 | 2833.3 | 4.80E-02 | 5.04E-03 | 4.27E-02 |
| 68 | $N_3H_2S_2$ | 0 | 3 | 2 | 2 | 2492.9 | 2627.1 | 2838.3 | 1.66E-03 | 1.45E-02 | 6.11E-03 |
| 69 | $N_3H_3S_2$ | 0 | 3 | 3 | 2 | 2655.0 | 2789.1 | 3000.4 | 1.07E-03 | 0.00E+00 | 5.84E-03 |
| 70 | $FN_6HS$ | 1 | 6 | 1 | 1 | 2773.1 | 2840.2 | 3051.4 | 9.83E-03 | 2.79E-02 | 1.31E-02 |
| 71 | $F_3N_5H_3$ | 3 | 5 | 3 | 0 | 2873.1 | 2873.1 | 3084.4 | 6.32E-04 | 3.29E-02 | 5.95E-03 |
| 72 | $F_2N_2H_3S_2$ | 2 | 2 | 3 | 2 | 2744.0 | 2878.2 | 3089.4 | 0.00E+00 | 0.00E+00 | 0.00E+00 |
| 73 | $FN_3H_3S_2$ | 1 | 3 | 3 | 2 | 2801.0 | 2935.2 | 3146.4 | 2.84E-03 | 5.71E-03 | 4.87E-03 |
| 74 | $N_4H_5S$ | 0 | 4 | 5 | 1 | 2869.1 | 2936.2 | 3147.4 | 6.35E-04 | 5.95E-03 | 1.63E-03 |
| 75 | $FN_2H_2S_3$ | 1 | 2 | 2 | 3 | 2749.0 | 2950.2 | 3161.5 | 9.15E-04 | 6.79E-03 | 0.00E+00 |
| 76 | $FN_4H_2S_2$ | 1 | 4 | 2 | 2 | 2842.1 | 2976.2 | 3187.5 | 1.15E-03 | 1.28E-03 | 8.06E-03 |
| 77 | $F_4N_4H_4$ | 4 | 4 | 4 | 0 | 2978.2 | 2978.2 | 3189.4 | 0.00E+00 | 0.00E+00 | 0.00E+00 |
| 78 | $N_4H_3S_2$ | 0 | 4 | 3 | 2 | 2858.1 | 2992.2 | 3203.5 | 7.83E-03 | 1.54E-02 | 1.47E-02 |
| 79 | $F_2N_6H_2S$ | 2 | 6 | 2 | 1 | 3081.2 | 3148.3 | 3359.5 | 0.00E+00 | 5.81E-03 | 0.00E+00 |
| 80 | $N_3H_3S_3$ | 0 | 3 | 3 | 3 | 2968.1 | 3169.3 | 3380.5 | 5.55E-03 | 5.92E-03 | 6.76E-03 |
| 81 | $N_4H_2S_3$ | 0 | 4 | 2 | 3 | 3009.1 | 3210.4 | 3421.6 | 8.92E-03 | 8.17E-03 | 1.10E-02 |
| 82 | $F_3N_4H_4S$ | 3 | 4 | 4 | 1 | 3145.2 | 3212.3 | 3423.5 | 0.00E+00 | 0.00E+00 | 0.00E+00 |
| 83 | $N_7H_3S$ | 0 | 7 | 3 | 1 | 3154.2 | 3221.3 | 3432.6 | 6.38E-03 | 1.71E-02 | 9.78E-03 |
| 84 | $F_4N_6H_3$ | 4 | 6 | 3 | 0 | 3222.3 | 3222.3 | 3433.5 | 8.97E-03 | 1.12E-02 | 1.04E-02 |
| 85 | $F_3N_2H_2S_3$ | 3 | 2 | 2 | 3 | 3041.1 | 3242.3 | 3453.6 | 8.65E-03 | 6.45E-03 | 8.55E-03 |
| 86 | $F_4N_6HS$ | 4 | 6 | 1 | 1 | 3211.3 | 3278.4 | 3489.6 | 5.96E-03 | 1.18E-02 | 8.96E-03 |
| 87 | $F_3N_7H_3$ | 3 | 7 | 3 | 0 | 3279.3 | 3279.3 | 3490.6 | 3.75E-03 | 1.01E-02 | 6.60E-03 |
| 88 | $FN_3H_3S_3$ | 1 | 3 | 3 | 3 | 3114.1 | 3315.4 | 3526.6 | 1.58E-02 | 9.00E-03 | 1.69E-02 |
| 89 | $FN_5H_3S_2$ | 1 | 5 | 3 | 2 | 3207.2 | 3341.4 | 3552.6 | 9.34E-03 | 4.43E-03 | 1.22E-02 |
| 90 | $F_4N_5H_5$ | 4 | 5 | 5 | 0 | 3343.3 | 3343.3 | 3554.5 | 7.18E-03 | 1.47E-02 | 5.28E-03 |
| 91 | $FN_4H_2S_3$ | 1 | 4 | 2 | 3 | 3155.2 | 3356.4 | 3567.6 | 6.63E-03 | 1.10E-02 | 1.25E-02 |

FIG. 11C

| | | | | | | | | | | |
|---|---|---|---|---|---|---|---|---|---|---|
| 92 | $N_5H_4S_2$ | 0 | 5 | 4 | 2 | 3223.2 | 3357.4 | 3568.6 | 7.25E-03 | 6.68E-03 | 1.33E-02 |
| 93 | $F_4N_4H_4S$ | 4 | 4 | 4 | 1 | 3291.2 | 3358.3 | 3569.6 | 0.00E+00 | 0.00E+00 | 0.00E+00 |
| 94 | $FN_7H_3S$ | 1 | 7 | 3 | 1 | 3300.3 | 3367.4 | 3578.6 | 0.00E+00 | 0.00E+00 | 0.00E+00 |
| 95 | $N_8H_5$ | 0 | 8 | 5 | 0 | 3368.4 | 3368.4 | 3579.6 | 2.21E-01 | 1.36E-01 | 2.64E-01 |
| 96 | $N_4H_3S_3$ | 0 | 4 | 3 | 3 | 3171.2 | 3372.4 | 3583.6 | 0.00E+00 | 1.86E-02 | 1.43E-03 |
| 97 | $N_3H_2S_4$ | 0 | 3 | 2 | 4 | 3119.1 | 3387.4 | 3598.7 | 2.64E-03 | 1.57E-02 | 6.39E-03 |
| 98 | $F_4N_2H_2S_3$ | 4 | 2 | 2 | 3 | 3187.1 | 3388.4 | 3599.6 | 4.72E-04 | 1.63E-02 | 1.97E-03 |
| 99 | $F_4N_4H_2S_2$ | 4 | 4 | 2 | 2 | 3280.2 | 3414.4 | 3625.6 | 4.74E-03 | 0.00E+00 | 5.62E-03 |
| 100 | $FN_7HS_2$ | 1 | 7 | 1 | 2 | 3289.3 | 3423.5 | 3634.7 | 5.56E-03 | 2.15E-02 | 9.92E-03 |
| 101 | $N_7H_3S$ | 0 | 8 | 3 | 1 | 3357.3 | 3424.4 | 3635.7 | 2.21E-03 | 2.36E-02 | 4.20E-03 |
| 102 | $F_4N_7H_3$ | 4 | 7 | 3 | 0 | 3425.4 | 3425.4 | 3636.6 | 0.00E+00 | 0.00E+00 | 0.00E+00 |
| 103 | $F_3N_4H_4S_2$ | 3 | 4 | 4 | 2 | 3458.3 | 3592.5 | 3803.7 | 3.76E-03 | 2.47E-02 | 9.29E-03 |
| 104 | $F_4N_6H_3S$ | 4 | 6 | 3 | 1 | 3535.4 | 3602.5 | 3813.7 | 3.48E-02 | 2.10E-02 | 3.38E-02 |
| 105 | $F_3N_3H_4S_3$ | 3 | 3 | 3 | 3 | 3406.2 | 3607.5 | 3818.7 | 8.96E-03 | 5.04E-03 | 1.37E-02 |
| 106 | $F_3N_3H_8S$ | 3 | 3 | 8 | 1 | 3590.3 | 3657.4 | 3868.6 | 8.49E-03 | 7.47E-03 | 1.11E-02 |
| 107 | $FN_4H_4S_3$ | 1 | 4 | 4 | 3 | 3479.3 | 3680.5 | 3891.7 | 0.00E+00 | 0.00E+00 | 0.00E+00 |
| 108 | $FN_5H_3S_3$ | 1 | 5 | 3 | 3 | 3520.3 | 3721.6 | 3932.8 | 2.43E-03 | 6.43E-03 | 6.26E-03 |
| 109 | $F_4N_5H_5S$ | 4 | 5 | 5 | 1 | 3656.4 | 3723.5 | 3934.7 | 2.84E-03 | 1.13E-02 | 1.19E-02 |
| 110 | $N_9H_6$ | 0 | 9 | 6 | 0 | 3733.5 | 3733.5 | 3944.7 | 1.72E-02 | 5.09E-02 | 3.51E-02 |
| 111 | $FN_4H_2S_4$ | 1 | 4 | 2 | 4 | 3468.3 | 3736.6 | 3947.8 | 1.47E-03 | 1.07E-02 | 7.18E-03 |
| 112 | $N_5H_4S_3$ | 0 | 5 | 4 | 3 | 3536.3 | 3737.6 | 3948.8 | 2.14E-03 | 1.01E-02 | 3.83E-03 |
| 113 | $F_4N_4H_4S_2$ | 4 | 4 | 4 | 2 | 3604.3 | 3738.5 | 3949.7 | 0.00E+00 | 2.49E-02 | 7.50E-03 |
| 114 | $N_4H_3S_4$ | 0 | 4 | 3 | 4 | 3484.2 | 3752.6 | 3963.8 | 3.78E-03 | 9.60E-03 | 6.36E-03 |
| 115 | $F_4N_3H_3S_3$ | 4 | 3 | 3 | 3 | 3552.3 | 3753.5 | 3964.8 | 0.00E+00 | 0.00E+00 | 5.23E-03 |
| 116 | $FN_8H_2S_2$ | 1 | 8 | 2 | 2 | 3654.4 | 3788.6 | 3999.8 | 2.64E-03 | 1.17E-02 | 3.59E-03 |
| 117 | $N_9H_4S$ | 0 | 9 | 4 | 1 | 3722.5 | 3789.6 | 4000.8 | 0.00E+00 | 1.15E-02 | 4.08E-03 |
| 118 | $F_4N_4H_3S_3$ | 4 | 4 | 3 | 3 | 3755.4 | 3956.6 | 4167.9 | 2.25E-03 | 3.90E-02 | 8.52E-03 |
| 119 | $F_3N_5H_5S_2$ | 3 | 5 | 5 | 2 | 3823.4 | 3957.6 | 4168.8 | 0.00E+00 | 2.65E-02 | 0.00E+00 |
| 120 | $F_3N_4H_4S_3$ | 3 | 4 | 4 | 3 | 3771.4 | 3972.6 | 4183.9 | 4.81E-03 | 2.34E-02 | 1.12E-02 |
| 121 | $FN_5H_5S_3$ | 1 | 5 | 5 | 3 | 3844.4 | 4045.7 | 4256.9 | 0.00E+00 | 0.00E+00 | 0.00E+00 |
| 122 | $FN_4H_4S_4$ | 1 | 4 | 4 | 4 | 3792.4 | 4060.7 | 4271.9 | 0.00E+00 | 0.00E+00 | 0.00E+00 |
| 123 | $F_2N_6H_3S_3$ | 2 | 6 | 3 | 3 | 3869.5 | 4070.7 | 4281.9 | 0.00E+00 | 1.08E-02 | 0.00E+00 |
| 124 | $FN_6H_4S_3$ | 1 | 6 | 4 | 3 | 3885.5 | 4086.7 | 4297.9 | 4.04E-03 | 3.29E-02 | 1.08E-02 |
| 125 | $FN_5H_3S_4$ | 1 | 5 | 3 | 4 | 3833.4 | 4101.7 | 4313.0 | 1.27E-03 | 3.17E-02 | 3.46E-03 |
| 126 | $N_6H_5S_3$ | 0 | 6 | 5 | 3 | 3901.5 | 4102.7 | 4313.9 | 0.00E+00 | 0.00E+00 | 0.00E+00 |
| 127 | $F_4N_5H_5S_2$ | 4 | 5 | 5 | 2 | 3969.5 | 4103.7 | 4314.9 | 0.00E+00 | 1.27E-02 | 0.00E+00 |
| 128 | $F_4N_8H_6$ | 4 | 8 | 6 | 0 | 4114.6 | 4114.6 | 4325.9 | 2.10E-02 | 9.72E-02 | 4.17E-02 |
| 129 | $N_5H_4S_4$ | 0 | 5 | 4 | 4 | 3849.4 | 4117.7 | 4329.0 | 0.00E+00 | 2.45E-02 | 7.01E-03 |
| 130 | $F_4N_4H_4S_3$ | 4 | 4 | 4 | 3 | 3917.4 | 4118.7 | 4329.9 | 0.00E+00 | 9.81E-03 | 0.00E+00 |
| 131 | $F_3N_8H_7$ | 3 | 8 | 7 | 0 | 4130.6 | 4130.6 | 4341.9 | 5.92E-03 | 2.26E-02 | 1.18E-02 |
| 132 | $F_4N_3H_3S_4$ | 4 | 3 | 3 | 4 | 3865.4 | 4133.7 | 4345.0 | 7.22E-04 | 3.80E-02 | 5.41E-03 |
| 133 | $FN_9H_3S_2$ | 1 | 9 | 3 | 2 | 4019.6 | 4153.8 | 4365.0 | 4.76E-03 | 2.79E-02 | 9.86E-03 |
| 134 | $N_9H_4S_2$ | 0 | 9 | 4 | 2 | 4035.6 | 4169.8 | 4381.0 | 2.07E-03 | 2.02E-02 | 6.98E-03 |
| 135 | $F_4N_8H_4S$ | 4 | 8 | 4 | 1 | 4103.6 | 4170.7 | 4381.9 | 4.47E-04 | 2.63E-02 | 6.09E-03 |
| 136 | $F_3N_6H_3S_3$ | 3 | 6 | 3 | 3 | 4015.5 | 4216.8 | 4428.0 | 5.91E-04 | 1.32E-02 | 3.28E-03 |
| 137 | $N_6H_4S_4$ | 0 | 6 | 4 | 4 | 4052.5 | 4320.8 | 4532.1 | 0.00E+00 | 0.00E+00 | 0.00E+00 |
| 138 | $F_4N_4H_3S_4$ | 4 | 4 | 3 | 4 | 4068.5 | 4336.8 | 4548.0 | 0.00E+00 | 0.00E+00 | 0.00E+00 |

FIG. 11D

| | | | | | | | | | | | |
|---|---|---|---|---|---|---|---|---|---|---|---|
| 139 | $F_3N_5H_5S_3$ | 3 | 5 | 5 | 3 | 4136.5 | 4337.8 | 4549.0 | 0.00E+00 | 1.79E-02 | 5.47E-03 |
| 140 | $FN_6H_4S_4$ | 1 | 6 | 4 | 4 | 4198.6 | 4466.9 | 4678.1 | 2.81E-03 | 1.86E-02 | 4.00E-03 |
| 141 | $F_4N_6H_6S_2$ | 4 | 6 | 6 | 2 | 4334.6 | 4468.8 | 4680.0 | 0.00E+00 | 5.72E-03 | 0.00E+00 |
| 142 | $F_4N_9H_7$ | 4 | 9 | 7 | 0 | 4479.8 | 4479.8 | 4691.0 | 4.00E-03 | 4.23E-02 | 7.83E-03 |
| 143 | $N_6H_5S_4$ | 0 | 6 | 5 | 4 | 4214.5 | 4482.9 | 4694.1 | 2.12E-03 | 5.26E-02 | 3.45E-03 |
| 144 | $F_4N_5H_5S_3$ | 4 | 5 | 5 | 3 | 4282.6 | 4483.8 | 4695.1 | 0.00E+00 | 6.64E-03 | 0.00E+00 |
| 145 | $F_4N_4H_4S_4$ | 4 | 4 | 4 | 4 | 4230.5 | 4498.9 | 4710.1 | 0.00E+00 | 1.30E-02 | 2.34E-03 |
| 146 | $F_2N_9H_2S_3$ | 2 | 9 | 2 | 3 | 4316.7 | 4517.9 | 4729.2 | 2.30E-03 | 1.37E-02 | 7.88E-03 |
| 147 | $FN_9H_3S_3$ | 1 | 9 | 3 | 3 | 4332.7 | 4533.9 | 4745.2 | 5.51E-04 | 1.24E-02 | 1.20E-03 |
| 148 | $F_3N_6H_5S_3$ | 3 | 6 | 5 | 3 | 4339.6 | 4540.9 | 4752.1 | 0.00E+00 | 9.48E-03 | 2.81E-03 |
| 149 | $F_4N_6H_4S_4$ | 4 | 6 | 4 | 4 | 4433.6 | 4702.0 | 4913.2 | 0.00E+00 | 1.07E-02 | 0.00E+00 |
| 150 | $FN_6H_6S_4$ | 1 | 6 | 6 | 4 | 4522.7 | 4791.0 | 5002.2 | 0.00E+00 | 0.00E+00 | 0.00E+00 |
| 151 | $FN_7H_5S_4$ | 1 | 7 | 5 | 4 | 4563.7 | 4832.0 | 5043.3 | 0.00E+00 | 9.41E-03 | 0.00E+00 |
| 152 | $F_4N_7H_7S_2$ | 4 | 7 | 7 | 2 | 4699.8 | 4834.0 | 5045.2 | 1.92E-03 | 5.11E-03 | 5.81E-03 |
| 153 | $F_5N_5H_4S_4$ | 5 | 5 | 4 | 4 | 4579.7 | 4848.0 | 5059.3 | 0.00E+00 | 4.15E-02 | 3.35E-03 |
| 154 | $F_4N_5H_5S_4$ | 4 | 5 | 5 | 4 | 4595.7 | 4864.0 | 5075.2 | 0.00E+00 | 8.97E-03 | 0.00E+00 |
| 155 | $N_5H_5S_6$ | 0 | 5 | 5 | 6 | 4637.6 | 5040.1 | 5251.4 | 0.00E+00 | 0.00E+00 | 0.00E+00 |
| 156 | $F_3N_8H_8S_2$ | 3 | 8 | 8 | 2 | 4918.9 | 5053.0 | 5264.3 | 0.00E+00 | 0.00E+00 | 0.00E+00 |
| 157 | $FN_5H_5S_6$ | 1 | 5 | 5 | 6 | 4783.7 | 5186.2 | 5397.4 | 0.00E+00 | 2.72E-02 | 0.00E+00 |
| 158 | $FN_7H_5S_5$ | 1 | 7 | 5 | 5 | 4876.8 | 5212.2 | 5423.4 | 0.00E+00 | 2.35E-02 | 0.00E+00 |
| 159 | $F_4N_7H_7S_3$ | 4 | 7 | 7 | 3 | 5012.9 | 5214.1 | 5425.4 | 0.00E+00 | 1.13E-02 | 0.00E+00 |

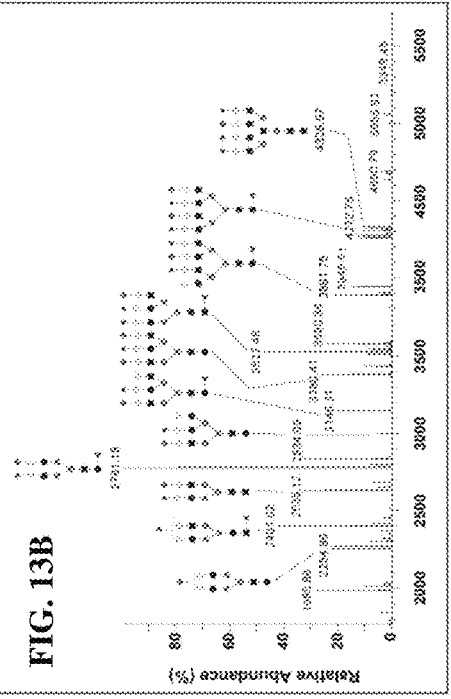
FIG. 13A
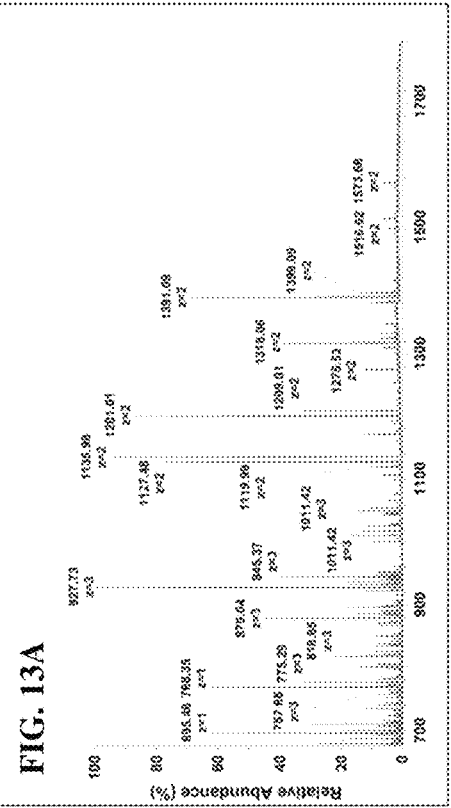
FIG. 13C
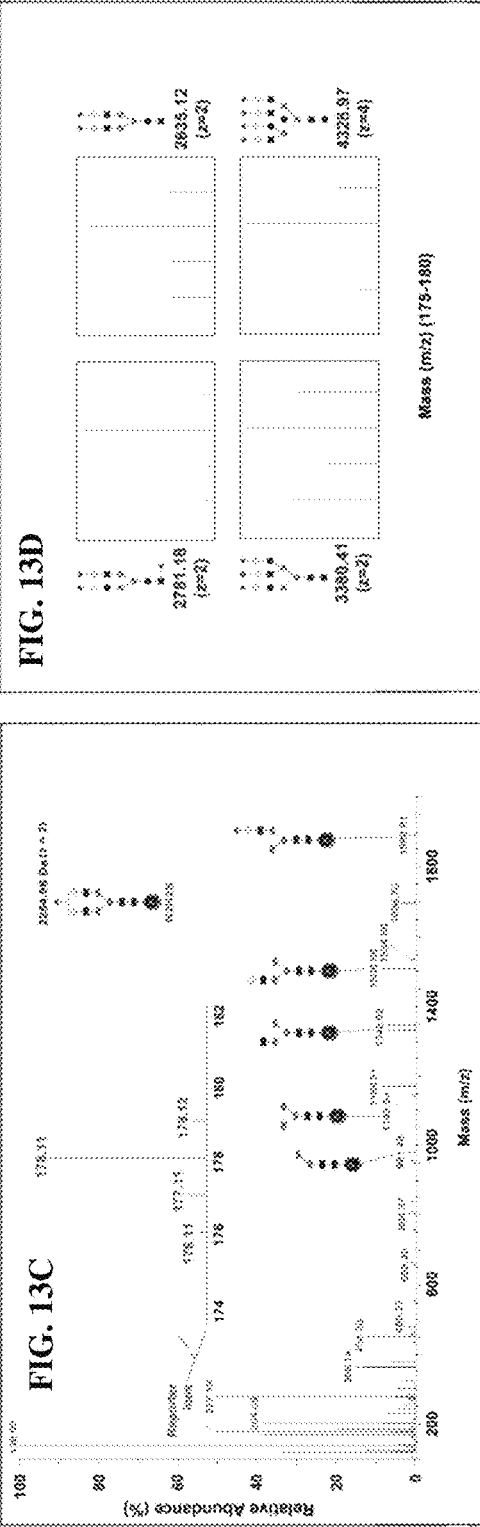
FIG. 13B
FIG. 13D

FIG. 14A
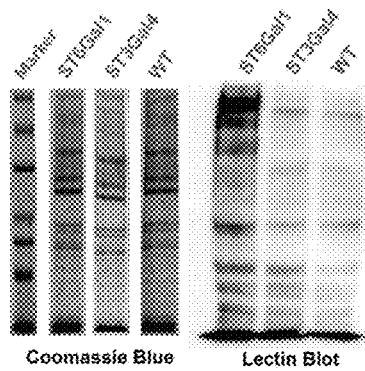
FIG. 14C
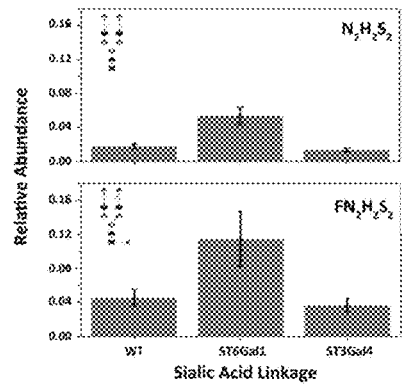
FIG. 14D
FIG. 14B
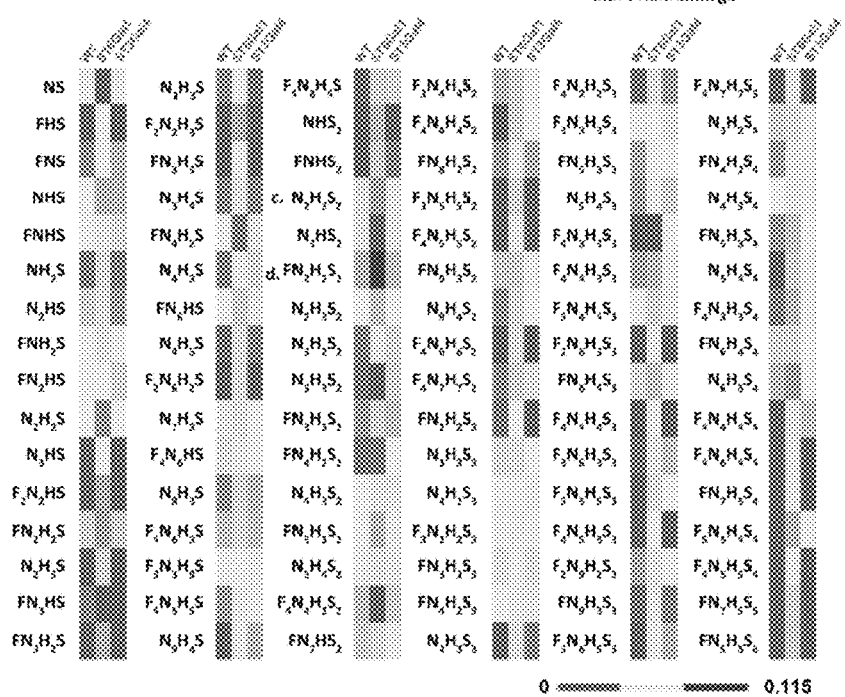

QUATERNARY AMMONIUM CONTAINING ISOBARIC TAG FOR QUANTITATIVE GLYCAN PROFILING

CROSS REFERENCE TO RELATED APPLICATIONS

This application claims the benefit of priority of U.S. Provisional Patent Application No. 62/063,111, filed Oct. 13, 2014 in the name of Shuwei Li and titled "Quaternary Amine Based Isobaric Tag (QABIT) for Quantitative Glycan Profiling" and this application claims the benefit of priority of U.S. Provisional Patent Application No. 62/239,576 filed Oct. 9, 2015 in the name of Shuwei Li for "Quaternary Amine Based Isobaric Tag (QABIT) for Quantitative Glycan Profiling." The disclosures of these U.S. Provisional Patent Applications are hereby incorporated herein by reference in their respective entireties for all purposes.

GOVERNMENT RIGHTS IN INVENTION

This invention was made with government support under HL107153 awarded by National Institutes of Health. The government has certain rights in the invention.

FIELD

The present disclosure relates to reagents for the analysis of biological matter, particularly reagents for the analysis of biomolecules by quantitation. More particularly, the disclosure relates to the design and synthesis of a set of isobaric tags that are based on quaternary ammonium for quantitative glycan profiling. The technology has broad applications in carbohydrate analysis for biomarker discovery, therapeutic protein characterization, and vaccine development.

DESCRIPTION OF THE RELATED ART

Carbohydrate is one of the macromolecules that plays a vital role in biological processes and glycoconjugates are common modifications to other macromolecules. Dove, A *Nat. Biotechnol.* 2001, 19. 913-917; Dennis, J. W. et al., *M. Cell* 2009, 139, 1229-1241. For example, many therapeutic proteins (e.g. monoclonal antibodies) are decorated with various glycans, whose composition and stoichiometry can affect their stability and efficacy. Walsh, G.; Jefferis, R., *Nat. Biotechnol.* 2006, 24, 1241-1252. As a result, qualitative and quantitative determination of glycans is of great significance for both biomedical and biotechnological applications. Marino, K. et al. *Nat. Chem. Biol.* 2010, 6, 713-723. However, the study of glycans and comprehensive profiling thereof lags far behind other biomolecules due to technical challenges associated with their chemical properties and structural complexity.

Glycans (a.k.a. carbohydrate or polysaccharide) are an important class of biomolecules that play critical roles in biological processes such as protein trafficking, cell-to-cell communication and immune responses, and their abnormality is associated with numerous diseases including cancer, dementia, and autoimmune disorders. The potency and stability of therapeutic biological drugs like monoclonal antibodies are also affected by glycans they carry. For these reasons, glycan analysis (for quality control, disease diagnosis, etc.) is of great value in academic research, pharmaceutical industry and healthcare. However, glycans are hydrophilic molecules that lack UV absorbance and ionize poorly in mass spectrometry (MS). Their structures are highly heterogeneous, as each glycan can have multiple regio- and stereo-isomers. In addition, glycan biosynthesis is a non-template-driven process, making it difficult to predict their compositions and structures.

To overcome these obstacles, glycans are usually derivatized to improve their performance in various analytical platforms, especially mass spectrometry (MS). Ruhaak, L. R. et al. *Anal. Bioanal. Chem.* 2010, 397, 3457-3481. Labeling with fluorogenic 2-aminobenzoic acid (2-AA) and 2-aminobenzamide (2-AB) can make them compatible with fluorescence detection and enhance their signal in MS as well. Bigge, J. C. et al. *Anal. Biochem.* 1995, 230, 229-238. But fluorescent tags are limited in quantifying complex glycan samples due to peak co-elution. Per-methylation of hydroxyl groups on glycans can improve their mass spectrometry detection and result in high-quality MS2 spectra for structural elucidation, yet achieving accurate quantitation is challenging and suffers from batch-to-batch variations. Kang, P. et al. *Rapid Commun. Mass Spectrom.* 2005, 19, 3421-3428. Recently, stable isotope labeling, in conjugation with 2-AA/2-AB labeling (Prien, J. M. et al. *Anal. Chem.* 2010, 82, 1498-1508) and per-methylation (Alvarez-Manilla, G. et al. *Glycobiology* 2007, 17, 677-687) has gained increasing attention to assist in glycan characterization and quantification. Bowman, M. J. et al. *Anal. Chem.* 2007, 79, 5777-5784.

There are two types of stable isotope labeling approaches, mass-shift and isobaric tags. Mass-shift tags render analytes from various samples to differ in their precursor mass (MS1) by a few Daltons and the quantification is achieved on MS1 by comparing the intensity of corresponding peaks. In contrast, isobaric tags are a group of molecules with identical chemical structure and molecular mass, but differing in the positions of various heavy nuclei in their structure. Therefore, once samples are labeled by a set of isobaric tags, they do not show difference in MS1. Upon MS/MS fragmentation, a series of signature low mass reporter ions is generated for quantification. Compared to mass-shift tags, isobaric labeling allows quantification of up to ten samples concurrently with commercially available tandem mass tag (TMT) 10-plex, (McAlister, G. C. et al. *Anal. Chem.* 2012, 84, 7469-7478) does not introduce more complexity into MSI spectra, and increases the detection limit by accumulating signals from multiple samples together; therefore, it has been widely used for large-scale quantification of proteins (Zhang, J.; Wang, Y.; Li, S. *Anal. Chem.* 2010, 82, 7588-7595; Zeng, D.; Li, S. *Chem. Commun.* 2009, 3369-3371; Chen, Z. et al. *Anal. Chem.* 2012, 84. 2908-2915) and small molecule metabolites. Yuan, W. et al. *Proteome Res.* 2011, 10, 5242-5250; Yuan, W. et al. *Anal. Chem.* 2012, 84, 2892-2899.

There have been attempts to apply isobaric labeling for glycan quantification. Yang, S. et al. *Anal. Chem.* 2013, 85, 8188-8195; Hahne, H. et al. *Anal. Chem.* 2012, 84, 3716-3724. However, because glycosidic bonds in glycans break favorably upon MS/MS fragmentation and compete with the generation of report ions, isobaric tags originally designed for peptides often fail to yield enough reporter ions for quantification. As a remedy, labeled glycans have to be mixed with sodium chloride (NaCl) for MS analysis because $Na^+$ can assist in the fragmentation of isobaric tags to generate more reporter ions. A limitation of this approach is that salt can severely suppress the signal of glycans in electrospray ionization, ESI-MS. Glycans may also form multiple $H^+/Na^+$ adducts and average out their intensity to more species, further reducing their detection sensitivity.

Accordingly, there is a need in the art for reagents and methods for glycan analysis, particularly enhanced quantitative glycan profiling.

SUMMARY

The present disclosure relates to quaternary ammonium containing isobaric tag reagents useful in the analysis of biomolecules and methods of making and using the quaternary ammonium containing isobaric tag reagents. The quaternary ammonium containing isobaric tag reagents are particularly useful for glycan analysis such as glycan quantitation by tandem mass spectrometry.

In one aspect, a method of N-glycan analysis is provided comprising labeling N-glycans with a quaternary ammonium containing isobaric tag reagent comprising an MS/MS scissionable bond and a reactive group capable of conjugating with N-glycans.

In another aspect, the disclosure relates to a quaternary ammonium containing isobaric tag reagent comprising the formula: reporter group-balancer group-reactive group, wherein the reagent has the structure:

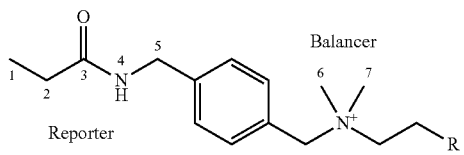

wherein at least one of positions 1-7 comprises an isotope atom, the reporter group and balancer group are linked by an MS/MS scissionable bond, and R is a reactive group (e.g. primary amine, hydrazide, or aminooxy group) and is capable of conjugating with glycans. In some aspects, the reporter group has a mass in a range of from 176 to 179 Da, the reagent contains 2 or 3 isotope atoms independently selected from $^{13}C$ and $^{2}H$, and the reactive group comprises a reactive primary amine capable of conjugating with glycans via reductive amination.

In another aspect, the disclosure relates to a method of quantitative glycan profiling comprising: (a) labeling glycans with a quaternary ammonium containing isobaric tag reagent comprising the formula: reporter group-balancer group-reactive group, wherein the reporter group and balancer group are linked by an MS/MS scissionable bond and the reactive group is capable of conjugating with glycans; and (b) quantitatively analyzing the labeled glycans. In some aspects, the reporter group has a mass in a range of from 176 to 179 Da, the reagent contains 2 or 3 isotope atoms independently selected from $^{13}C$ and $^{2}H$, and the reactive group comprises a reactive primary amine capable of conjugating with glycans via reductive amination In a further aspect of the disclosure, a method of enhancing sensitivity of glycans for glycomic analysis is provided comprising labeling the glycans with a quaternary ammonium containing isobaric tag reagent.

Other aspects, features and embodiments of the invention will be more fully apparent from the ensuing disclosure and appended claims.

BRIEF DESCRIPTION OF THE DRAWINGS

FIG. 2A shows combined MS1 peaks from 20 to 28 minutes and possible structures of identified glycan peaks. Two non-annotated peaks, 878.72 (z=3) and 1127.49 (z=3) are different charge states of annotated ions 1317.57 (z=2) and 845.61 (z=4), respectively. The black square represents GlcNAc; the dark grey circle represents mannose; the light grey circle represents galactose and the diamond represents sialic acid; Cts represents ion counts. FIG. 2B shows MS/MS of a precursor ion (structure in inset) (1317.57 Da) (z=2) with some of its fragments structures also shown. FIG. 2C shows the ratio of reporter ions (176-179) of several precursor ions on MS1 spectra.

FIG. 7A-7F illustrates a comparison of N-glycans labeling by a quaternary ammonium containing isobaric tag reagent and aminoxyTMTzero™. Standard sialylglycopeptide (SGP) is used for labeling via reduction amination (1 M NaCHBH$_3$, DMSO:AcOH=7:3, 65° C./4 h). SGP has two sialic acids including $N_2H_2S$ and $N_2H_2S_2$. FIG. 7A is a MS1 spectrum of SGP-QUANTITY; FIG. 7B is a MS1 spectrum of $N_2H_2S_2$-QUANTITY; FIG. 7C shows MS2 reporter ions of $N_2H_2S_2$-QUANTITY; FIG. 7D is a MS1 spectrum of SGP-aminoxyTMTzero™ (or SGP-TMT); FIG. 7E is a MS1 spectrum of $N_2H_2S_2$-TMT; FIG. 7F shows MS2 reporter ions of $N_2H_2S_2$-TMT.

FIG. 8A is native SGP N-glycans extracted from glycoprotein immobilization for glycan extraction (GIG); FIG. 8B is aminoxyTMT-126 labelled SGP N-glycans; FIG. 8C is QUANTITY-labelled SGP N-glycans.

FIG. 9A is a MS spectrum of fetuin N-glycans; FIG. 9B is a $MS^2$ spectra of $N_2H_2S_2$ consist of glycan fragmentation and QUANTITY reporter ions; FIG. 9C is a graphical representation of the linear range of glycan-QUANTITY labeling at a ratio of 1:1:3:5.

FIG. 11A-D is a list of QUANTITY-labeled glycans from the pooled CHO cell lines. CHO WT is labeled with QUANTITY 176, CHO.ST6 with 178 and CHO.ST3Gal4 with 179.

FIG. 13A-13D shows MS profiling and MS/MS quantitation of QUANTITY-labeled glycans from ST6Gal1 (+) and ST3Gal4 (−) CHO cells. Glycans were extracted using the method described in FIG. 1. FIG. 13A is a MS' spectrum of CHO glycans with multiple charges; FIG. 13B is a MS' spectrum of CHO glycans after converting to single charge; FIG. 13C is a $MS^2$ spectrum of one sialylated glycan, $N_2H_2S$; FIG. 13D shows quantitation using reporter ions from four QUANTITY-labeled glycans.

FIG. 14A-14D illustrates regulation of sialic acid in CHO by ST6Gal1(+) and ST3Gal4(−). FIG. 14A shows Coomassie blue of CHO cell proteins on WT, ST6Gal1, and ST3Gal4; the Lectin blot by anti-SNA on WT and ST6Gal1 indicates increased sialic acid expression in ST6Gal1 knockin CHO cells. FIG. 14B is a heatmap of sialylated N-glycans from CHO cell glycoproteins on WT, ST6Gal1, and ST3Gal4. Quantitation is obtained from $MS^2$ of QUANTITY-labeled N-glycans. Increase of sialic acid expression is in ST6Gal1(+) while down-regulated expression is observed in ST3Gal4(−), such as FIG. 14C $N_2H_2S_2$, FIG. 14D $FN_2H_2S_2$.

DETAILED DESCRIPTION

Figure 1A:
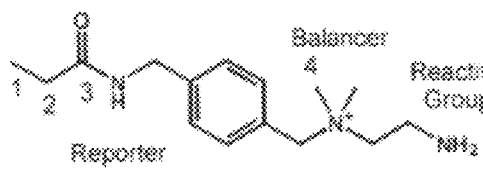
FIG. 1A provides the molecular structure of a Quaternary Ammonium Containing Isobaric Tag for Glycan (QUANTITY) reagent according to the disclosure, demonstrating each of the reporter group, balancer group, and reactive group. The table in FIG. 1A lists isotope positions in each exemplified reagent.

The present disclosure relates to quaternary ammonium containing isobaric tag reagents useful in the analysis of biomolecules and methods of making and using the quaternary ammonium containing isobaric tag reagents. The quaternary ammonium containing isobaric tag reagents are particularly useful for quantitative glycan profiling.

As used herein and in the appended claims, the singular forms "a", "and", and "the" include plural referents unless the context clearly dictates otherwise. Like numbers refer to like elements throughout. All figures with structural elements have the same key, i.e., the black square represents GlcNAc; the dark grey circle represents mannose; the light grey circle represents galactose and the diamond represents sialic acid.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure correspondingly contemplates such features, aspects and embodiments, or a selected one or ones thereof, in various permutations and combinations, as being within the scope of the present disclosure.

The reagents of the disclosure are useful for labeling or tagging samples for analysis by quantitation methods. "Quantitation" or "quantitative analysis" as used herein, refers to analysis of the composition of a sample. Quantitation allows identification of measurable properties of a sample subject to such analysis, such as the relative amounts of the elements of the sample, regardless of the source of the elements within the sample. Quantitation methods may include, but are not limited to high pressure liquid chromatography (HPLC), UV detection and mass spectrometry (MS).

The present disclosure generally relates to reagents comprising isobaric tags useful in quantitation of biomolecules, In particular, the disclosure relates to reagents comprising isobaric tags useful in quantitative glycomics and glycomic analysis. The quaternary ammonium containing isobaric tags according to the disclosure are capable of fragmenting as easily as glycosidic bonds so that labeled glycans can produce enough reporter ions for analysis. In particular, such analysis may occur without the use of $Na^+$ or other metal ions. Accordingly, the disclosure provides the preparation of glycan-reactive quaternary ammonium containing isobaric tag reagents and their use in the quantification of quaternary ammonium containing isobaric tag-labeled glycans, for example, by tandem mass spectrometry (MS/MS).

To improve the reporter ion intensity of isobaric labeled glycans, it is desirable to develop isobaric tags capable of fragmenting as easily as glycosidic bonds so that labeled glycans can produce strong reporter ions for accurate glycan quantification. It has now been discovered that a quaternary ammonium can easily lose one of its four substituents on nitrogen upon MS/MS fragmentation, even when it is coupled to a glycan. Based on this observation, a new type of isobaric tag (named alternately as QABIT: quaternary ammonium based isobaric tag; or Quaternary Ammonium Containing Isobaric Tag for Glycan (QUANTITY)) was synthesized. Such isobaric tag, is suitable, for example, for 4-plex glycan quantification. As used herein, the term QUANTITY may include any quaternary ammonium based isobaric tag according to the disclosure or a particular structure thereof.

Quaternary Ammonium Containing Isobaric Tag for Glycan (QUANTITY) is provided herein as useful in a quantitative method that not only enhances detection limit of glycans by mass spectrometry, but also, in some embodiments, allows up to four biological samples to be analyzed concurrently. In aspects of the disclosure, this robust tool enables the ability to accomplish glycomic survey of bio-engineered Chinese Hamster Ovary (CHO) cells with either knock-in or knock-out enzymes involved in protein glycosylation. The results obtained using quaternary ammonium containing isobaric tag reagent may provide critical clues on how to engineer CHO cells for therapeutic proteins production with better pharmaceutical properties.

The present disclosure provides a quaternary ammonium containing isobaric tag reagent comprising a reactive group capable of conjugation with glycans. In embodiments, the quaternary ammonium containing isobaric tag reagent comprises a primary amine reactive group capable of conjugation with glycans via reductive amination.

The quaternary ammonium containing isobaric tag reagent according to the disclosure generally comprises a reporter group-balancer group-reactive group, wherein the reporter group and balancer group are linked by an MS/MS scissionable bond, easily fragmented in MS/MS.

In embodiments, the structures of the isobaric tags of the disclosure comprise a reporter with molecular mass ranging from 176 to 181 Daltons in the series, preferably 176-179 Da, a balancer that compensates the mass difference of the reporters and a reactive group to conjugate with glycans. In particular embodiments, the quaternary ammonium containing isobaric tag reagent comprises a primary amine reactive group capable of conjugation with glycans via reductive amination.

In some embodiments, the isobaric tag reagents of the disclosure are 4-plex quaternary ammonium containing reagents comprising a set of four molecules with identical chemical structures and molecular weight, having different stable nuclei such as $^{15}N$, $^{13}C$ and $^{2}H$ in various positions of the molecule. In other embodiments, the isobaric tag reagents may be 6-plex or greater with heavy isotope atoms at additional positions.

The selection of substituents in each of the reporter group and balancer group is made such that the change in mass attributable to the selection of substituents in the reporter group is offset by the change in mass attributable to the selection of substituents in the balancer group. Accordingly, varying isotopic forms of a reagent will have the same total sum of the mass of the reporter group plus the mass of the balancer group.

FIG. 1 exemplifies quaternary ammonium containing isobaric tag reagent structures according to the disclosure which consist of a reporter with molecular mass ranging from 176 to 179 Da in the series, a balancer that compensates the mass difference of the reporter, and a reactive primary amine to couple with glycans via reductive amination. As shown, positions 1, 2, 3 and 4 may be substituted with one or more of $^{13}C$ and/or $^{2}H$.

The labeling chemistry for quaternary ammonium containing isobaric tag reagents according to the disclosure may be conducted in an analogous manner as 2-AA/2-AB (2-aminobenzoic acid (2-AA) or 2-aminobenzamide (2-AB)), so well-established protocols for 2-AA/2-AB labeling may be adapted. After the reductive amination is completed, a water molecule is lost spontaneously and stoichiometrically, probably through an energetically favored six-membered ring formation. This intramolecular condensation is also observed in 2-AA/2-AB labeled glycans, albeit at lower level because rigid aromatic amine in 2-AA/2-AB somehow prevents 100% loss of the water.

Upon MS/MS fragmentation, glycans labeled with quaternary ammonium containing isobaric tag reagent can yield strong reporter ions for accurate quantification. Furthermore, outfitting glycans with a permanently positive-charged quaternary ammonium can enhance their ionization in MS. Consequently, the detection sensitivity of glycans is considerably enhanced, which is advantageous when analyzing low abundance glycans or samples with limited supply. The quaternary ammonium containing isobaric tag reagents according to the disclosure are the first isobaric tags for glycan analysis and/or quantification based on quaternary ammonium. These reagents use analogous chemistry to 2-AA/2-AB, so well-established protocols for 2-AA/2-AB labeling and sample preparation can be adapted. See, for example, U.S. Pat. No. 5,747,347, incorporated here by reference in its entirety. Because quaternary ammonium is permanently positive-charged, quaternary ammonium containing isobaric tag-labeled glycans ionize easily in MS and improve their detection limit significantly.

Even though isobaric tags have been widely used for the quantification of peptides and small molecule metabolites, previous attempts for glycan quantification based on tertiary amine have achieved limited success. U.S. Patent Application Publication No. 2015/0241437, now U.S. Pat. No. 9,939,444, issued Apr. 10, 2018, and incorporated herein by reference; Hahne, H. et al. "Carbonyl-reactive tandem mass tags for the proteome-wide quantification of N-linked glycans," Anal. Chem. 84, 3716-3724 (2012). For example, aminoxyTMT labeled glycans need to form metal ion adducts to show reporter ions strong enough for quantification upon fragmentation, which can cause ion suppression in MS and reduce detection sensitivity. This is not surprising because aminoxyTMT and other isobaric tags based on tertiary amine were originally designed for peptide quantification. Since glycosidic bonds in glycans fragment much easier than peptide bonds, aminoxyTMT labeled glycans preferably break apart between glycan units and are therefore inefficient to generate reporter ions. The discovery that quaternary ammonium fragments as easy as glycosidic bonds in MS has made it possible to develop quaternary ammonium containing isobaric tags, which enabled the achievement of global profiling of N-glycans from up to four samples simultaneously for the first time.

Exemplary testing was carried out to determine the effectiveness of quantitative labeling of glycans using quaternary ammonium containing isobaric tags as shown in FIG. 1A for glycan analysis and/or quantitation. The 4-plex quaternary ammonium containing isobaric tags of FIG. 1A were tested on N-glycans extracted from human serum glycoproteins (Yang, S.; Li, Y.; Shah, P.; Zhang, H., Anal. Chem. 2013, 85, 5555-5561) which are often associated with various pathological conditions and provide good targets for biomarker discovery. Kita, Y. et al., S., Mol. Cell. Proteomics 2007, 6, 1437-1445. Because many serum N-glycans carry sialic acids that are easily lost during MS analysis, a solid-phase based approach was employed to stabilize these labile residues. In this protocol, glycoproteins were first immobilized on beads, sialic acids were then coupled with p-toluidine, and N-glycans were enzymatically released from immobilized glycoproteins with PNGase F. This method allowed the modification of sialic acids completely by using a large excess of p-toluidine, which was preferable for accurate quantitative profiling of N-glycans from various samples. This step also added a hydrophobic moiety into each sialic acid, so N-glycans carrying different numbers of sialic acids can be better resolved on reverse phase (C18) chromatography. After N-glycans were cleaved from glycoproteins, an aldehyde group was exposed at the reducing end, which was conjugated with a quaternary ammonium containing isobaric tag in the presence of sodium cyanoborohydride through reductive amination. Four aliquots were labeled of the same N-glycan sample with 4-plex QUANTITY respectively, mixed at 1:1:2:4 ratios, and analyzed with an electrospray ionization (ESI) MS instrument.

Figure 1B:
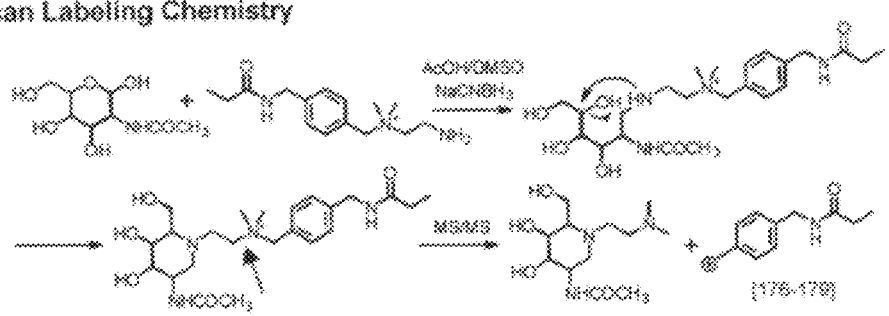
FIG. 1B illustrates N-acetylglucosamine (GlcNAc, the first residue on the reducing end of N-glycans) labeled with quaternary ammonium containing isobaric tag reagent and its fragmentation in $MS^2$. The arrow indicates fragmentation site in $MS^2$.

FIG. 1B illustrates, for example, N-acetylglucosamine, GlcNAc, the first residue on the reducing end of N-glycans, labeled with quaternary ammonium containing isobaric tag reagent and its fragmentation in MS2. The arrow in FIG. 1B indicates the fragmentation site in MS2 for this quaternary ammonium containing isobaric tag.

Figure 1C:
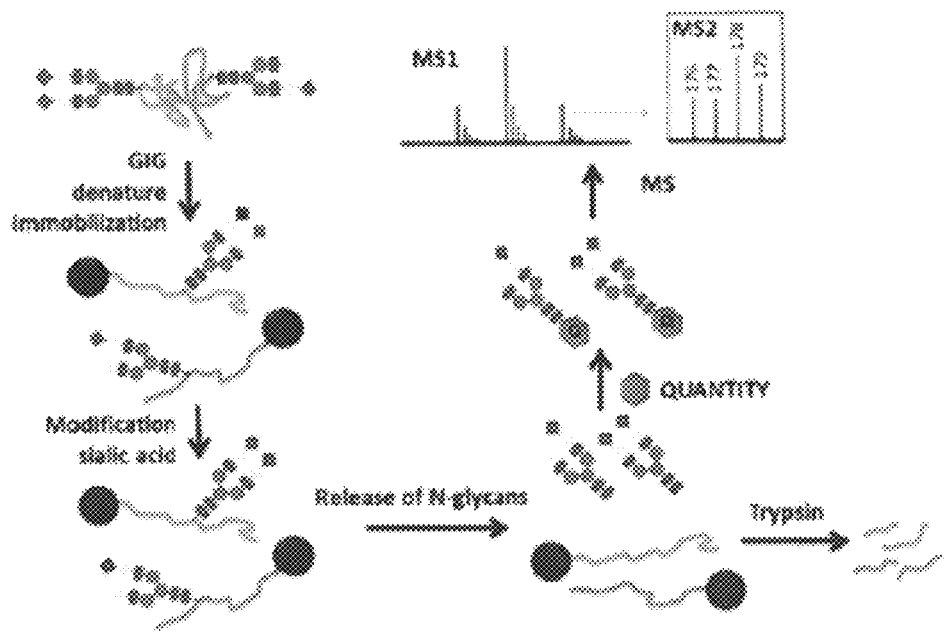
FIG. 1C is a schematic illustration of a solid-phase based protocol for glycan analysis with a quaternary ammonium containing isobaric tag reagent according to aspects of the disclosure. The diagram shows N-glycan extraction from solid-phase for labeling of N-glycans by isobaric tags and analysis of peptide using LC-MS/MS. Proteins are immobilized on beads via reductive amination. Sialic acids are stabilized via carbodiimide coupling. The released N-glycans by PNGase F are labeled by primary amine of a quaternary ammonium containing isobaric tag reagent. The global proteins are further analyzed by direct digestion from beads.

FIG. 1C is a schematic illustration of a solid-phase based protocol for glycan analysis with a quaternary ammonium containing isobaric tag reagent according to aspects of the disclosure. As shown, glycoproteins are first immobilized on beads and treated, for example, with excess p-toluidine (pT) in the presence of a carbodiimide coupling reagent. This step can completely conjugate sialic acids on glycans with pT to stabilize these labile residues during MS analysis. N-glycans are then released from the immobilized glycoproteins, for example, with PNGase F, resulting in an exposed aldehyde group at their reducing end for quaternary ammonium containing isobaric tag reagent labeling. The labeled glycans may then be analyzed, for example, with reverse phase liquid chromatography (RPLC) coupled with tandem MS. A bonus of this protocol is that a hydrophobic pT moiety is coupled to each sialic acid, so N-glycans carrying different number of sialic acids can be easily resolved on a C18 column.

Figure 2A:
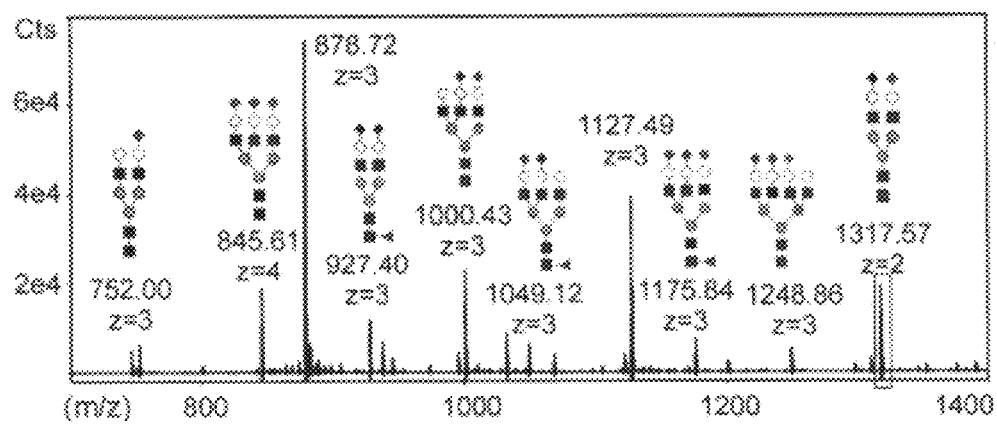
FIG. 2A-2C is spectra from MS and MS/MS of quaternary ammonium containing isobaric tag-labeled N-glycans from human sera.

As shown in FIG. 2A (top), labeled glycan peaks were observed on MS1. Because no Na+ was added when running MS experiments, predominately observed were H$^+$ adducts, making MS spectra easier to interpret. The monoisotopic mass of corresponding native glycans (M) is calculated based on equation 1:

$$M = B \times Z - (Z-1) \times 1.01 - 233.22 - 89.06 \times N \qquad \text{(Equation 1)}$$

Here B and Z are the observed m/z and charge of a labeled glycan on MS1, respectively. N is the number of sialic acid in this glycan. For each peak, N was enumerated from 0 to 4, the mass was calculated, and glycan composition and the most possible structure was identified by searching Consortium for Functional Glycomics (CFG) database in Glyco-WorkBench. Ceroni, A; Maass, K.; Geyer, H.; Geyer, R.; Dell, A; Haslam, S. M. *J., Proteome Res.* 2008, 7, 1650-1659.

Only when the number of sialic acid in a possible structure matched that used in the calculation was the possible glycan structure assigned to the peak. Using this strategy, 30 N-glycans were identified with unique molecular weight from human serum, most of which were heavily sialylated (Table 1 (The black square represents GlcNAc; the dark grey circle represents mannose; the light grey circle represents galactose and the diamond represents sialic acid).

TABLE 1

Identified Serum N-glycans

| m/z | z | Labeled glycan mass | # of sialic acid | Original glycan mass (H$^+$) | Mass accuracy (ppm) | Glycan composition | One of most possible structures[1] |
|---|---|---|---|---|---|---|---|
| 697.98 | 3 | 2091.92 | 1 | 1770.65 | −4.50 | Hex4HexNAc4NeuAc1 | |
| 752.00 | 3 | 2253.98 | 1 | 1932.71 | −7.80 | Hex5HexNAc4NeuAc1 | |
| 800.68 | 3 | 2400.02 | 1 | 2078.75 | 1.33 | Hex5HexNAc4NeuAc1dHex1 | |
| 814.36 | 3 | 2441.06 | 1 | 2119.79 | −5.04 | Hex4HexNAc5NeuAc1dHex1 | |
| 819.69 | 3 | 2457.05 | 1 | 2135.78 | −2.70 | Hex5HexNAc5NeuAc1 | |
| 841.86 | 4 | 3364.41 | 2 | 2954.08 | −8.57 | Hex7HexNAc6NeuAc2 | |
| 845.61 | 4 | 3379.41 | 3 | 2880.02 | −0.73 | Hex6HexNAc5NeuAc3 | |
| 856.38 | 2 | 1711.75 | 0 | 1479.54 | 4.48 | Hex4HexNAc4 | |
| 868.38 | 3 | 2603.12 | 1 | 2281.85 | −7.82 | Hex5HexNAc5NeuAc1dHex1 | |
| 873.71 | 3 | 2619.11 | 1 | 2297.84 | −5.63 | Hex6HexNAc5NeuAc1 | |
| 927.40 | 3 | 2780.18 | 2 | 2369.85 | −0.76 | Hex5HexNAc4NeuAc2dHex1 | |

TABLE 1-continued

Identified Serum N-glycans

| m/z | z | Labeled glycan mass | # of sialic acid | Original glycan mass (H+) | Mass accuracy (ppm) | Glycan composition | One of most possible structures[1] |
|---|---|---|---|---|---|---|---|
| 937.41 | 2 | 1873.81 | 0 | 1641.60 | −0.33 | Hex5HexNAc4 | |
| 944.92 | 2 | 1888.83 | 1 | 1567.56 | 1.70 | Hex4HexNAc3NeuAc1 | |
| 995.09 | 3 | 2983.25 | 2 | 2572.92 | 2.94 | Hex5HexNAc5NeuAc2dHex1 | |
| 995.42 | 3 | 2984.24 | 1 | 2662.97 | −4.03 | Hex7HexNAc6NeuAc1 | |
| 1000.43 | 3 | 2999.27 | 2 | 2588.94 | −0.02 | Hex5HexNAc5NeuAc2 | |
| 1010.44 | 2 | 2019.87 | 0 | 1787.66 | −1.48 | Hex5HexNAc4dHex1 | |
| 1038.93 | 4 | 4152.69 | 1 | 3831.42 | −5.90 | Hex9HexNAc8NeuAc1dHex3 | |
| 1049.12 | 3 | 3145.34 | 2 | 2735.00 | −7.17 | Hex6HexNAc5NeuAc2dHex1 | |
| 1068.45 | 4 | 4270.77 | 4 | 3682.32 | −4.50 | Hex7HexNAc6NeuAc4dHex1 | |
| 1104.96 | 4 | 4416.81 | 4 | 3828.36 | 0.35 | Hex7HexNAc6NeuAc4dHex2 | |
| 1111.98 | 2 | 2222.95 | 0 | 1990.74 | −1.64 | Hex5HexNAc5dHex1 | |
| 1123.22 | 4 | 4489.85 | 4 | 3901.40 | −5.71 | Hex8HexNAc7NeuAc4 | |
| 1136.48 | 3 | 3407.42 | 0 | 3175.21 | −12.67 | Hex8HexNAc7dHex3 | |

TABLE 1-continued

Identified Serum N-glycans

| m/z | z | Labeled glycan mass | # of sialic acid | Original glycan mass (H+) | Mass accuracy (ppm) | Glycan composition | One of most possible structures[1] |
|---|---|---|---|---|---|---|---|
| 1159.73 | 4 | 4635.89 | 4 | 4047.44 | −1.08 | Hex8HexNAc7NeuAc4dHex1 | 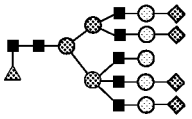 |
| 1175.84 | 3 | 3525.50 | 3 | 3026.10 | −8.00 | Hex6HexNAc5NeuAc3dHex1 | 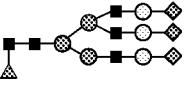 |
| 1248.86 | 3 | 3744.56 | 3 | 3245.17 | −6.14 | Hex7HexNAc6NeuAc3 | 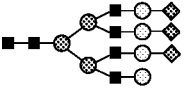 |
| 1297.54 | 3 | 3890.60 | 3 | 3391.21 | −0.59 | Hex7HexNAc6NeuAc3dHex1 | 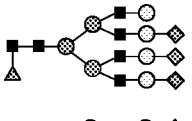 |
| 1317.57 | 2 | 2634.13 | 2 | 2223.80 | −4.41 | Hex5HexNAc4NeuAc2 | 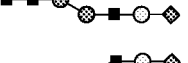 |
| 1346.24 | 3 | 4036.70 | 3 | 3537.31 | −12.47 | Hex7HexNAc6NeuAc3dHex2 | 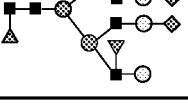 |

(1) The structure listed in the last column of Table 1 is one of possible isomers for a given molecular weight because MS2 spectra usually do not provide enough information for unambiguous assignment of one specific structure from a group of isomers.

Figure 2B:
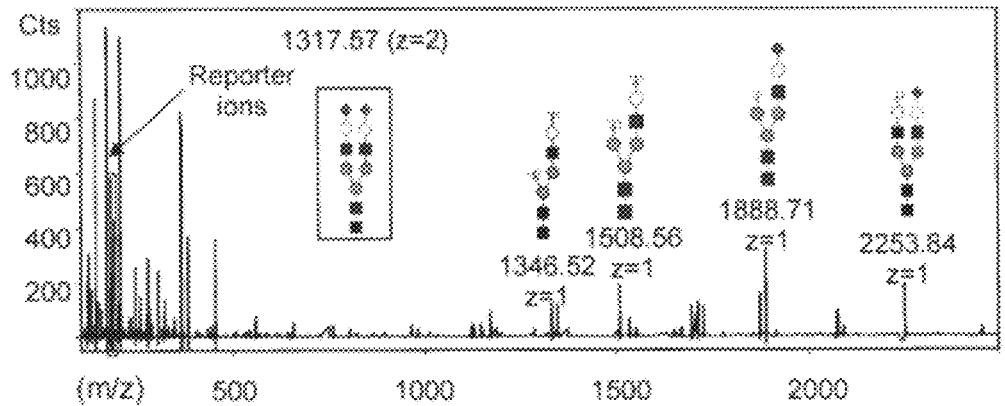

The major peaks as shown on FIG. 2A (top), which is the combined MS1 at retention time from 20 to 28 min, were identified. Two non-annotated peaks, 878.72 (z=3) and 1127-49 (z=3), are different charge states of annotated ions 1317.57 (z=2) and 845.61 (z=4), respectively. Their structures can be further confirmed by their MS2. FIG. 2B (middle) is the full MS2 spectrum of a precursor ion 1317.57 (z=2), from which a biantennary glycan was assigned (Table 2) (The black square represents GlcNAc; the dark grey circle represents mannose; the light grey circle represents galactose and the diamond represents sialic acid).

| Fragment (m/z and z) | Tag form[1][2][3] | Fragment structure |
|---|---|---|
| 1168.41 (z = 1) | tertiary amine | 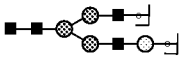 |
| 1330.47 (z = 1) | tertiary amine | 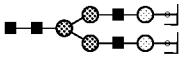 |
| 1346.52 (z = 1) | intact | 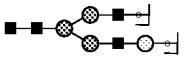 |
| 1508.56 (z = 1) | intact | 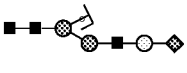 |
| 1533.53 (z = 1) | tertiary amine | 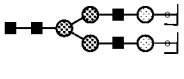 |
| 1695.59 (z = 1) | tertiary amine | 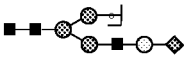 |
| 1711.62 (z = 1) | intact | 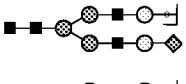 |
| 1726.67 (z = 1) | intact | 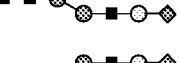 |
| 1873.70 (z = 1) | intact |  |
| 1888.71 (z = 1) | intact |  |
| 2076.73 (z = 1) | tertiary amine |  |
| 2253.84 (z = 1) | intact |  |
| 2456.69 (z = 1) | tertiary amine | 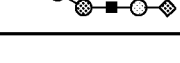 |

With regard to Table 2, (1) Only quaternary ammonium containing isobaric tag coupled fragments are visible in MS2 spectra. Upon MS/MS fragmentation, a quaternary ammonium containing isobaric tag can remain intact or break into one of two forms (carbocation or tertiary amine) as shown below where the quaternary ammonium containing isobaric tag or its fragments are attached to a GlcNAc. (2) It is normal if a fragment containing the tertiary amine form of the quaternary ammonium containing isobaric tag has a mass shift of 1-3 Da away from the calculated monoisotopic mass of this fragment. This mass shift is due to the balancer that is left in the tertiary amine form. (3) The generation of tertiary amine and carbocation ions seems to be exclusive as either tertiary amine or carbocation series fragments can be observed, but not both, on the same MS2 spectrum.

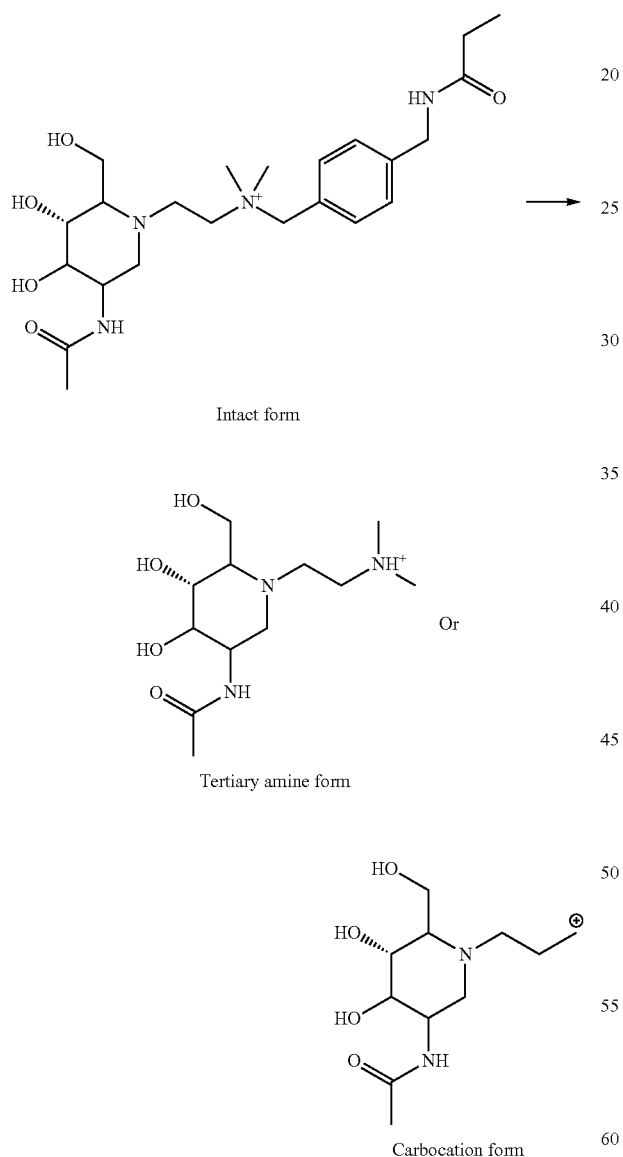

Intact form

Tertiary amine form

Carbocation form

Figure 2C:
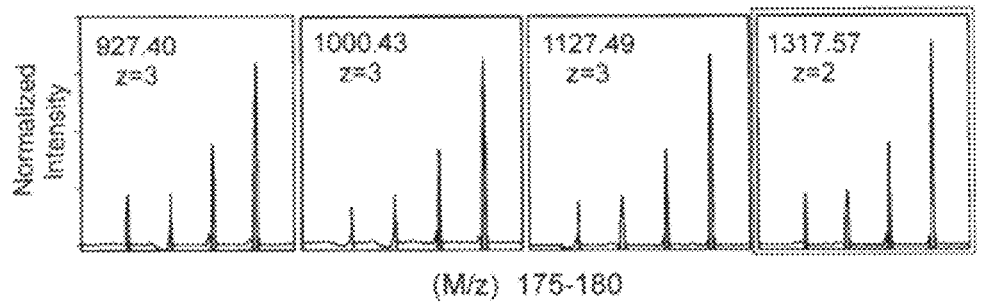

FIG. 2C shows the ratio of reporter ions (176-179) of several precursor ions on MS1 spectra.

The quaternary ammonium containing isobaric tags of the disclosure have a quaternary ammonium structure of the following general formula:

wherein A-D are organic groups. The quaternary ammonium containing isobaric tags typically have the following structure:

reporter group-balancer group-reactive group wherein, for purposes of glycan analysis, the reactive group is capable of conjugating with glycans. The quaternary ammonium containing isobaric tags according to the disclosure may have a wide variety of substituents on the nitrogen of the quaternary ammonium with the proviso that the reporter group and the balancer group are linked by an MS/MS scissionable bond.

The isotopes of the quaternary ammonium containing isobaric tags according to the disclosure can be incorporated into various positions and may be any of the known heavy isotopes.

By way of example, the quaternary ammonium structure may be represented as follows as a 6-plex reagent:

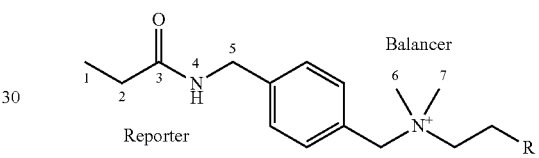

wherein heavy isotopes may be at any of positions 1-7, the reporter group and balancer group are linked by an MS/MS scissionable bond, and R is a reactive group capable of conjugating with glycans. The reactive group may be a primary amine capable of conjugating with glycans via reductive amination. The reactive group can also be aminooxy, hydrazide, or other groups that react with aldehyde. The isotopes may include $^{15}N$, $^{13}C$ and $^2H$. By way of further example, such structures may be any of the structures of the formula:

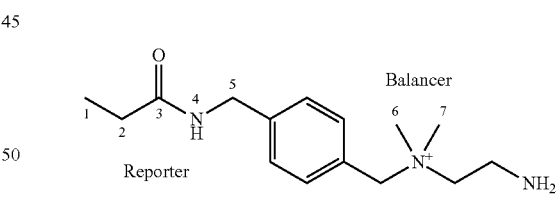

as shown in the following table (isotopes in bold):

|     | 1 | 2 | 3 | 4 | 5 | 6 | 7 |
|-----|---|---|---|---|---|---|---|
| 176 | $CH_3$ | $CH_2$ | C | N | $CH_2$ | $C^2H_3$ | $CH^2H_2$ |
| 177 | $CH_3$ | $CH_2$ | $^{13}C$ | N | $CH_2$ | $C^2H_3$ | $CH_2{}^2H$ |
| 178 | $^{13}CH_3$ | $^{13}CH_2$ | C | N | $CH_2$ | $C^2H_3$ | $CH_3$ |
| 179 | $^{13}CH_3$ | $^{13}CH_2$ | $^{13}C$ | N | $CH_2$ | $CH_3$ | $CH^2H_2$ |
| 180 | $^{13}CH_3$ | $^{13}CH_2$ | $^{13}C$ | $^{15}N$ | $CH_2$ | $CH_3$ | $CH_2{}^2H$ |
| 181 | $^{13}CH_3$ | $^{13}CH_2$ | $^{13}C$ | $^{15}N$ | $^{13}CH_2$ | $CH_3$ | $CH_3$ |

In a further aspect according to the disclosure, the quaternary ammonium containing isobaric tag reagent has the formula:

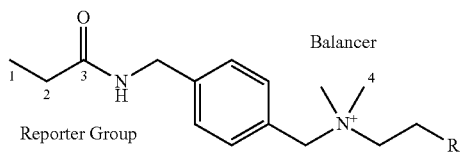

wherein at least one of positions 1-4 may comprise an isotope atom, the reporter group and balancer group are linked by an MS/MS scissionable bond, and R is the reactive group and is capable of conjugating with glycans. The reactive group may be a primary amine capable of conjugating with glycans via reductive amination. The reactive group can also be aminooxy, hydrazide, or other groups that react with aldehyde.

In one embodiment of the disclosure, a quaternary ammonium containing isobaric tag reagent is provided having the formula reporter group-balancer group-reactive group wherein the reagent has the structure (I):

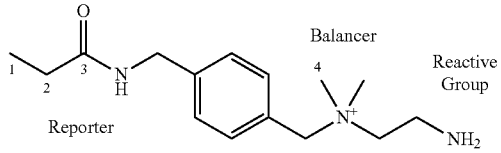

In such embodiment, the reporter group and balancer group are linked by an MS/MS scissionable bond, the reporter group has a molecular mass ranging from 176 to 179 Da, the reagent contains 2 or 3 isotope atoms independently selected from $^{13}C$ and $^2H$, and the reactive group comprises a reactive primary amine capable of conjugating with glycans via reductive amination.

In aspects of the disclosure, the quaternary ammonium containing isobaric tag reagents have the substituents shown in FIG. 1A. Thus, in embodiments according to structure (I), the methyl group at position 4 is $^{13}CHD_2$. In another embodiment, the methyl group at position 4 is $CHD_2$ and the carbon at position 3 is $^{13}C$. In another embodiment, the carbon at each of positions 1, 2 and 4 is $^{13}C$. In a further embodiment, the carbon at each of positions 1, 2 and 3 is $^{13}C$.

In a further aspect of the disclosure, a method of N-glycan analysis is provided comprising labeling N-glycans with a quaternary ammonium containing isobaric tag reagent comprising an MS/MS scissionable bond and a reactive group capable of conjugating with N-glycans. According to one aspect of the method, the quaternary ammonium containing isobaric tag reagent comprises the formula:

reporter group-balancer group-reactive group, wherein the reporter group and balancer group are linked by the MS/MS scissionable bond.

In other aspects of the method of N-glycan analysis according to the disclosure, the quaternary ammonium containing isobaric tag reagent comprises the formula:

reporter group-balancer group-reactive group, wherein the reagent has the structure:

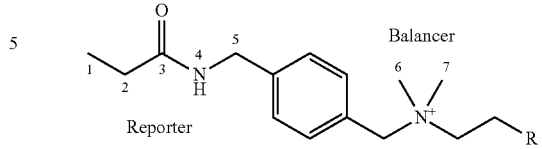

wherein heavy isotopes may be at any of positions 1-7, the reporter group and balancer group are linked by an MS/MS scissionable bond, and R is a reactive group capable of conjugating with glycans. The reactive group may be a primary amine capable of conjugating with glycans via reductive amination. The reactive group can also be aminooxy, hydrazide, or other groups that react with aldehyde. The isotopes may include $^{15}N$, $^{13}C$ and $^2H$.

In a further aspect of the method of glycan analysis according to the disclosure, the quaternary ammonium structure may be represented as follows:

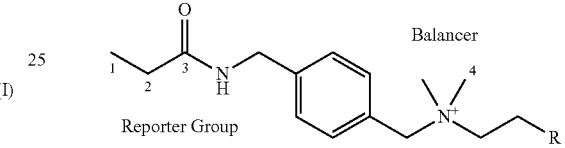

wherein at least one of positions 1-4 comprises an isotope atom, the reporter group and balancer group are linked by an MS/MS scissionable bond, and R is the reactive group and is capable of conjugating with glycans. In some embodiments, the reporter group has a mass in a range from 176 to 179 Da and the reagent contains 2 or 3 isotope atoms independently selected from $^{13}C$ and $^2H$. The quaternary ammonium containing isobaric tag reagents may, by way of example, have the substituents shown in FIG. 1A.

In other aspects of the method of N-glycan analysis according to the disclosure, the reactive group comprises a reactive primary amine capable of conjugating with glycans via reductive amination.

In other aspects of the method of N-glycan analysis according to the disclosure, the method further comprises quantitatively analyzing the labeled N-glycans.

In other aspects of the method of N-glycan analysis according to the disclosure, the N-glycans are obtained by
(a) immobilizing glycoproteins comprising N-glycans on a solid support;
(b) chemically modifying the N-glycans; and
(c) releasing the N-glycans from the solid support.

According to these aspects, proteins such as glycoproteins are conjugated to a solid support and the un-conjugated molecules may be washed away. The glycans on the immobilized glycoproteins are modified enzymatically or by chemical reactions. Then, the glycans are released from the solid support for analysis. In such aspects, the solid support may be any material known for such use, such as polymer beads or resin, or controlled pore glass beads.

In other aspects of the method of N-glycan analysis according to the disclosure, the glycoproteins are obtained from a biological sample such as human or nonhuman animal serum. As used herein, the term "biological sample" or "biological fluid" includes, but is not limited to, any quantity of a substance from a living or formerly living subject. Such substances include, but are not limited to, blood, serum, plasma, urine, cells, organs, tissues, bone, bone marrow, lymph, lymph nodes, synovial tissue, CSF, chondrocytes, synovial macrophages, endothelial cells, and skin. In a preferred embodiment, the fluid is blood or serum.

In other aspects of the method of N-glycan analysis according to the disclosure, the N-glycans carry sialic acids and the chemical modification of the N-glycans comprises carbodiimide coupling of the sialic acids.

In other aspects of the method of N-glycan analysis according to the disclosure, the quantitative analyzing step comprises fragmenting the reagent and quantitating the N-glycans.

In other aspects of the method of N-glycan analysis according to the disclosure, fragmenting the reagent comprises MS/MS scission of the MS/MS scissionable bond.

In other aspects of the method of N-glycan analysis according to the disclosure, Na+ is not used in quantitatively analyzing the labeled glycans.

The methods of the disclosure including a quantitative analyzing step preferably comprise fragmenting the reagents and quantitating the N-glycans, more preferably fragmenting the reagents using MS/MS. The methods of the disclosure for analysis of glycans may be performed without the use of $Na^+$ or other metals. Such Na+ is not needed in quantitative analysis according to the methods of the disclosure since the quaternary ammonium fragments as easy as glycosidic bonds in MS.

The disclosure additionally provides a method of making a quaternary ammonium containing isobaric tag reagent comprising the steps of:
(a) reacting Boc-(4-(aminomethyl)benzyl)-amine and triethylamine with 2-nitrobenzenesulfonyl chloride to obtain a first reaction product;
(b) reacting the first reaction product with sodium carbonate and methyl iodide to obtain a second reaction product;
(c) reacting the second reaction product with β-mercaptoacetic acid to obtain a third reaction product;
(d) reacting the third reaction product with a first intermediate reaction product of a carboxybenzyl-protected 3-amino-1,2-propanediol and sodium periodate to form a fourth reaction product;

(e) removing the tert-butyloxycarbonyl (Boc) protecting group from the fourth reaction product;
(f) reacting the deprotected fourth reaction product with a second intermediate reaction product of propionic acid, 1-ethyl-3-(3-dimethylaminopropyl)carbodiimide and N-hydroxysuccinimide to form a fifth reaction product;
(g) reacting the fifth reaction product with methyl iodide to obtain a crude final product; and
(h) removing the carboxybenzyl (Cbz) protecting group from the crude final product to obtain the quaternary ammonium-containing isobaric tag reagent;
wherein the propionic acid and methyl iodide are selected from one of the following reactant pairs (i)-(iv) comprising isotope labeled reactant:
  (i) isotope-unlabeled propionic acid of the formula $CH_3CH_2COOH$, and isotope-labeled methyl iodide of the formula $^{13}CHD_2I$;
  (ii) isotope-labeled propionic acid of the formula $CH_3CH_2{}^{13}COOH$, and isotope-labeled methyl iodide of the formula $CHD_2I$;
  (iii) isotope-labeled propionic acid of the formula $^{13}CH_3{}^{13}CH_2COOH$, and isotope-labeled methyl iodide of the formula $^{13}CH_3I$; and
  (iv) isotope-labeled propionic acid of the formula $^{13}CH_3{}^{13}CH_2{}^{13}COOH$, and isotope-unlabeled methyl iodide of the formula $CH_3I$.

The advantages and features of the invention are further illustrated with reference to the following examples, which are not to be construed as in any way limiting the scope of the invention but rather as illustrative of one embodiment of the invention in a specific application thereof.

EXAMPLES

Example 1, Synthesis of QUANTITY

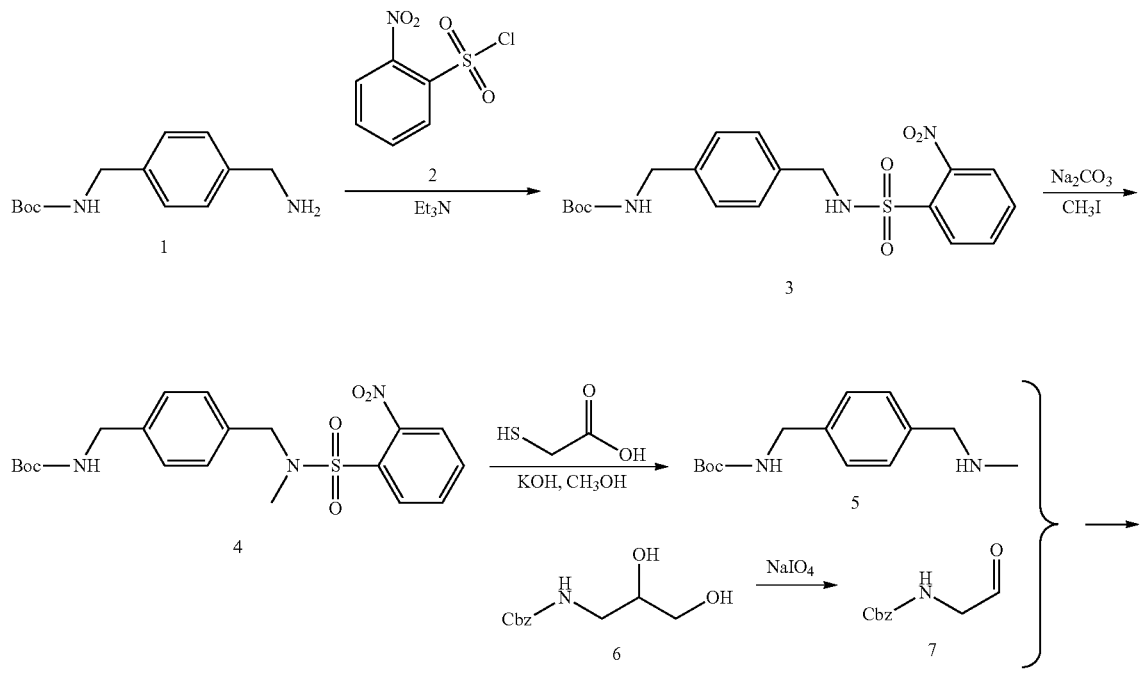

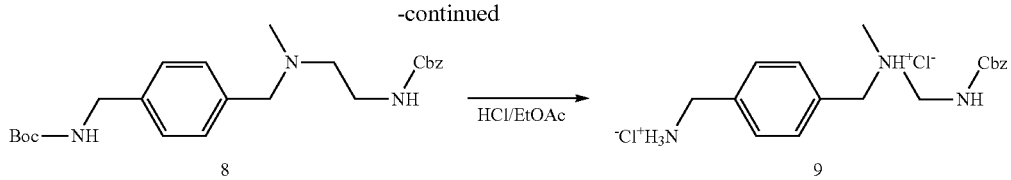

Boc-(4-(aminomethyl)benzyl)-amine (1, 1.12 g, 4.75 mmol) and 1.5 mL triethylamine (10.8 mmol) were mixed in 30 mL dichloromethane (DCM), then 2-nitrobenzenesulfonyl chloride (2, 1 g, 4.52 mmol) was added. The reaction was stirred under argon balloon for overnight. After reaction was done, 30 mL more DCM was added. The mixture was washed with 50 mL HCl (50 mmol/L) solution twice, 50 mL saturated NaHCO$_3$ solution twice, and 50 mL brine solution once. The organic layer was dried with anhydrous Na$_2$SO$_4$ and removed by Rotavap to offer 1.7 g white solid (3, 4.03 mmol, 89% yield). $^1$H-NMR (CDCl$_3$, 400 MHz) δ 7.60-8.00 (m, 4H), 7.10-7.20 (m, 4H), 4.28 (s, 2H), 4.22 (d, J=6.0 Hz, 2H), 1.45 (s, 9H). $^{13}$C-NMR (CDCl$_3$, 101 MHz) δ 155.88, 147.77, 139.01, 134.79, 133.92, 133.47, 132.75, 131.00, 128.15, 127.61, 125.22, 79.59, 47.54, 44.13, 28.41. ESI-MS (M+H)$^+$=422.14, Cal. (M+H)$^+$=422.14.

Compound 3 (1.7 g, 4.40 mmol) was dissolved in 10 mL DMF and 2.8 g Na$_2$CO$_3$ (26.4 mmol) solid was added. 1.37 mL methyl iodide (22 mmol) was then added. The reaction was stirred in dark for 2 hours. The reaction was checked by HPLC for completion. After reaction was done, most CH$_3$I and DMF was removed by Rotavap. The residue was dissolved in 50 mL EtOAc and 50 mL brine solution. The organic layer was separated and washed by 60 mL brine solution three times, dried over Na$_2$SO$_4$ and removed by Rotavap to offer 1.8 g yellowish solid (4, 4.13 mmol, 94% yield). $^1$H-NMR (CDCl$_3$, 400 MHz) δ 7.60-8.00 (m, 4H), 7.23-7.30 (m, 4H), 4.39 (s, 2H), 4.30 (d, J=6.0 Hz, 2H), 2.76 (s, 3H), 1.45 (s, 9H). $^{13}$C-NMR (CDCl$_3$, 101 MHz) δ 155.91, 148.25, 138.98, 134.40, 133.61, 132.36, 131.63, 131.02, 128.57, 127.79, 124.17, 79.59, 53.70, 44.28, 34.09, 28.41. ESI-MS (M+H)$^+$=436.13, Cal. (M+H)$^+$=436.14.

Compound 4 (2.56 g, 5.89 mmol) was dissolved in 200 mL 0.5 mol/L KOH/CH$_3$OH solution. 1 mL β-mercaptoacetic acid (14.4 mmol) was added. The reaction was stirred under argon balloon for overnight. After the reaction was done, there was white precipitation in the reaction mixture. After the precipitation was filtered out, methanol was removed carefully by Rotavap. The residue was added with 120 mL water and extracted with 40 mL EtOAc three times. The pooled organic layer was washed by 120 mL saturated NaHCO$_3$ solution once, brine solution 120 mL once. The organic layer was dried over Na$_2$SO$_4$ and removed by Rotavap to offer 1.0 g light yellow solid (5, 4 mmol, 68% yield). $^1$H-NMR (CDCl$_3$, 400 MHz) δ 7.22-7.30 (m, 4H), 4.29 (d, J=6.0 Hz, 2H), 3.73 (s, 2H), 2.44 (s, 3H), 1.46 (s, 9H). $^{13}$C-NMR (CDCl$_3$, 101 MHz) δ 155.90, 139.02, 137.72, 128.47, 127.57, 79.59, 55.61, 44.43, 35.86, 28.42. ESI-MS (M+H)$^+$=251.17, Cal. (M+H)$^+$=251.18.

Compound 6 [please identify] (1.8 g, 8 mmol) was dissolved in 100 mL H$_2$O and 2.56 g NaIO$_4$ (12 mmol) was then added. The reaction was stirred for 1 h, extracted with 40 mL DCM three times. The organic layer was washed with 80 mL brine solution once, dried over Na$_2$SO$_4$, and removed by Rotavap. The resulting compound 7 was used without purification for next reaction.

Compound 5 (1 g, 4 mmol) was dissolved in 12 mL MeOH and 400 μL glacial acetic acid was added. 620 mg NaCNBH$_3$ (10 mmol) was dissolved in 4 mL MeOH and added slowly. Then, freshly prepared compound 7 was dissolved in 4 mL MeOH and added into the mixture slowly. The reaction was stirred at room temperature for 1 h. After reaction was done, most MeOH was removed by Rotavap. The residue was added with 20 mL half saturated NaHCO$_3$ solution, extracted with 20 mL EtOAc three times. The pooled organic layer was washed with 20 mL brine solution once, dried over Na$_2$SO$_4$ and removed by Rotavap to offer 1.54 g oily crude compound 8 (3.6 mmol, 90% yield) $^1$H-NMR (CDCl$_3$, 400 MHz) δ 7.30-7.40 (m, 5H), 7.10-7.25 (m, 4H), 5.10 (s, 2H), 4.29 (s, 2H), 3.45 (s, 2H), 3.28 (t, J=2.0 Hz, 2H), 2.48 (t, J=2.0 Hz, 2H), 2.19 (s, 3H), 1.45 (s, 9H). $^{13}$C-NMR (CDCl$_3$, 101 MHz) δ 156.47, 155.94, 137.69, 136.68, 135.80, 129.31, 129.22, 128.61, 128.57, 128.53, 128.20, 128.10, 128.05, 127.48, 79.59, 67.53, 66.64, 55.79, 44.40, 41.70, 38.32, 28.43. ESI-MS (M+H)$^+$=428.26, Cal. (M+H)$^+$=428.25.

Figure 3:
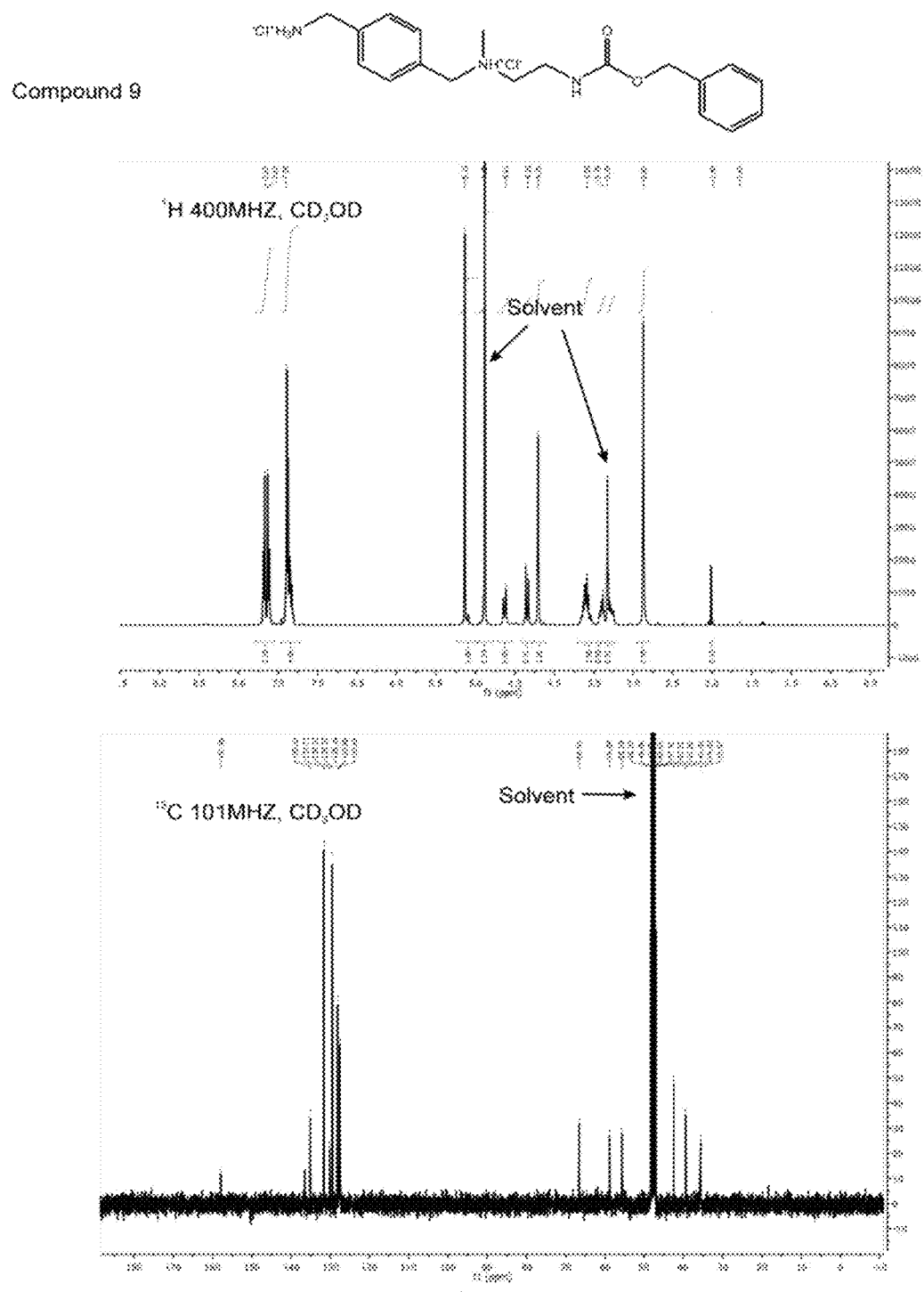
FIG. 3 is $^1H$ and $^{13}C$ spectra of compound 9 as described in Example 1.

Compound 8 (1.54 g) was added with 5 mL DCM and 5 mL trifluoroacetic acid (TFA), incubated for 1 hour. The solvent was removed by Rotavap. 25 mL HCl solution (50 mmol/L) was added. The aqueous layer was washed with 30 mL ether three times. 20 mL saturated K$_2$CO$_3$ solution was then added to adjust pH ~11. The aqueous layer was extracted with 30 mL EtOAc three times. The organic layer was washed with 30 mL brine solution once, dried over Na$_2$SO$_4$ and removed by Rotavap. The resulting oily product was added with 12 mL 1 mol/L HCl/EtOAc solution. Precipitation was immediately visible. Solvent was removed by Rotavap to offer light yellowish compound 9 (1.0 g, 70% yield) (FIG. 3), which was the key intermediate for the synthesis of all isotope labeled QUANTITY. $^1$H-NMR (CD$_3$OD, 400 MHz) δ 7.55-7.70 (m, 4H), 7.30-7.41 (m, 5H), 5.13 (s, 2H), 4.63 (d, J=13.2 Hz, 1H), 4.35 (d, J=13.2 Hz, 1H), 4.20 (s, 2H), 3.60 (m, 2H), 3.35 (m, 2H), 2.87 (s, 3H). $^{13}$C-NMR (CD$_3$OD, 101 MHz) δ 157.8, 135.17, 131.71, 130.22, 129.57, 128.16, 127.80, 127.63, 66.61, 58.89, 55.59, 42.41, 39.42, 35.57. ESI-MS (M+H)$^+$=328.20, Cal. (M+H)$^+$=328.20.

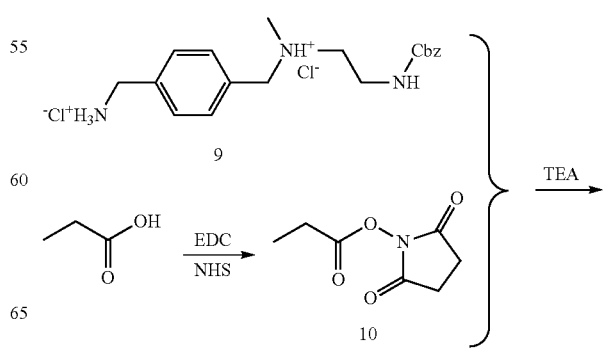

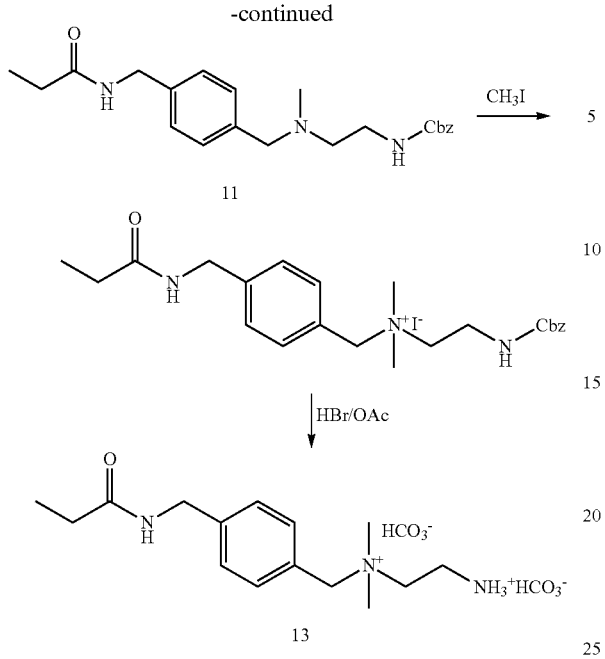

Figure 4:
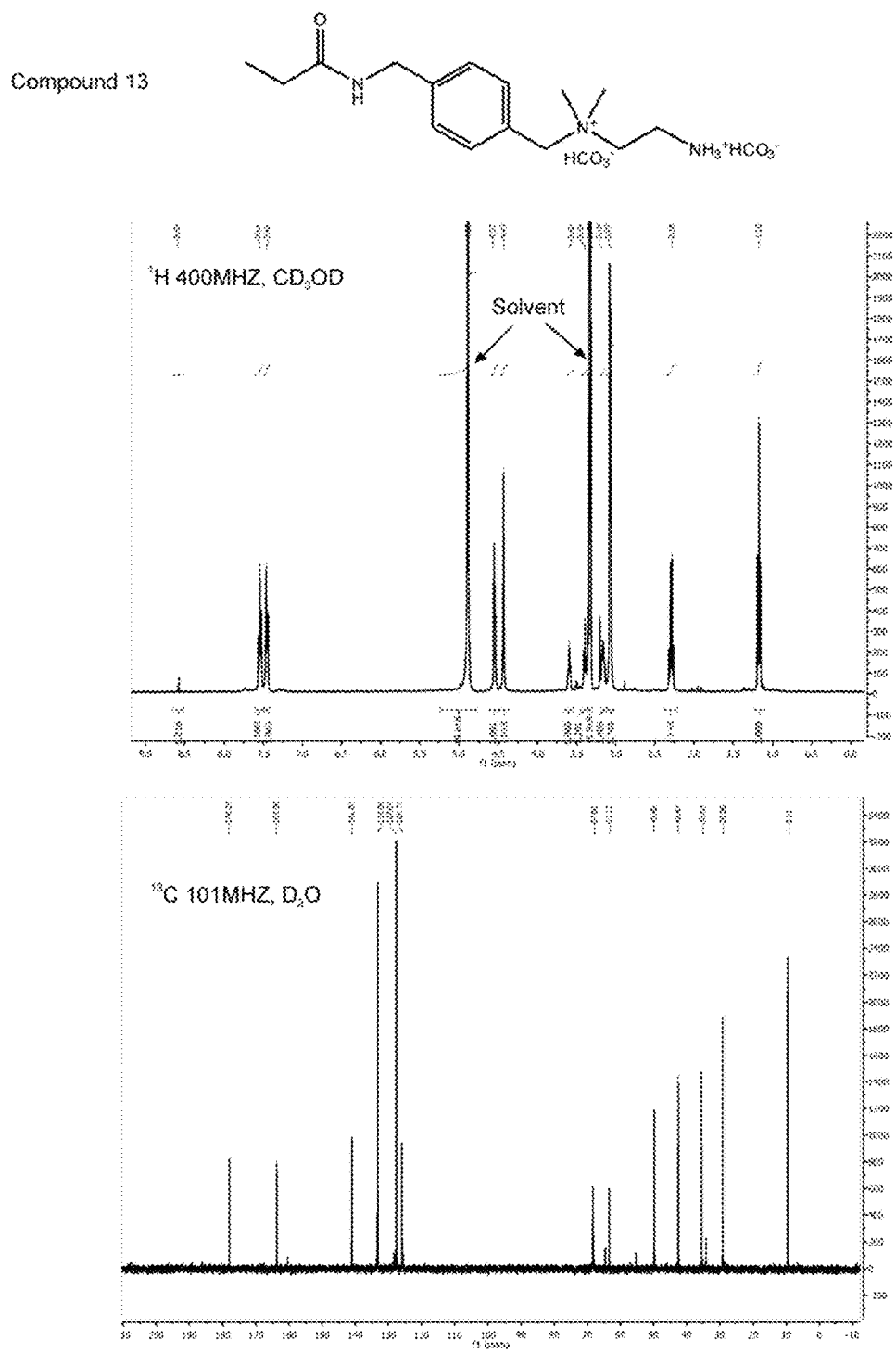
FIG. 4 is $^1H$ and $^{13}C$ spectra of compound 13 as described in Example 1.
Figure 5A:
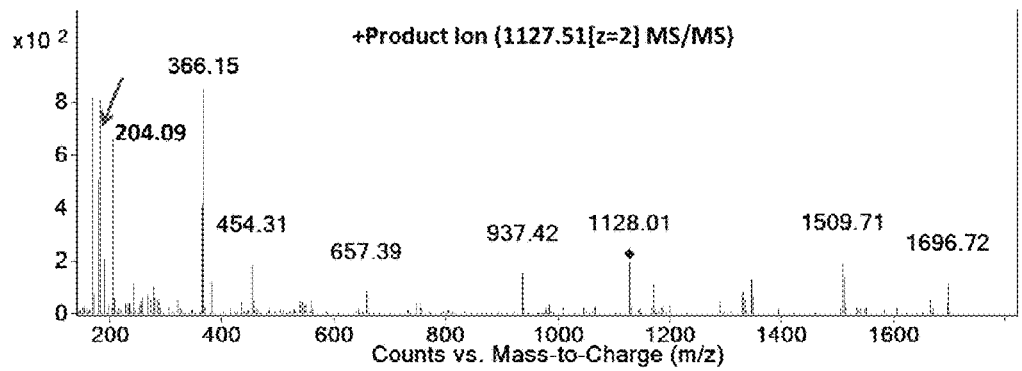
FIG. 5A-FIG. 5J are representative MS/MS spectra of labeled N-glycans according to aspects of the disclosure. Peaks for the reporter ions (176, 177, 178, 179) are indicated with an arrow.
Figure 5B:
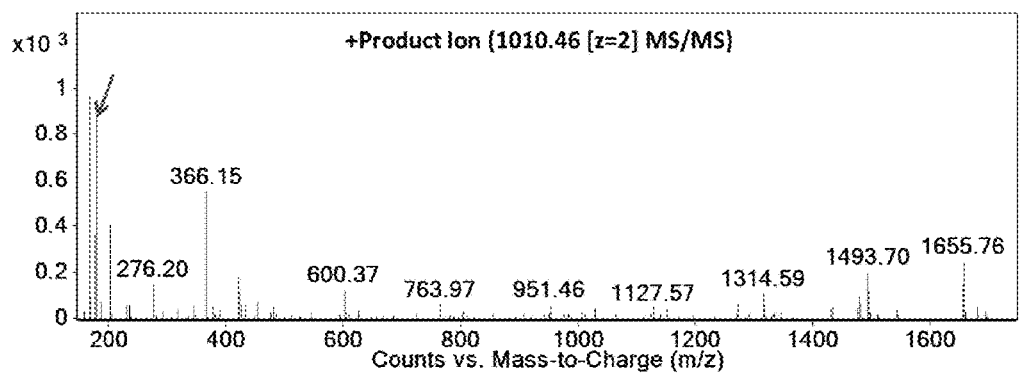
Figure 5C:
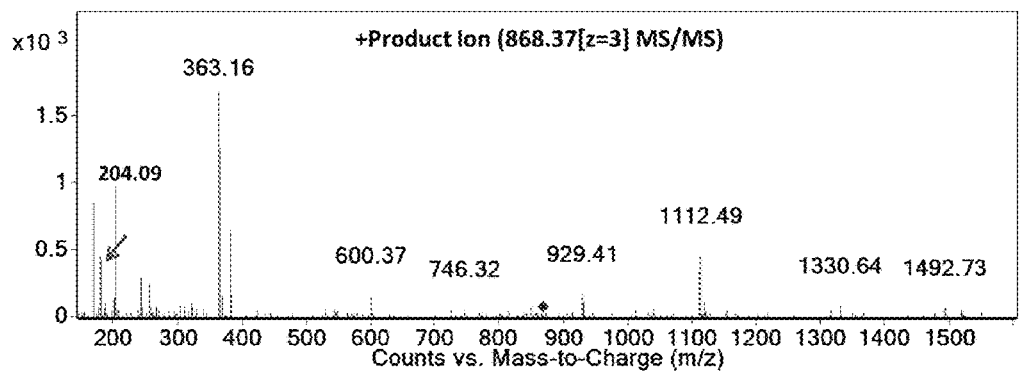
Figure 5D:
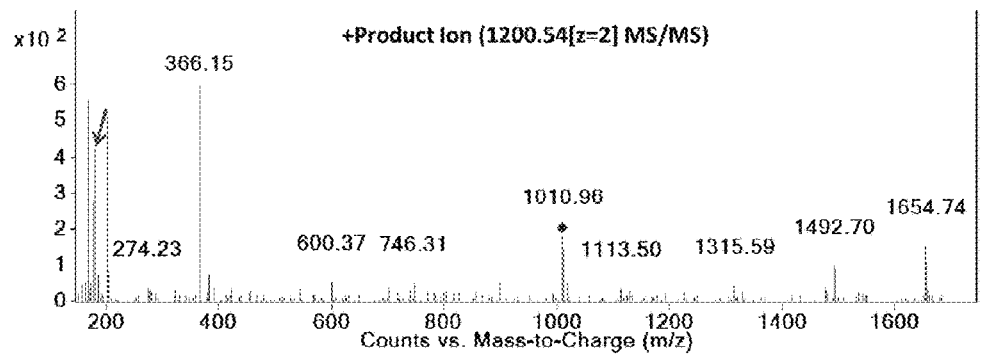
Figure 5E:
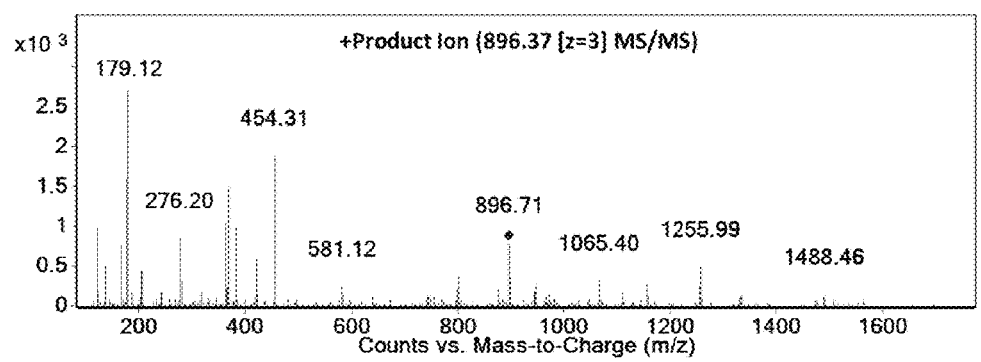
Figure 5F:
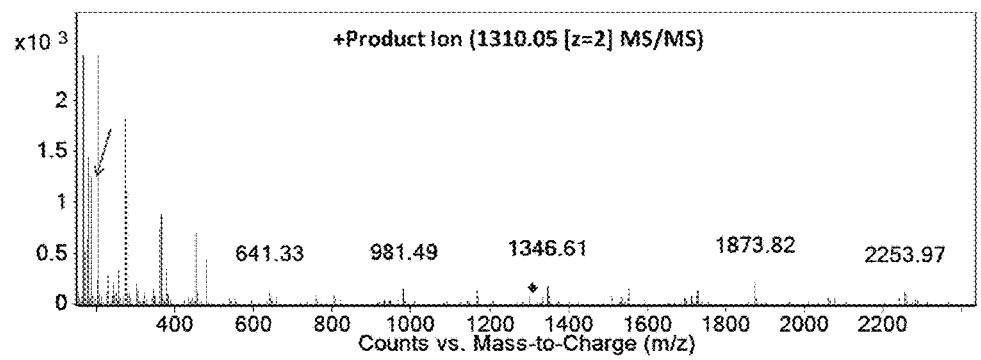
Figure 5G:
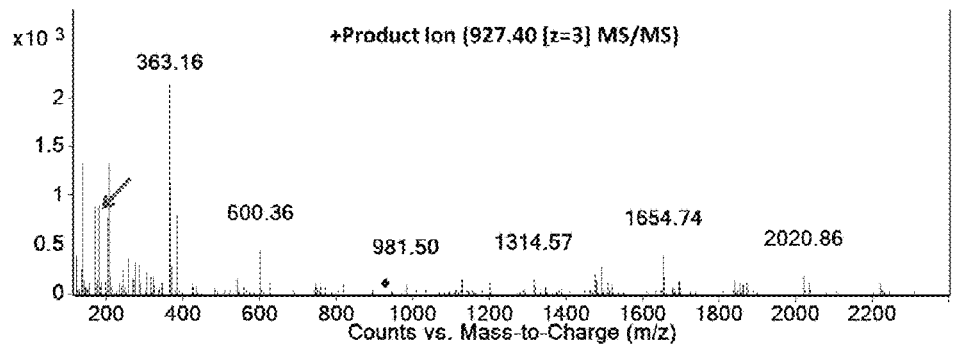
Figure 5H:
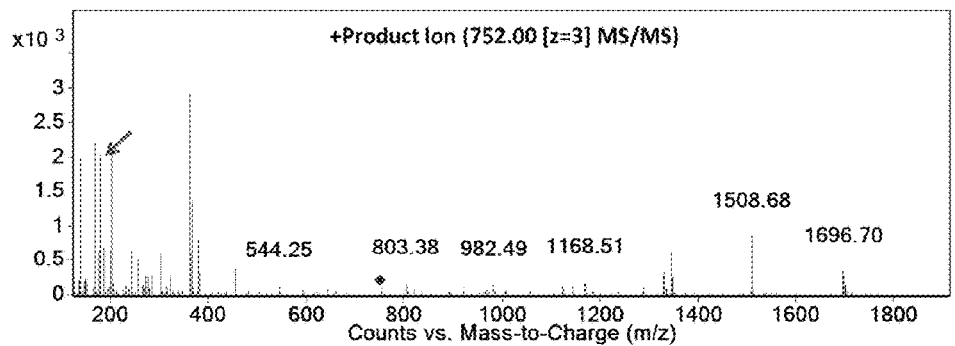
Figure 5I:
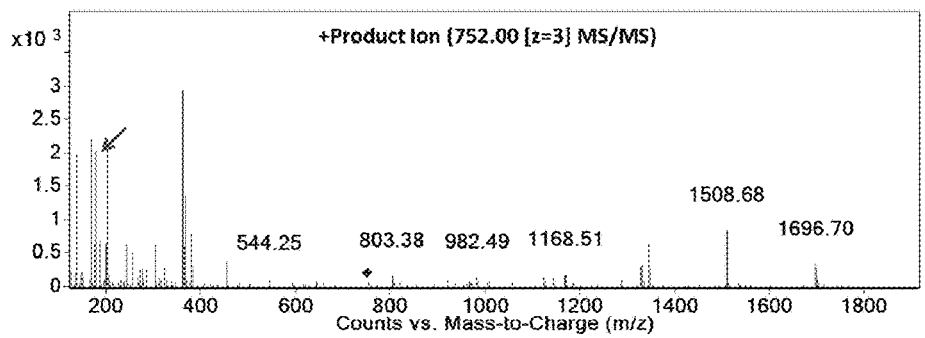
Figure 5J:
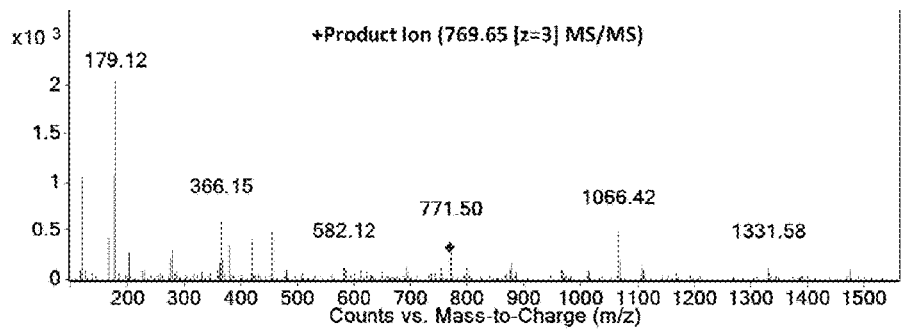

0.57 g (compound 13, 59% yield) (FIG. 4). For non-labeled compound 13, $^1$H-NMR (CD$_3$OD, 400 MHz) δ 7.40-7.60 (m, 4H), 4.55 (d, J=4 Hz, 2H), 4.43 (s, 2H), 3.60 (t, J=6.8 Hz, 1H), 3.39 (t, J=6.8 Hz, 1H), 3.16 (t, J=6.8 Hz, 2H), 3.07 (d, J=4.8 Hz, 6H), 2.29 (q, J=7.6 Hz, 2H), 1.17 (t, J=7.6 Hz, 3H). $^{13}$C-NMR (D$_2$O, 101 MHz) δ 178.10, 163.76 (HCO$_3$ counterion), 141.05, 133.20, 127.57, 125.85, 68.30, 63.40, 49.79, 42.47, 35.45, 29.14, 9.55. ESI-MS (M+H)$^+$=264.20, Cal. (M+H)$^+$=264.21.

The synthesis of isotope labeled QUANTITY was the same as that of unlabeled compound 13, but started from the following four pairs of isotope labeled molecules: (CH$_3$CH$_2$COOH, $^{13}$CHD$_2$I); (CH$_3$CH$_2$$^{13}$COOH, CHD$_2$I); ($^{13}$CH$_3$$^{13}$CH$_2$COOH, $^{13}$CH$_3$I); ($^{13}$CH$_3$$^{13}$CH$_2$$^{13}$COOH, CH$_3$I).

Example 2

Synthesis of Quaternary Ammonium Containing Isobaric Tags with Fluorescent Tag and Reactive Group

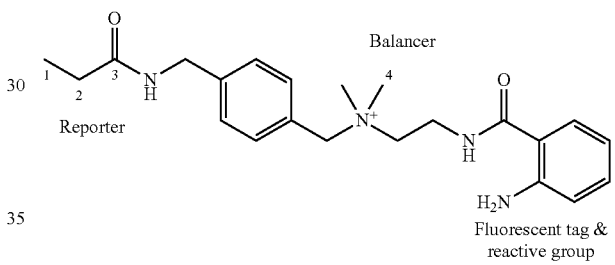

240 μL propionic acid (3.1 mmol) was dissolved in 20 mL DCM. 760 mg 1-Ethyl-3-(3-dimethylaminopropyl) carbodiimide (EDC, 4 mmol) and 400 mg N-Hydroxysuccinimide (NHS, 3.5 mmol) were added. The reaction was stirred for 1 hour, then the solvent was washed by 40 mL water three times and removed by Rotavap to offer compound 10, which was used without purification. Crude compound 10 was mixed with 1.0 g compound 9 (2.5 mmol) in 20 mL anhydrous DMF and 1.65 mL TEA (triethylamine) [please confirm] (6.3 mmol) was added. The reaction was stirred for 1 hour until compound 9 was completely consumed. Most DMF were removed by Rotavap. The residue was dissolved in 50 mL EtOAc, washed with 60 mL half saturated NaHCO$_3$ solution three times, 60 mL brine once. The organic layer was dried over Na$_2$SO$_4$ and removed by Rotavap to offer compound 11, which was used without further purification. For non-labeled compound 11, $^1$H-NMR (CDCl$_3$, 400 MHz) δ 7.30-7.40 (m, 5H), 7.17-7.27 (m, 4H), 5.09 (s, 2H), 4.41 (d, J=6 Hz, 2H), 3.47 (s, 2H), 3.28 (m, 2H), 2.49 (m, 2H), 2.23 (q, J=8.0 Hz, 2H), 2.18 (s, 3H), 1.17 (t, J=8.0 Hz, 3H). $^{13}$C-NMR (CDCl$_3$, 101 MHz) δ 173.59, 156.42, 138.00, 137.30, 136.69, 129.28, 128.53, 128.10, 127.84, 66.60, 61.94, 55.81, 43.34, 41.77, 38.34, 29.70, 9.88. ESI-MS (M+H)+=384.23, Cal. (M+H)+=384.23.

Crude compound 11 from last step was dissolved in 20 mL anhydrous DMF. 439 μL CH$_3$I (7 mmol) and 1.0 g Na$_2$CO$_3$ were added. The reaction was stirred for 2 hours. Once the reaction was completed, DMF was removed by Rotavap. The solid was washed with 20 mL acetonitrile twice. The pooled organic layer was removed by Rotavap to give crude compound 12, which was added with 20 mL HBr/HOAc and incubated for 1 h. HBr/HOAc was then removed in Rotavap. The residue was dissolved in 20 mL water, washed with 20 mL ether twice, and purified by SCX column (solvent A: 25% acetonitrile, solvent B: 25% acetonitrile, 1 mol/L NH$_4$HCO$_3$). The collected fractions were pooled together and lyophilized. The residual solid was lyophilized in H$_2$O multiple times to remove NH$_4$HCO$_3$ until the weight became constant. The final white solid was 1) Fluorescent Quantity (FluorQ)

Quaternary ammonium containing isobaric tag reagents can also be coupled with 2-aminobenzoic acid (2-AB) to form bifunctional reagents (FluorQ) that contain both isobaric tags and fluorescent tags. These reagents are fully compatible with traditional fluorescence detection of 2-AA/2-AB labeled glycans, but confer additional benefits like improved sensitivity and concurrent quantification of four samples. The synthesis of FluorQ is described below.

271.0 mg 2-(((benzyloxy)carbonyl)amino)benzoic acid (1.00 mmol) and N-Hydroxysuccinimide 143.75 mg (1.25 mmol) is dissolved in 20 mL dichloromethane. 1-Ethyl-3-(3-dimethylaminopropyl) chloride 286.5 mg (1.5 mmol) is then added and the reaction mixture is stirred under argon gas for 4 hours. The solution is washed with 20 mL water three times. The organic layer is dried with anhydrous sodium sulfate then removed. The residue is immediately dissolved in 20 mL N,N'-dimethylformamide (DMF) containing 195 mg Compound 13 (0.5 mmol). 0.35 mL N,N-diisopropylethylamine (DIPEA, 2.0 mmol) is added and the reaction is stirred for 2 hours. After DMF is removed, the residue is purified with C18 column by using a gradient of solvent A (0.1% TFA in water) and solvent B (0.1% TFA in acetonitrile). The lyophilized Compound 14 is dissolved in 10 mL methanol, added with 20 mg Pd—C, then is deprotected under hydrogen gas for 4 hours to offer FluorQ reagent. Isotope labels may be included as described herein.

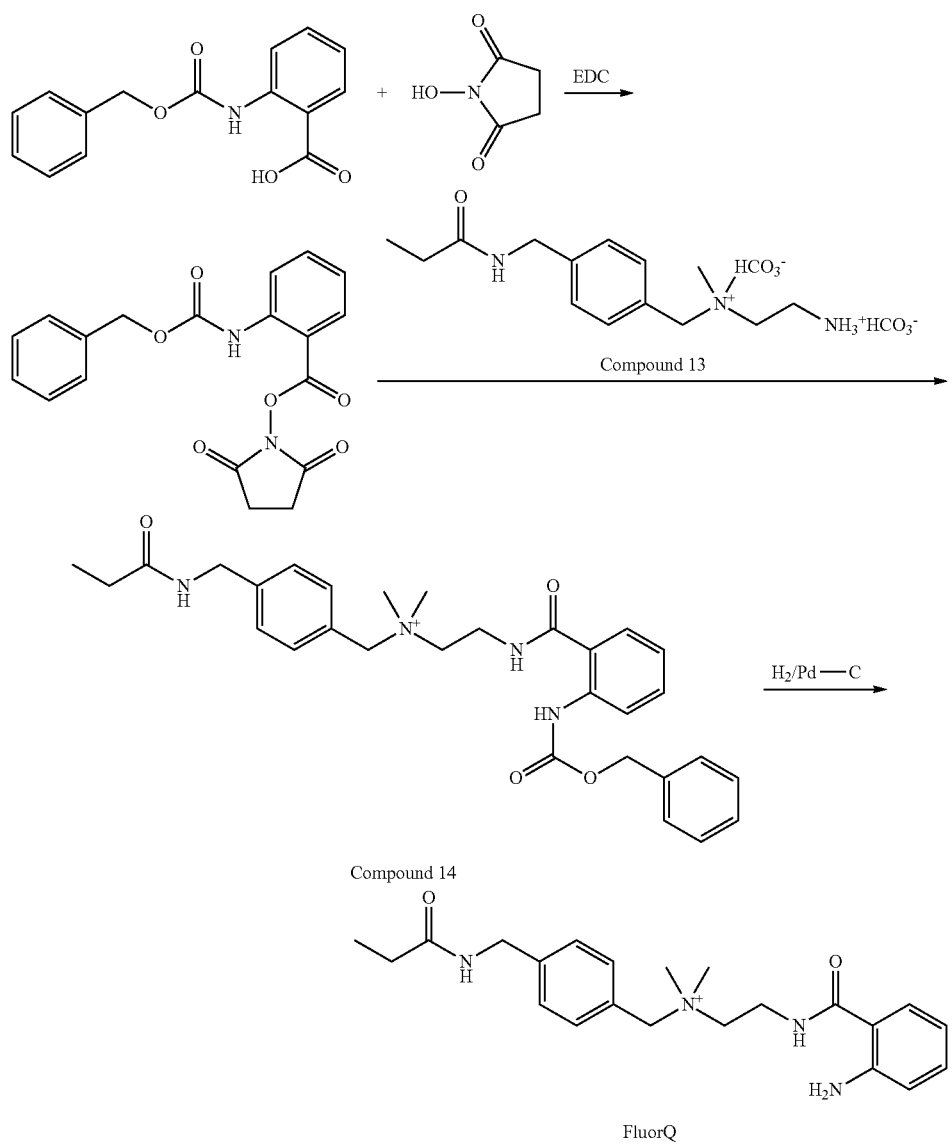

Compound 14

FluorQ

Example 3

Serum Glycan Labeling Protocol

Materials and Reagents

Spin columns (snap cap) and AminoLink™ resin were purchased from Pierce (Thermo Fisher Scientific Inc.; Rockford, Il); Carbograph™ was purchased from Grace (Deerfield, Ill.). Peptide-N-glycosidase F (PNGase F), denaturing buffer, and reaction buffer G7 were from New England Biolabs (Ipswich, Mass.). Human sera were collected from healthy men with the approval of the Institutional Review Board of Johns Hopkins University and pooled for use. All other chemicals were purchased from Sigma unless specified.

N-Glycan Enrichment

Serum proteins were conjugated to Aminolink™ resin using reductive amination. The detailed protocols for protein conjugation, sialic acid derivatization, and reducing isobaric tag labeling have been described in previous papers. Yang, S.; Li, Y.; Shah, P.; Zhang, H., Anal. Chem. 2013, 85, 5555-5561; Shah, P.; Yang, S.; Sun, S.; Aiyetan, P.; Yarema, K. J.; Zhang, H., Anal. Chem. 2013, 85, 3606-3613; Yang, S.; Yuan, W.; Yang, W.; Zhou, J.; Harlan, R.; Edwards, J.; Li, S.; Zhang, H., Anal. Chem. 2013, 85, 8188-8195.

20 μL serum proteins were first denatured in 200 μL solution consisting of 20 μL denaturing buffer (10×) and 160 μL buffer (pH 10.0; 40 mmol/L sodium citrate and 20 mmol/L sodium carbonate) for 10 minutes at 100° C. After pre-conditioning of Aminolink™ resin (200 μL) with pH 10 buffer, the denatured proteins were added to Aminolink™ resin in 300 μL buffer (pH 10.0) and incubated at room temperature for 4 h with mixing. 50 μL of 500 mmol/L sodium cyanoborohydride (1×PBS) was added to incubate for another 4 h. After rinsing the resin with 500 μL of 1×PBS (pH 7.4) twice, samples were reduced with 50 mmol/L sodium cyanoborohydride (NaCNBH$_3$) in 1×PBS for 4 h.

The beads conjugated with proteins were washed with 1 mol/L Tris-HCl (500 μL, pH 7.6) twice and the remained aldehyde sites were blocked with 500 μL of 1 mol/L Tris-HCl in the presence of 50 mmol/L NaCNBH$_3$ (0.5 h).

The beads were washed three times with 400 µL of 1 mol/L NaCl and three times with H$_2$O. To stabilize sialic acids residues, glycans on solid support were incubated with 465 µL of p-toluidine (Sigma) solution (pH 4-6), which consists of 400 µL p-toluidine, 25 µL 36-38% HCl, and 40 µL EDC (N-(3-dimethylaminopropyl)-N'-ethylcarbodiimide; 5.6 mol/L; Sigma). Reaction was preceded for 3 h at room temperature before the chemicals were washed off from the solid support with 400 µL of 1% formic acid (twice), 400 µL of 10% acetonitrile (twice), 400 µL of 1 mol/L NaCl (twice) and finally H$_2$O (twice). N-glycans were released with 160 solution consisting of 4 µL PNGase F (New England Bio-Labs), 16 µL 10× G7 buffer, 146 µL water, incubation at 37° C. for at least 2 h. The eluted glycans were purified by Carbograph™ prior to being dried in vacuum. Yang, S. J.; Zhang, H., *Anal. Chem.* 2012, 84, 2232-2238.

N-Glycan Labeling

The dried serum glycans were re-suspended in 80 µL of solution mixture consisting of dimethyl sulfoxide (DMSO) and acetic acid (AA) (7:3, vol) in the presence of 1 mol/L NaCNBH$_3$. Samples were divided to four vials with a ratio of 1:1:2:4 (or 10:10:20:40 µL). 40 µL of 100 mmol/L QUANTITY (176, 177, 178, and 179) dissolved in the mixture of DMSO and AA (7:3) were added into each sample respectively and incubated at 65° C. for 4 h. The reaction was quenched by addition of 2 mL water and 2 µL concentrated formic acid.

Samples that were labeled with 4-plex QUANTITY were pooled for cleanup by Carbograph™. The purified samples were dissolved in 400 µL of 0.2% formic acid.

MS Analysis Method

LC-MS experiments were performed on an Agilent 1260 infinity HPLC-Chip cube nanospray interfaced to an Agilent 6550 Q-TOF MS. The HPLC-Chip consisted of a 160 nL enrichment trap column and a 75 µm×150 mm analytical column (5 µm, Zorbax® 300SB). Mobile phases were: (A) nano pure water with 0.1% formic acid and (B) acetonitrile with 0.1% formic acid. A 65 min-long gradient method was used for the LC separation. Sample loading onto the enrichment column was done at 1% B. The gradient used for the analytical column began at 1% B, was raised to 40% B at 35 min, and increased to 85% B at 42 min, maintained at 85% B until 48 min, and then brought back to 1% B at 55 min and equilibrated for 10 min before next run. Sample were loaded at 4 µL/min flow rate and eluted at 0.35 µL/min. Q-TOF was operated in high resolution positive ion mode. The key MS parameters were: source temperature 225° C., capillary voltage 1900 V, fragmentor voltage 155 V, drying gas flow rate 13 L/min. Data was acquired between m/z 100-3000 at a scan rate of 4 spectra/sec in MS mode and 5 spectra/sec in MS/MS mode. Ramped collision energy were applied with the slope setting of 4, offset setting of 3 for doubly charged ions; with slope of 2, offset of 2 for triply or higher changed ions. System control was achieved using Agilent Mass-Hunter data acquisition software and data analysis was performed with MassHunter qualitative analysis (B.06.00). Glycan identification was performed using GlycoWorkbench software (version 2.0). Representative MS2 spectra of labeled N-glycans are provided in FIG. 5A-J. The large fragments on these spectra are useful for glycan structure identification and reporter ions (176, 177, 178 and 179) indicated by an arrow are used for glycan quantification.

Example 4

Glycan Enrichment Using Glycoprotein Immobilization for Glycan Extraction (GIG)

Materials and Reagents

Sialylglycopeptide (SGP) was purchased from Fushimi Pharmaceutical Co., Ltd. (Marugame, Kagawa, Japan). Spin columns (snap cap), AminoLink™ resin, aminoxyT-MTzero™, and Zeba™ desalting columns were purchased from Pierce (Thermo Fisher Scientific Inc.; Rockford, Ill.); Carbograph™ was purchased from Grace (Deerfield, Ill.). Peptide-N-glycosidase F (PNGase F), denaturing buffer, and reaction buffer G7 were from New England BioLabs (Ipswich, Mass.). F12K (500 mL), FBS (50 mL), NEAA (5 mL), L-glutamine (5 mL), and Blasticidin are purchased from Life Technologies (Frederick, Md.). Fetuin from fetal bovine serum, p-Toluidine (pT), 2,5-dihydroxybenzoic acid (DHB), and N,N-dimethylaniline (DMA) were purchased from Sigma-Aldrich (St. Louis, Mo.); µ-Focus MALDI plate and its holder were from Hudson Surface Technology (Forte Lee, N.J.); Axima Resonance MALDI QIT-TOF mass spectrometry was from Shimadzu Biotech (Columbia, Md.). Human sera were collected from healthy men with the approval of the Institutional Review Board of Johns Hopkins University and pooled for use. All other chemicals were purchased from Sigma unless specified otherwise.

Wild-Type, ST6Gal1 Knockin, and ST3Gal4 Knockdown of Chinese Hamster Ovary (CHO) Cell Lines CHO-K1 cells were purchased from Life Technologies. All cell lines were grown in F12-K medium (Gibco) supplemented with 10% fetal bovine serum (FBS) (Life Technologies) in a humidified 37° C. incubator with 5% CO$_2$. Cells were seeded into a 6-well plate at appropriate densities and transfected 24 h later using Lipofectamine® 2000 (Life Technologies), according to the manufacturer's instruction.

Stable single clones were screened using select drugs, followed by lectin blot to evaluate the effect of glycosyltransferase expression. As for ST6 plasmid: ST6Gal1 (PubMed Gene ID: 6480) cDNA was purchased from OriGene and subcloned into pEF6/V5-his TOPO TA. For ST3Gal4: there are 6 members in ST3 family, the inventors used Crisper to target ST3Gal4 gene in this family.

Before starting the protocol, cell media, PBS, and trypsin were placed in a 37° C. humidified oven. The sterile dishes (10 cm in diameter) were used for cell culture. Cells were quickly thawing in 37° C. water bath. Cells were transferred to 10 cm sterile dish and washed with F12-K (10% FBS, 1% NEAA, and 1% L-glutamine; (note, add blasticidin (250 µg in 500 mL F12-K) only for ST6Gal1). Cells were washed using 10 mL 1×PBS (6×) before being collected for cell lysate.

Protein Immobilization and Sialic Acid Derivatization

Cells were first sonicated for 30 s in RIPA buffer at an interval of 30 s on ice for a total of 3 minutes. The RIPA buffer (Life Technologies) of proteins was exchanged with pH 10 buffer using Zeba™ desalting column (Thermo). Protein concentration was measured by NanoDrop Lite Spectrophotometer (Thermo). Proteins or peptides were conjugated to beads using reductive amination. For SGP (1 mg), 200 µL of AminoLink™ resin (500 µL of 50% slurry) was incubated with sample in 500 µL buffer (pH 10.0) (100 mM sodium citrate and 50 mM sodium carbonate) at room temperature for 4 h with mixing. Then 50 µL of 500 mM NaCNBH$_3$ in DI was added to incubate for another 4 h. After rinsing the resin with 500 µL of 50 mM phosphate buffer (1× pH 7.4) twice, sample on beads were further reduced by adding 50 mM NaCNBH$_3$ in 50 mM PBS at room temperature for 4 h with mixing. After incubation, the beads were washed with 1 M Tris-HCl (500 µL, pH 7.6) twice before addition of 500 µL of 1 M Tris-HCl (pH 7.6) in the presence of 50 mM NaCNBH$_3$ to block the unreacted aldehyde sites on the bead surface for 0.5 h. For protein conjugation, 200 µg of proteins from each CHO cell line, 2 mg fetuin or 20 µL of serum proteins were first denatured in 100 µL solution consisting of 10× denaturing buffer (New England Biolabs) and 90 µL buffer (pH 10.0) for 10 minutes at 100° C. before following same protocol as that of SGP. The immobilized samples were washed three times with 500 µL of 1 M NaCl and three times with H$_2$O.

To protect the sialic acid groups, glycans on the solid support were incubated with 465 µL of p-toluidine (Sigma) solution (pH 4-6), which consists of 400 µL p-toluidine, 25 µL 36-38% HCl, and 40 µL EDC (N-(3-dimethylaminopropyl)-N'-ethylcarbodiimide; 5.6 M; Sigma). Reaction was preceded for 3 h or longer (overnight is preferred) at room temperature before the chemicals were washed off from the solid support with 500 µL of 10% formic acid (3×), 500 µL of 10% acetonitrile (3×), 500 µL of 1 M NaCl (3×) and finally H$_2$O (3×).

N-Glycan Release

After removing the wash buffer, 2 µL of PNGase F, 16 µL G7 (10×), and 142 µL DI was added to the bead mixture and incubated at 37° C. for overnight to release N-glycans. The eluted glycans were purified by Carbograph and SGP glycans were eluted in 1 mL 80% ACN (0.1% formic acid) while other N-glycan eluents were dried in vacuum. Yang, S. & Zhang, H. Glycan analysis by reversible reaction to hydrazide beads and mass spectrometry. *Anal. Chem.* 84, 2232-2238 (2012). The N-glycans were re-suspended in HPLC grade of water, 200 µL for 1 mg fetuin, 100 µL for serum and 20 µL for CHO respectively.

Protein Tryptic Digestion from Beads

The deglycosylated proteins on the solid support were dissolved with 500 µL of 8 M urea in 0.8 M ammonium bicarbonate (NH$_4$HCO$_3$; pH 8.0), as described in our recent studies. Proteins on beads were reduced with 10 mM of tris (2-carboxyethyl) phosphine hydrochloride (TCEP) at 37° C. for 1 h, followed by alkylation with 20 mM of iodoacetamide (IAA) at room temperature for 30 mins. Samples were then diluted 5-fold with 0.2 M NH$_4$HCO$_3$ to have 1.6 M urea before being digested with trypsin at 37° C. overnight at a ratio of 1:40 (trypsin:protein). Peptides in 0.1% TFA were purified by C18 3 cc Vac Cartridge (500 mg sorbent; Waters Corporation, Milford, Mass.) and eluted with 500 µL 60% acetonitrile (ACN), 2× (Fisher Scientific, Pittsburgh, Pa.). Peptides whose concentration was determined by NanoDrop were labeled with four channels of iTRAQ (AB SCIEX, Framingham, Mass.). The iTRAQ labeled peptides were pooled for C18 cleanup and optionally separated to 8 fractions by basic reverse phase liquid chromatography (bRPLC) on the 1220 Infinity LC system with a Zorbax Extended-C18 analytical column (1.8 µm particles, 4.6×100 mm; Agilent Technologies, Inc., CA). Flow rate is set at 0.2 mL/min and a linear gradient (8 to 35% within 85 min) is used to elute peptide fractions (Buffer A: 10 mM NH$_4$HCO$_2$, pH 10; Buffer B: 10 mM NH$_4$HCO$_2$ and 90% ACN, pH 10). Each fraction was analyzed on a RPLC mass spectrometer (Details refer to LC-MS analysis) using a Q Exactive Quadrupole for global proteomics (Thermo).

QUANTITY Labeling Protocol

The dried glycans were re-suspended in reaction solution mixture consisting of anhydrous dimethyl sulfoxide (DMSO) and acetic acid (AA) (7:3, vol) in the presence of 1 M NaCNBH$_3$. For fetuin, glycans enriched from respective GIG were placed in four vials with a theoretical ratio of 1:1:3:5 (starting fetuin 200:200:600:1000 µg). A fixed volume (20:20:60:100) µL of 100 mM QUANTITY (176, 177, 178, and 179) dissolved in the mixture of DMSO and AA (7:3) were added into each sample respectively and incubated at 65° C. for 4 h. The reaction was quenched by addition of 2 mL water and 2 µL concentrated formic acid. Samples that were labeled with 4-plex QUANTITY were pooled for cleanup by Carbograph™. The purified samples were dissolved in 400 µL of 0.2% formic acid.

Glycans released from 1 mg SGP were purified by Carbograph™ and eluted in 1000 µL of 80% ACN (0.1% TFA). 40 µL eluent was used for labeling with QUANTITY. Another 40 µL SGP was also labeled with aminoxyTMTzero using same protocol as that of QUANTITY (The manufacturer's protocol to label glycan with TMT was not followed. Results showed only a small amount of glycan conjugated. The method using DMSO-HOAc showed best yield). Serum glycans (from 20 µL) were labeled using same protocol as that of SGP.

Figure 6:
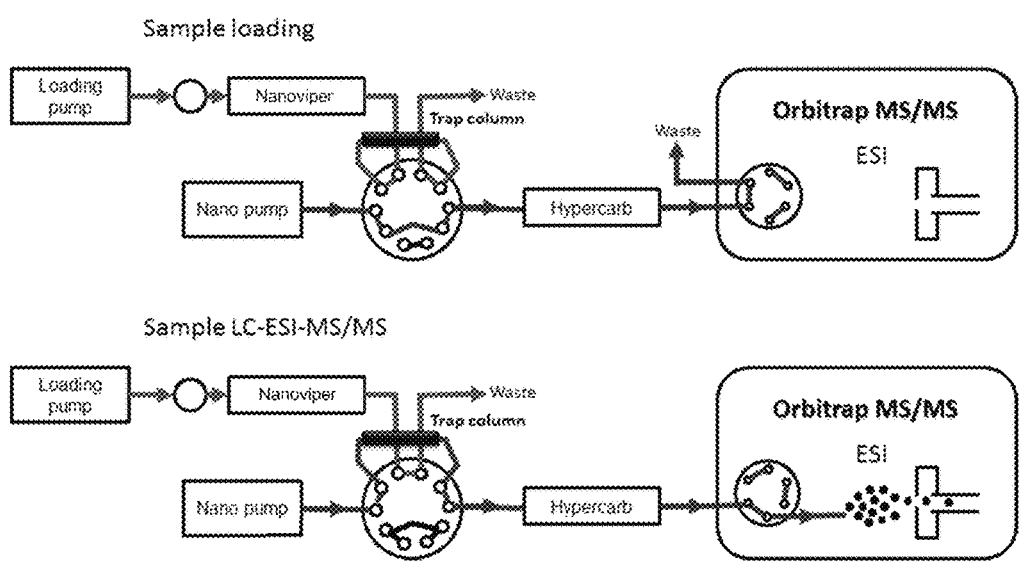
FIG. 6 is a schematic diagram of the instrumental setup for LC-ESI-MS/MS on sample loading and separation using an Orbitrap™ LC-ESI-MS/MS. The trap column is C18.

LC-MS experiments were performed on an Orbitrap™ LC-ESI-MS/MS. QUANTITY-labeled glycans was dissolved in 13 µl of 0.2% TFA for analysis using Orbitrap™ (Velos Pro Mass Spectrometer; Thermo Fisher Scientific Inc.; Waltham, Mass.). The instrumental setup is given in FIG. 6. Flow rate was set to 2 µl/min and each test was run for 10 min. The instrument was operated in data-dependent mode with m/z ranging from 300-2000 Da, in which a full MS scan (mass resolution=60,000) was followed by ten MS/MS scans. The normalized collision energy of higher energy collisional dissociation was 35%, and the dynamic exclusion duration was 25 µs. Ions without assigned charge states were rejected for MS/MS analysis. The heated capillary was maintained at 200° C., while the ESI voltage was maintained at +2.2 kV. Each sample was analyzed in triplicate on the Orbitrap™. System control was achieved using Thermo Xcalibur data acquisition software and data analysis was performed with Thermo Xcalibur Qual Browser (2.2 SP1.48). Glycan identification was performed using Glyco-Workbench software (version 2.0) and CFG Functional Glycomics Gateway. The reporter ions were output using program of Matlab.

MALDI-MS/MS Analysis Method

Glycans (5 µL for each sample out of 1000 µL of elution after Carbograph™ cleanup) extracted from SGP, Fetuin, serum, and CHO cell lines using GIG were analyzed by Axima MALDI Resonance mass spectrometer (Shimadzu). Matrix solution consists of 4 µL DMA in 200 µL DHB (100 µg/µL in 50% acetonitrile, 0.1 mM NaCl) in that DMA can increase the detection of sialylated glycans. The DHB-DMA (1 µL) spots formed uniform crystals and increased sialylated glycan stability by increasing laser power absorption and ionization efficiency 4. The laser power was set to be able to detect intact signal (typically 100-140) for 2 shots each in 100 locations per spot. The average MS spectra (200 profiles) were used for glycan assignment by comparing to the database of glycans previously analyzed by MALDI-MS/MS in our lab. The assigned glycans were confirmed from human serum established in literature. Aldredge, D., An, H. J., Tang, N., Waddell, K. & Lebrilla, C. B. Annotation of a serum N-glycan library for rapid identification of structures. *J. Proteome Res.* 11, 1958-1968 (2012); Stumpo, K. A. & Reinhold, V. N. The N-glycome of human plasma. *J. Proteome Res.* 9, 4823-4830 (2010); Miura, Y. et al. BlotGlycoABC™, an integrated glycoblotting technique for rapid and large scale clinical glycomics. *Mol. Cell. Proteomics* 7, 370-377 (2008).

Design of QUANTITY

As with other isobaric tags for peptides and small molecules, the 4-plex QUANTITY reagents tested are a set of four molecules with identical chemical structures and molecule weight (FIG. 1A), yet they contain different stable isotope nuclei like $^{13}C$ and $^2H$ in various positions as shown herein. Their structures consist of a reporter with molecular mass ranging from 176 to 179 Daltons in the series, a balancer that compensates the mass difference of the reporters, and a reactive primary amine to conjugate with glycans via reductive amination (FIG. 1A). This labeling chemistry is analogous to that used by 2-AA/2-AB (2-aminobenzoic acid (2-AA) or 2-aminobenzamide (2-AB)), (Bigge, J. C. et al. "Nonselective and efficient fluorescent labeling of glycans using 2-amino benzamide and anthranilic acid," *Anal. Biochem.* 230, 229-238 (1995)), so well-established protocols for 2-AA/2-AB labeling can be adapted without many changes by one of skill in the art.

A noticeable difference between the tags of the disclosure and 2-AA/2-AB, however, is that a water molecule is lost spontaneously and stoichiometrically from QUANTITY-labeled glycans, while 2-AA/2-AB labeled glycans only show the partial loss of a water molecule. This phenomenon might be proceeded through an energetically favored six-membered ring formation (a.k.a. neighboring participation reaction) Cai, Y., Ling, C.-C. & Bundle, D. R. "Facile approach to 2-acetamido-2-deoxy-β-D-glucopyranosides via a furanosyl oxazoline" *Org. Lett.* 7, 4021-4024 (2005). Upon MS2 fragmentation, QUANTITY labeled glycans yield strong reporter ions for accurate quantification without the need of extra positive ions such as $Na^+$ or metal ions, thereby eliminating ion suppression effect and preventing the formation of multiple $H^+/Na^+$ adducts. Furthermore, outfitting glycans with a permanently positive-charged quaternary ammonium can enhance their ionization in MS. Therefore, the detection sensitivity of glycans is considerably enhanced, which is advantageous when analyzing low abundance glycans or samples with limited amount.

To apply QUANTITY for glycan analysis, a solid-phase based protocol was developed as shown in FIG. 1C. Yang, S., Li, Y., Shah, P. & Zhang, H., "Glycomic analysis using glycoprotein immobilization for glycan extraction" *Anal. Chem.* 85, 5555-5561 (2013). Glycoproteins are first immobilized on beads and treated with excess p-toluidine in the presence of a carbodiimide coupling reagent. This step can completely conjugate sialic acids on glycans with p-toluidine to stabilize these labile residues during MS analysis. N-glycans are then released from immobilized glycoproteins with PNGase F, resulting in an exposed aldehyde group at their reducing end for quaternary ammonium containing isobaric tag reagent labeling. The labeled glycans are then analyzed with reverse phase liquid chromatography (RPLC) coupled tandem MS. A bonus of this protocol is that a hydrophobic p-toluidine moiety is coupled to each sialic acid, so N-glycans carrying different numbers of sialic acids can be easily resolved on a C18 column.

The monoisotopic mass of a labeled glycan, $M=F_aN_bH_cS_dG_e$, is calculated based on equation 2.

$$M=C+a\times F+b\times N+c\times H+d\times S+e\times G+(d+e)\times pT+Q \quad (2)$$

Here: C stands for N-glycan core structure, 910.3278 Da; F is fucose, 146.0579 Da; N is HexNAc, 203.0794 Da; H is Hexose, 162.0528 Da; S is Neu5Ac, 291.0954 Da; G is Neu5Gc, 307.0903 Da; pT is p-Toluidine, 89.0629 Da (after the loss of one water), which is coupled to each sialic acid in the protocol; Q is QUANTITY, 233.2147 Da (after the loss of one oxygen due to reductive amination and the loss of one water due to neighboring participation reaction); a, b, c, d, e is the number of each respective unit. The core structure (2 HexNAc and 3 Hexose) is excluded from the formula ($F_aN_bH_cS_dG_e$) of N-glycans herein. In other words, b and c represent the HexNAc and Hexose units other than those in the core structure, respectively.

In ESI, a labeled glycan is usually detected as an ion carrying multiple charges (z) with observed m/z as B. We can calculate its monoisotopic mass (M') based on equation 3.

$$M'=B\times Z+(Z-1.0078) \quad (3)$$

To identify a glycan from a MS experiment, the monoisotopic mass (M) of all QUANTITY labeled N-glycans in a glycan library can first be calculated, such as Consortium for Functional Glycomics (CFG) database 17. Then, the monoisotopic mass (M') of an ion in a MS1 spectrum is calculated and matched with the monoisotopic mass (M) calculated from the glycan database to find its composition.

Performance of Quaternary Ammonium Containing Isobaric Tag (QUANTITY)

The completion of QUANTITY labeling was demonstrated as follows. Two N-glycans ($N_2H_2S_2$>90%, and $N_2H_2S$<10%) extracted from 1 mg standard sialylglycopeptide (SGP) were labeled with QUANTITY-176 (30 μL at 40 mM) in 70% dimethyl sulfoxide (DMSO) and 30% acetic acid (HOAc) containing 1 M sodium cyanoborohydride ($NaCNBH_3$). As a comparison, the SGP glycans were also labeled by a commercially available isobaric tag for glycans based on tertiary amine (aminoxyTMT-126) similarly.

Figures 8A, 8B, 8C:
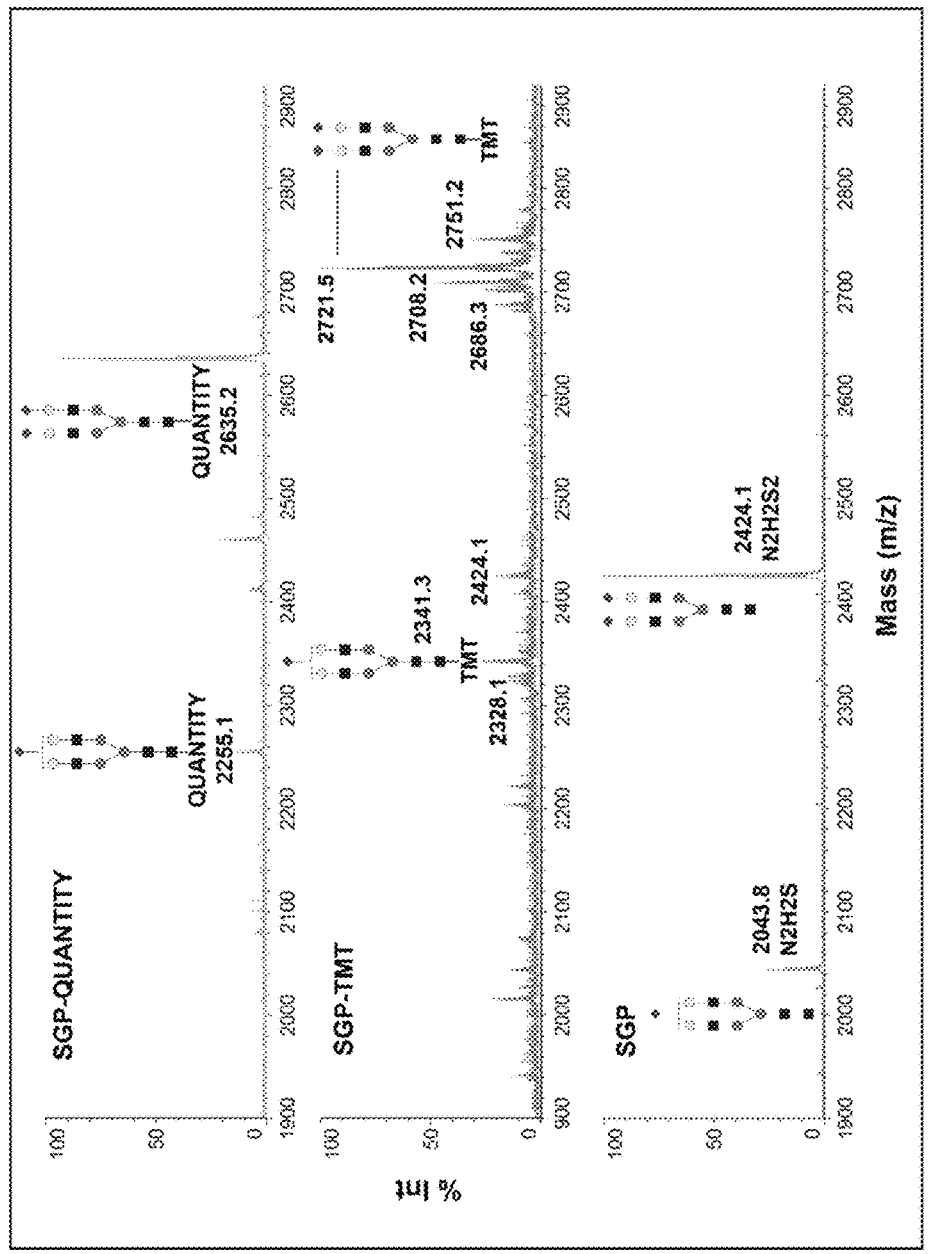
FIG. 8A-8C is MALDI-MS spectra of glycans labeled by a quaternary ammonium containing isobaric tag reagent and aminoxyTMT-126.

FIG. 7A-7F show the MS1 (FIGS. 7A & 7B) and MS2 (FIG. 7C) of QUANTITY labeled SGP glycans, as well as the MS1 (FIGS. 7D & 7E) and MS2 (FIG. 7F) of TMT labeled counterparts acquired on an ESI instrument (their MALDI MS1 spectra, together with the MALDI MS1 of unlabeled SGP glycans are shown in FIG. 8A-8C).

The QUANTITY labeled glycans only show two dominant peaks as labeled $N_2H_2S$ and $N_2H_2S_2$, indicating the labeling reaction was completed. Although aminoxyTMT labeled glycans also show two major peaks, we still observed unlabeled $N_2H_2S$ and $N_2H_2S_2$, suggesting the labeling reaction with aminoxyTMT was more difficult to complete. In addition, the aminoxyTMT labeled glycans display multiple satellite peaks with 14 Dalton mass difference (FIG. 7E), making MS1 more complex and averaging out peak intensity. More significantly, when labeled glycans were fragmented, the reporter ion (m/z 176.11) generated from the quaternary ammonium of QUANTITY yields decent signal in comparison to common glycan fragment ions (m/z 138.05 or 204.09). In contrast, the reporter ion (m/z 126.11) generated from the tertiary amine of aminoxyTMT not only shows much less intensity, but is susceptible to the interference from a glycan fragment (m/z 126.05) (FIGS. 7C and 7F). This experiment clearly demonstrated the completion of QUANTITY labeling and its advantages over existing isobaric tags for glycans.

Figures 9A, 9B, 9C:
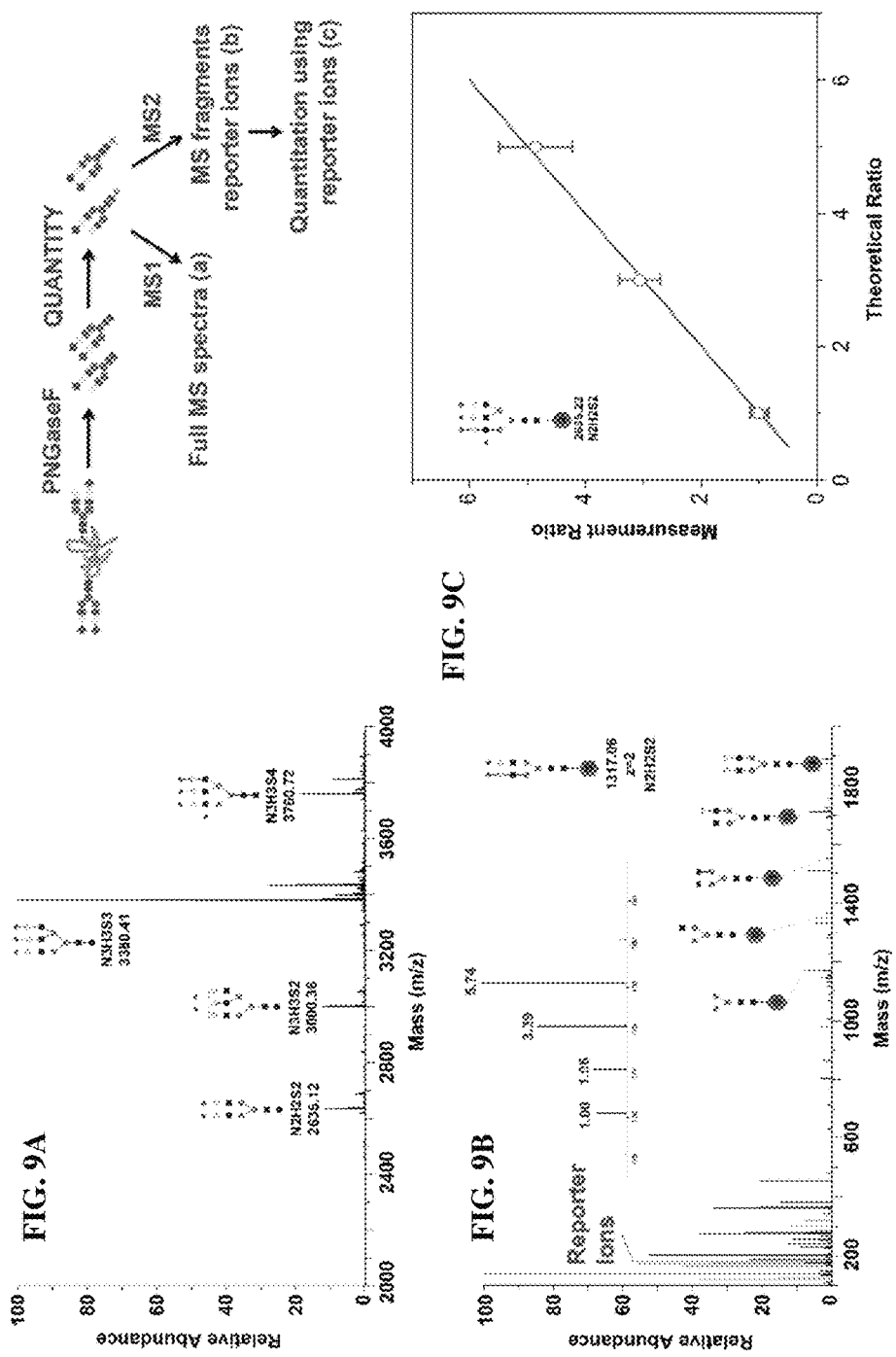
FIG. 9A-9C illustrates the efficiency and linear range of glycan labeling with QUANTITY. Glycans extracted from bovine fetuin are prepared in a ratio of 1:1:3:5 prior to labeling with QUANTITY via reduction amination. The labeled fetuin glycans (176, 177, 178, and 179), sialylated glycans, including $N_2H_2S_2$, $N_3H_3S_2$, $N_3H_3S_3$, and $N_3H_3S_4$, are pooled for electrospray (ESI)—tandem mass spectrometry ($MS^2$) (note: core structure $N_2H_3$ is not included in the composition).

Next, the quantification accuracy of QUANTITY was tested by labeling fetuin glycans with 4-plex QUANTITY at 1:1:3:5 ratio. Fetuin from fetal bovine (200 μg, 200 μg, 600 μg, and 1000 μg; triplicates) were processed by following the protocol detailed above. FIG. 9A shows the MS1 of QUANTITY labeled fetuin N-glycans, including $N_2H_2S_2$, $N_3H_3S_2$, $N_3H_3S_3$, and $N_3H_3S_4$. FIG. 9B is a representative full MS2 spectrum ($N_2H_2S_2$), which includes a series of glycan fragments for easy structural elucidation of the precursor ion and strong reporter ions ranging from 176 to 179.

The inset of FIG. 9A-9C is the expanded low mass range of the MS2 showing the signal of each reporter ion, which indicates the relative abundance of glycans from four original samples. The experimental result of this glycan ($N_2H_2S_2$) is very close to 1:1:3:5. The linear correlation (FIG. 9C) between the measured and theoretical ratios and the small standard deviation from three independent replicates indicate the great reproducibility of QUANTITY quantification. The following table provides additional data:

TABLE 3

Quantitation of N-glycans from bovine fetuin serum using GIG and QUANTITY.

| Symbol | F | N | H | S | M | 176 Average | SD | 177 Average | SD | 178 Average | SD | 179 Average | SD |
|---|---|---|---|---|---|---|---|---|---|---|---|---|---|
| $N_2H_2S$ | 0 | 2 | 2 | 1 | 2255.0 | 0.94 | 0.02 | 1.06 | 0.02 | 3.39 | 0.11 | 5.45 | 0.24 |
| $N_2H_2S_2$ | 0 | 2 | 2 | 2 | 2635.2 | 0.94 | 0.04 | 1.06 | 0.04 | 3.48 | 0.13 | 5.74 | 0.52 |
| $N_3H_3S_2$ | 0 | 3 | 3 | 2 | 3000.4 | 0.95 | 0.02 | 1.05 | 0.02 | 3.58 | 0.21 | 5.83 | 0.36 |
| $N_3H_3S_3$ | 0 | 3 | 3 | 3 | 3380.5 | 0.92 | 0.07 | 1.08 | 0.07 | 3.54 | 0.36 | 6.12 | 0.95 |
| $N_3H_3S_4$ | 0 | 3 | 3 | 4 | 3760.7 | 0.99 | 0.15 | 1.01 | 0.15 | 3.06 | 0.35 | 4.86 | 0.63 |

SD = standard deviation.

QUANTITY was then tested for whether QUANTITY can be applied for complex biological samples.

Figure 10:
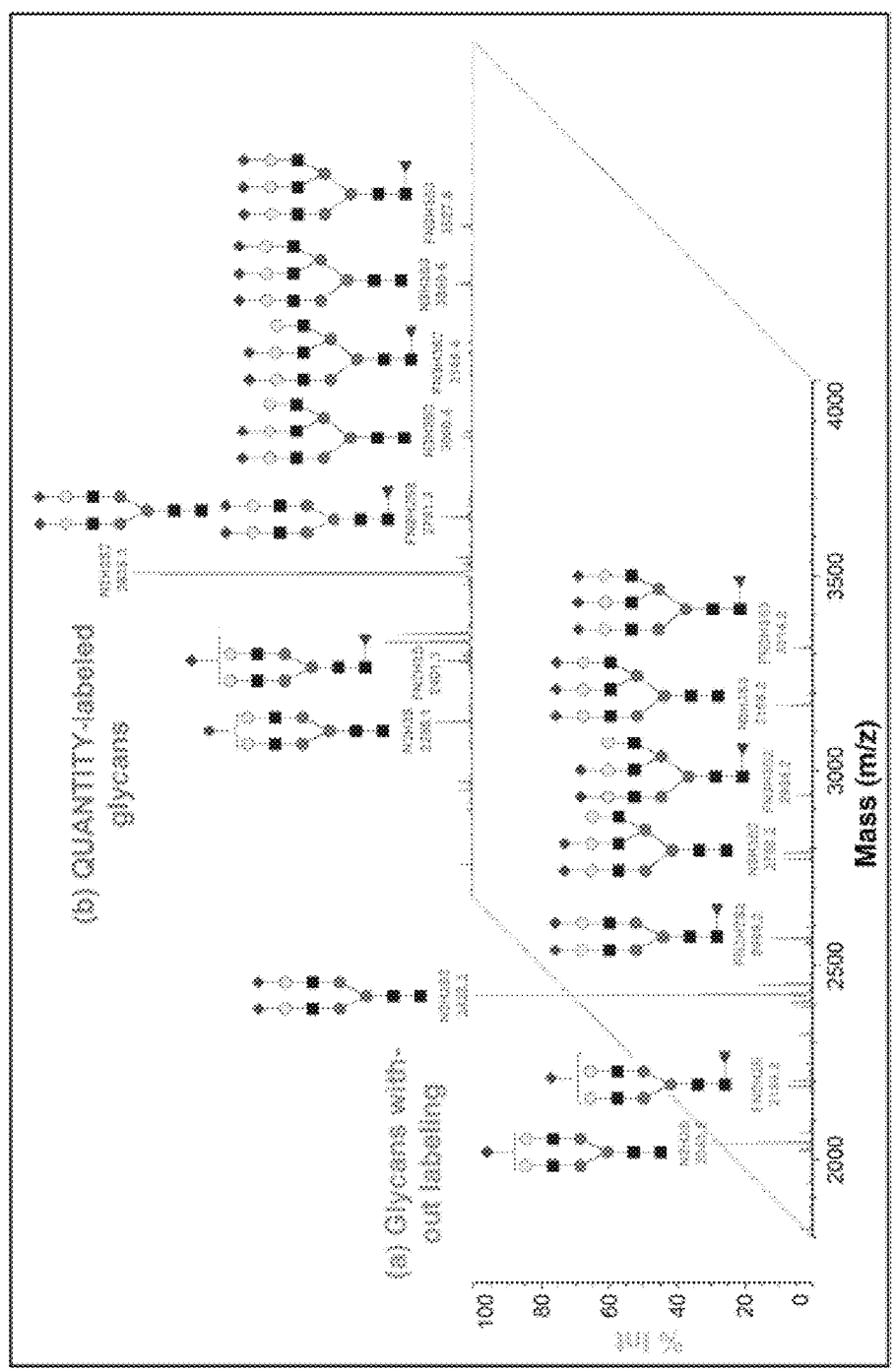
FIG. 10 shows MALDI-MS spectra of serum native N-glycans (a) and QUANTITY-labeled N-glycans (b) extracted from human sera using glycoprotein immobilization for glycan extraction (GIG).

N-Glycans from 20 μL human serum were extracted and labeled with QUANTITY completely. A quick survey with MALDI-MS showed the profiling of serum N-glycans after QUANTITY labeling was the same as that of native N-glycans (FIG. 10), whereas a more detailed analysis with RPLC-MS allowed the identification of over 90 N-glycans from serum (Table 4).

TABLE 4

| Symbol | F a | N b | H c | S d | G | G-pT | $[M + H]^+$ | $[M + H]^{2+}$ | $[M + H]^{3+}$ | $[M + H]^{4+}$ |
|---|---|---|---|---|---|---|---|---|---|---|
| N | 0 | 1 | 0 | 0 | 1136.4 | 1136.4 | 1347.7 | 673.8 | 449.2 | 336.9 |
| FH | 1 | 0 | 1 | 0 | 1241.4 | 1241.4 | 1452.7 | 726.3 | 484.2 | 363.2 |
| $FH_2$ | 1 | 0 | 2 | 0 | 1403.5 | 1403.5 | 1614.7 | 807.4 | 538.2 | 403.7 |
| NS | 0 | 1 | 0 | 1 | 1449.5 | 1516.6 | 1727.8 | 863.9 | 575.9 | 432.0 |
| $N_3$ | 0 | 3 | 0 | 0 | 1542.6 | 1542.6 | 1753.8 | 876.9 | 584.6 | 438.5 |
| NHS | 0 | 1 | 1 | 1 | 1611.6 | 1678.7 | 1889.9 | 944.9 | 630.0 | 472.5 |
| FNHS | 1 | 1 | 1 | 1 | 1757.6 | 1824.7 | 2035.9 | 1018.0 | 678.6 | 509.0 |
| $N_2HS$ | 0 | 2 | 1 | 1 | 1814.7 | 1881.8 | 2093.0 | 1046.5 | 697.7 | 523.2 |
| $N_2H_2S$ | 0 | 2 | 2 | 1 | 1976.7 | 2043.8 | 2255.0 | 1127.5 | 751.7 | 563.8 |
| $N_3HS$ | 0 | 3 | 1 | 1 | 2017.8 | 2084.8 | 2296.1 | 1148.0 | 765.4 | 574.0 |
| $F_3N_2H_2$ | 3 | 2 | 2 | 0 | 2101.8 | 2101.8 | 2313.0 | 1156.5 | 771.0 | 578.3 |
| $H_5S$ | 0 | 0 | 5 | 1 | 2056.7 | 2123.8 | 2335.0 | 1167.5 | 778.3 | 583.8 |
| $F_2N_3H_2$ | 2 | 3 | 2 | 0 | 2158.8 | 2158.8 | 2370.1 | 1185.0 | 790.0 | 592.5 |
| $FN_2H_2S$ | 1 | 2 | 2 | 1 | 2122.8 | 2189.9 | 2401.1 | 1200.5 | 800.4 | 600.3 |
| $NH_2S_2$ | 0 | 1 | 2 | 2 | 2086.7 | 2220.9 | 2432.1 | 1216.1 | 810.7 | 608.0 |
| $N_3H_2S$ | 0 | 3 | 2 | 1 | 2179.8 | 2246.9 | 2458.1 | 1229.1 | 819.4 | 614.5 |
| $N_4HS$ | 0 | 4 | 1 | 1 | 2220.9 | 2287.9 | 2499.2 | 1249.6 | 833.1 | 624.8 |
| $F_4N_3H$ | 4 | 3 | 1 | 0 | 2288.9 | 2288.9 | 2500.1 | 1250.1 | 833.4 | 625.0 |
| $FN_3H_2S$ | 1 | 3 | 2 | 1 | 2325.9 | 2393.0 | 2604.2 | 1302.1 | 868.1 | 651.0 |
| $N_3H_3S$ | 0 | 3 | 3 | 1 | 2341.9 | 2409.0 | 2620.2 | 1310.1 | 873.4 | 655.0 |
| $N_2H_2S_2$ | 0 | 2 | 2 | 2 | 2289.8 | 2424.0 | 2635.2 | 1317.6 | 878.4 | 658.8 |
| $FN_6H$ | 1 | 6 | 1 | 0 | 2460.0 | 2460.0 | 2671.2 | 1335.6 | 890.4 | 667.8 |
| $F_3N_3H_3$ | 3 | 3 | 3 | 0 | 2466.9 | 2466.9 | 2678.2 | 1339.1 | 892.7 | 669.5 |
| $F_3N_2H_2S$ | 3 | 2 | 2 | 1 | 2414.9 | 2482.0 | 2693.2 | 1346.6 | 897.7 | 673.3 |
| $F_2N_3H_4$ | 2 | 3 | 4 | 0 | 2482.9 | 2482.9 | 2694.2 | 1347.1 | 898.1 | 673.5 |
| $F_2N_3H_2S$ | 2 | 3 | 2 | 1 | 2471.9 | 2539.0 | 2750.2 | 1375.1 | 916.7 | 687.6 |
| $FN_2H_2S_2$ | 1 | 2 | 2 | 2 | 2435.9 | 2570.0 | 2781.3 | 1390.6 | 927.1 | 695.3 |
| $N_2H_3S_2$ | 0 | 2 | 3 | 2 | 2451.9 | 2586.0 | 2797.3 | 1398.6 | 932.4 | 699.3 |
| $N_3H_2S_2$ | 0 | 3 | 2 | 2 | 2492.9 | 2627.1 | 2838.3 | 1419.2 | 946.1 | 709.6 |
| $NH_7S$ | 0 | 1 | 7 | 1 | 2583.9 | 2651.0 | 2862.2 | 1431.1 | 954.1 | 715.6 |
| $F_3N_3H_2S$ | 3 | 3 | 2 | 1 | 2618.0 | 2685.1 | 2896.3 | 1448.2 | 965.4 | 724.1 |
| $FN_3H_2S_2$ | 1 | 3 | 2 | 2 | 2639.0 | 2773.1 | 2984.4 | 1492.2 | 994.8 | 746.1 |
| $N_3H_3S_2$ | 0 | 3 | 3 | 2 | 2655.9 | 2789.1 | 3000.4 | 1500.2 | 1000.1 | 750.1 |
| $FN_3H_3S_2$ | 1 | 3 | 3 | 2 | 2801.0 | 2935.2 | 3146.4 | 1573.2 | 1048.8 | 786.6 |
| $FN_4H_2S_2$ | 1 | 4 | 2 | 2 | 2842.1 | 2976.2 | 3187.5 | 1593.7 | 1062.5 | 796.9 |
| $F_2N_9$ | 2 | 9 | 0 | 0 | 3053.3 | 3053.3 | 3264.5 | 1632.3 | 1088.2 | 816.1 |
| $F_2N_3H_3S_2$ | 2 | 3 | 3 | 2 | 2947.1 | 3081.2 | 3292.5 | 1646.2 | 1097.5 | 823.1 |
| $F_2N_2H_2S_3$ | 2 | 2 | 2 | 3 | 2895.0 | 3096.3 | 3307.5 | 1653.8 | 1102.5 | 826.9 |
| $N_4H_4S_2$ | 0 | 4 | 4 | 2 | 3020.1 | 3154.3 | 3365.5 | 1682.8 | 1121.8 | 841.4 |
| $N_3H_3S_3$ | 0 | 3 | 3 | 3 | 2968.1 | 3169.3 | 3380.5 | 1690.3 | 1126.8 | 845.1 |
| $F_3N_2H_4S_2$ | 3 | 2 | 4 | 2 | 3052.1 | 3186.3 | 3397.5 | 1698.7 | 1132.5 | 849.4 |
| $F_3N_4H_4S$ | 3 | 4 | 4 | 1 | 3145.2 | 3212.3 | 3423.5 | 1711.8 | 1141.2 | 855.9 |
| $F_3N_3H_3S_2$ | 3 | 3 | 3 | 2 | 3093.1 | 3227.3 | 3438.5 | 1719.3 | 1146.2 | 859.6 |
| $F_3N_2H_2S_3$ | 3 | 2 | 2 | 3 | 3041.1 | 3242.3 | 3453.6 | 1726.8 | 1151.2 | 863.4 |
| $F_2N_4H_3S_2$ | 2 | 4 | 3 | 2 | 3150.2 | 3284.3 | 3495.6 | 1747.8 | 1165.2 | 873.9 |
| $FN_4H_4S_2$ | 1 | 4 | 4 | 2 | 3166.2 | 3300.3 | 3511.6 | 1755.8 | 1170.5 | 877.9 |
| $FN_3H_3S_3$ | 1 | 3 | 3 | 3 | 3114.1 | 3315.4 | 3526.6 | 1763.3 | 1175.5 | 881.7 |
| $N_3H_4S_3$ | 0 | 3 | 4 | 3 | 3130.1 | 3331.4 | 3542.6 | 1771.3 | 1180.9 | 885.6 |
| $N_5H_4S_2$ | 0 | 5 | 4 | 2 | 3223.2 | 3357.4 | 3568.6 | 1784.3 | 1189.5 | 892.2 |
| $N_4H_3S_3$ | 0 | 4 | 3 | 3 | 3171.2 | 3372.4 | 3583.6 | 1791.8 | 1194.5 | 895.9 |
| $FN_9H_3$ | 1 | 9 | 3 | 0 | 3393.4 | 3393.4 | 3604.6 | 1802.3 | 1201.5 | 901.2 |
| $F_2N_5H_5S$ | 2 | 5 | 5 | 1 | 3364.3 | 3431.4 | 3642.6 | 1821.3 | 1214.2 | 910.6 |
| $F_2N_4H_4S_2$ | 2 | 4 | 4 | 2 | 3312.2 | 3446.4 | 3657.6 | 1828.8 | 1219.2 | 914.4 |

TABLE 4-continued

| Symbol | F a | N b | H c | S d | G | G-pT | [M + H]⁺ | [M + H]²⁺ | [M + H]³⁺ | [M + H]⁴⁺ |
|---|---|---|---|---|---|---|---|---|---|---|
| $F_2N_3H_3S_3$ | 2 | 3 | 3 | 3 | 3260.2 | 3461.4 | 3672.7 | 1836.3 | 1224.2 | 918.2 |
| $FN_4H_3S_3$ | 1 | 4 | 3 | 3 | 3317.2 | 3518.5 | 3729.7 | 1864.8 | 1243.2 | 932.4 |
| $N_4H_4S_3$ | 0 | 4 | 4 | 3 | 3333.2 | 3534.5 | 3745.7 | 1872.8 | 1248.6 | 936.4 |
| $N_3H_3S_4$ | 0 | 3 | 3 | 4 | 3281.2 | 3549.5 | 3760.7 | 1880.4 | 1253.6 | 940.2 |
| $N_5H_3S_3$ | 0 | 5 | 3 | 3 | 3374.2 | 3575.5 | 3786.7 | 1893.4 | 1262.2 | 946.7 |
| $F_3N_4H_4S_2$ | 3 | 4 | 4 | 2 | 3458.3 | 3592.5 | 3803.7 | 1901.8 | 1267.9 | 950.9 |
| $FN_5H_5S_2$ | 1 | 5 | 5 | 2 | 3531.3 | 3665.5 | 3876.7 | 1938.4 | 1292.2 | 969.2 |
| $FN_4H_4S_3$ | 1 | 4 | 4 | 3 | 3479.3 | 3680.5 | 3891.7 | 1945.9 | 1297.2 | 972.9 |
| $FN_3H_3S_4$ | 1 | 3 | 3 | 4 | 3427.2 | 3695.5 | 3906.8 | 1953.4 | 1302.3 | 976.7 |
| $FN_5H_3S_3$ | 1 | 5 | 3 | 3 | 3520.3 | 3721.6 | 3932.8 | 1966.4 | 1310.9 | 983.2 |
| $F_2N_6H_6S$ | 2 | 6 | 6 | 1 | 3729.4 | 3796.5 | 4007.7 | 2003.9 | 1335.9 | 1001.9 |
| $F_2N_4H_4S_3$ | 2 | 4 | 4 | 3 | 3625.3 | 3826.6 | 4037.8 | 2018.9 | 1345.9 | 1009.5 |
| $N_5H_5S_3$ | 0 | 5 | 5 | 3 | 3698.4 | 3899.6 | 4110.8 | 2055.4 | 1370.3 | 1027.7 |
| $N_4H_4S_4$ | 0 | 4 | 4 | 4 | 3646.3 | 3914.6 | 4125.9 | 2062.9 | 1375.3 | 1031.5 |
| $F_3N_3H_5S_3$ | 3 | 3 | 5 | 3 | 3730.3 | 3931.6 | 4142.8 | 2071.4 | 1380.9 | 1035.7 |
| $F_4N_4H_3S_3$ | 4 | 4 | 3 | 3 | 3755.4 | 3956.6 | 4167.9 | 2083.9 | 1389.3 | 1042.0 |
| $F_3N_4H_4S_3$ | 3 | 4 | 4 | 3 | 3771.4 | 3972.6 | 4183.9 | 2091.9 | 1394.6 | 1046.0 |
| $F_4N_5H_2S_3$ | 4 | 5 | 2 | 3 | 3796.4 | 3997.7 | 4208.9 | 2104.5 | 1403.0 | 1052.2 |
| $F_3N_5H_3S_3$ | 3 | 5 | 3 | 3 | 3812.4 | 4013.7 | 4224.9 | 2112.5 | 1408.3 | 1056.2 |
| $FN_6H_6S_2$ | 1 | 6 | 6 | 2 | 3896.5 | 4030.6 | 4241.9 | 2120.9 | 1414.0 | 1060.5 |
| $FN_5H_5S_3$ | 1 | 5 | 5 | 3 | 3844.4 | 4045.7 | 4256.9 | 2128.4 | 1419.0 | 1064.2 |
| $FN_4H_4S_4$ | 1 | 4 | 4 | 4 | 3792.4 | 4060.7 | 4271.9 | 2136.0 | 1424.0 | 1068.0 |
| $N_4H_5S_4$ | 0 | 4 | 5 | 4 | 3808.4 | 4076.7 | 4287.9 | 2144.0 | 1429.3 | 1072.0 |
| $FN_9H_5S$ | 1 | 9 | 5 | 1 | 4030.6 | 4097.7 | 4308.9 | 2154.5 | 1436.3 | 1077.2 |
| $F_2N_4H_4S_4$ | 2 | 4 | 4 | 4 | 3938.4 | 4206.8 | 4418.0 | 2209.0 | 1472.7 | 1104.5 |
| $N_6H_6S_3$ | 0 | 6 | 6 | 3 | 4063.5 | 4264.8 | 4476.0 | 2238.0 | 1492.0 | 1119.0 |
| $N_5H_5S_4$ | 0 | 5 | 5 | 4 | 4011.5 | 4279.8 | 4491.0 | 2245.5 | 1497.0 | 1122.8 |
| $F_3N_4H_4S_4$ | 3 | 4 | 4 | 4 | 4084.5 | 4352.8 | 4564.0 | 2282.0 | 1521.3 | 1141.0 |
| $FN_5H_5S_4$ | 1 | 5 | 5 | 4 | 4157.5 | 4425.8 | 4637.1 | 2318.5 | 1545.7 | 1159.3 |
| $F_2N_5H_5S_4$ | 2 | 5 | 5 | 4 | 4303.6 | 4571.9 | 4783.1 | 2391.6 | 1594.4 | 1195.8 |
| $N_6H_6S_4$ | 0 | 6 | 6 | 4 | 4376.6 | 4644.9 | 4856.2 | 2428.1 | 1618.7 | 1214.0 |
| $F_3N_5H_5S_4$ | 3 | 5 | 5 | 4 | 4449.6 | 4718.0 | 4929.2 | 2464.6 | 1643.1 | 1232.3 |
| $F_2N_6H_6S_4$ | 2 | 6 | 6 | 4 | 4668.7 | 4937.0 | 5148.3 | 2574.1 | 1716.1 | 1287.1 |
| $N_7H_7S_4$ | 0 | 7 | 7 | 4 | 4741.7 | 5010.1 | 5221.3 | 2610.7 | 1740.4 | 1305.3 |
| $N_6H_6S_5$ | 0 | 6 | 6 | 5 | 4689.7 | 5025.1 | 5236.3 | 2618.2 | 1745.4 | 1309.1 |
| $F_3N_9H_3S_4$ | 3 | 9 | 3 | 4 | 4937.9 | 5206.2 | 5417.5 | 2708.7 | 1805.8 | 1354.4 |
| $N_6H_6S_6$ | 0 | 6 | 6 | 6 | 5002.8 | 5405.3 | 5616.5 | 2808.3 | 1872.2 | 1404.1 |

As shown, QUANTITY is a robust and sensitive approach for glycan analysis from complex biospecimens.

Glycomic Investigation of Bioengineered CHO Cells

Currently, five of the ten best-selling drugs are recombinant proteins that treat various conditions including diabetes and arthritis. Zambrowicz, B. P. & Sands, A. T. Knockouts model the 100 best-selling drugs—will they model the next 100? *Nat. Rev. Drug Discov.* 2, 38-51 (2003); Rask-Andersen, M., et al. The druggable genome: evaluation of drug targets in clinical trials suggests major shifts in molecular class and indication. *Ann. Rev. Pharmacol. Toxicol.* 54, 9-26 (2014).

These therapeutic proteins, especially monoclonal antibodies, are usually modified with N-glycans, which can have profound impact on their efficacy and stability. CHO cells are widely used for the production of these biological drugs since they can produce glycoproteins compatible with humans and glycosylation can also be manipulated through genetic engineering. Bragonzi, A. et al. A new Chinese hamster ovary cell line expressing α2, 6-sialyltransferase used as universal host for the production of human-like sialylated recombinant glycoproteins. *Biochim. Biophys.* 1474, 273-282 (2000).

It is well known that the modification of glycan biosynthetic pathways can alter the size of the glycans and the sites available for sialic acid attachment, which are associated with circulatory half-life of many therapeutic glycoproteins like erythropoietin (EPO). Egrie, J. C., et al. Darbepoetin alfa has a longer circulating half-life and greater in vivo potency than recombinant human erythropoietin. *Exp. Hematol.* 31, 290-299 (2003); Bork, K., et al. Increasing the sialylation of therapeutic glycoproteins: the potential of the sialic acid biosynthetic pathway. *J. Pharma. Sci.* 98, 3499-3508 (2009). Therefore, it is of great significance for biopharmaceutical industry to investigate protein glycosylation on normal and engineered CHO cells. To demonstrate the feasibility of QUANTITY for this important application, N-glycans from three different CHO cells were quantitatively analyzed, including wild-type CHO-K1 (WT), CHO-K1 with a knock-in ST6Gal1 gene (ST6Gal1(+)), and CHO-K1 with a knock-out ST3Gal4 gene (ST3Gal4(−)). ST6Gal1 represents ST6 beta-galactosamide alpha-2,6-sialyltransferase 1 and ST3Gal4 stands for ST3 beta-galactoside alpha-2,3-sialyltransferase 4, both of which belong to the glycosyltransferase 29 family that is involved in protein glycosylation.

Figure 12:
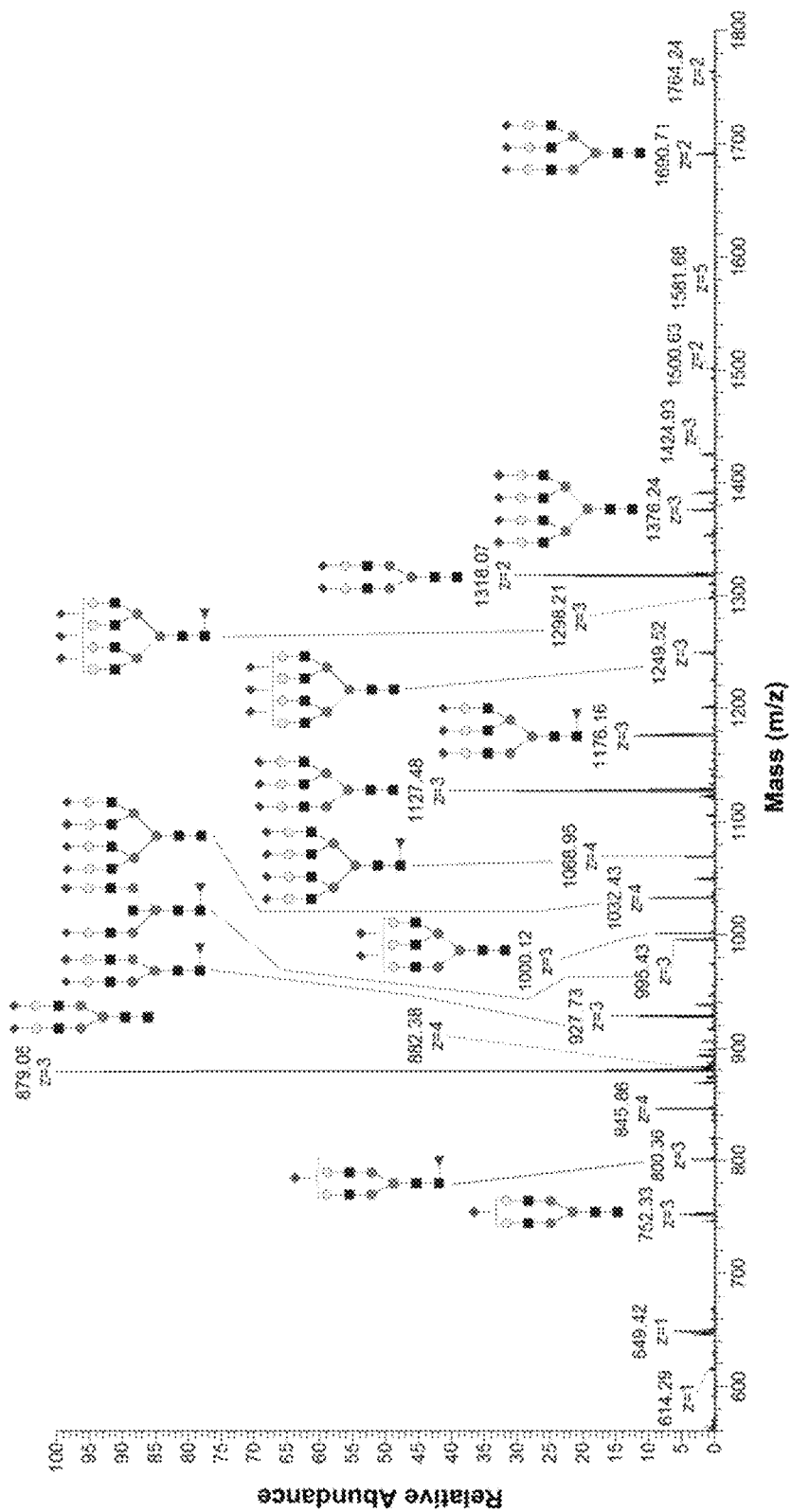
FIG. 12 shows profiling of QUANTITY-labeled N-glycan extracted from CHO cell lines using glycoprotein immobilization for glycan extraction (GIG) by Orbitrap™ LC-ESI-MS/MS.
Figure 15:
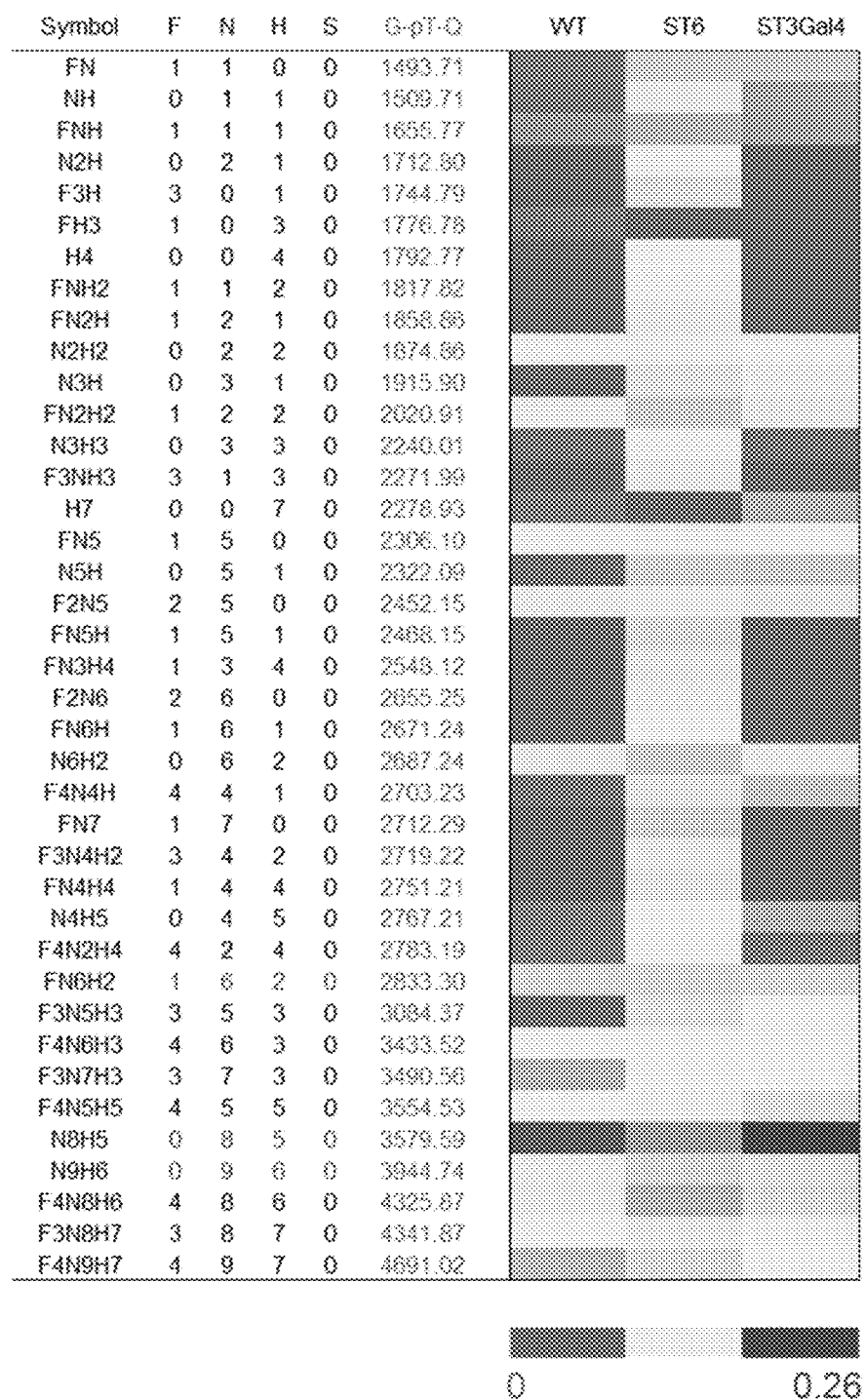
FIG. 15 is a heat map of relative abundance of non-sialic acid in CHO cell lines as described in Example 4.

Three cell lines were cultured in 500 mL of F12-K medium with fetal bovine serum respectively, except for ST6Gal1(+) in which 250 μg blasticidin was also included. Glycans extracted from these cells were analyzed by using the solid phase based protocol of the disclosure (FIG. 12). Most QUANTITY-labeled glycans exhibited multiple charges (+2 and +3) and gave satisfactory MS2 fragments for structural determination (FIG. 13A & FIG. 13C). After all precursor ions were extracted as singly-charged peaks by Thermo Xcalibur™-Xtract (FIG. 13B), each glycan only consisted of a single species and no metal adducts were observed. This feature, unique to QUANTITY-labeled glycans, was significant in that glycans could otherwise form multiple metal adducts that average out their intensity to more species and reduce their detection sensitivity. FIG. 13C is the representative full MS2 spectrum of $N_2H_2S$ showing strong low mass reporter ions for its quantification and distinct large fragments for its structural identification. The reporter ions of several other glycans, including $FN_2H_2S_2$, $N_2H_2S_2$, $N_3H_3S_3$, and $N_5H_4S_4$, are shown in FIG. 13D.

A complete list of N-glycans from CHO (WT, ST6Gal1 (+), and ST3Gal4(−)) is provided (FIG. 14A-14D, FIG. 11A-11D, FIG. 12 and FIG. 15). Lectin blot confirmed the up-regulation of sialic acids in ST6Gal1 (+) and the partial down-regulation of sialic acids in ST3Gal4 (−) (FIG. 14A). A total of 159 N-glycans were quantitatively analyzed, in which 114 (71.2%) of the N-glycans were up-regulated in ST6Gal1(+). These over-expressed glycans had a greater number of terminal sialic acids, as depicted in a heatmap (FIG. 14B). The most abundant sialylated glycans, including $N_2H_2S$, $N_2H_2S_2$, $FN_2H_2S_2$, are over-expressed in ST6Gal1 (+) while down-regulated in ST3Gal4 (−) as expected (FIGS. 14C, 14D). In addition, 44 glycans were only detected in ST6Gal1(+) compared to WT, such as $FN_5H_5S_6$. In contrast, only 22 (13.8%) glycans were down-regulated in ST3Gal4(−). Three of them ($FN_2H_2S_3$, $FH_3$, and $FN_3HS$) were completely absent in ST3Gal4(−), while the other 19 glycans (e.g. $N_3H_3S$, $N_2H_2S_2$, $FN_2H_2S_2$, and $FN_6H_2$) were only down-regulated, probably because other enzymes partially compensate the lost ST3Gal4 activity. These results indicate that protein glycosylation in CHO cells can be significantly modified by regulating the expression of a large family of genes that are involved in glycan biosynthesis. This can not only provide a powerful means to quantitatively investigate the in vivo functions of these enzymes, but also lead to engineered CHO cells for the production of therapeutic proteins with better pharmaceutical properties.

FIG. 11A-D is a list of QUANTITY-labeled glycans from the pooled CHO cell lines. CHO WT is labeled with QUANTITY 176, CHO.ST6 with 178 and CHO.ST3Gal4 with 179.

Using QUANTITY, the glycomics of three CHO cell lines were compared, including WT, ST6Gal1(+), and ST3Gal4 (−). Because CHO cells are used for therapeutic proteins expression in pharmaceutical industry, understanding the impact of knock-in or knock-out enzymes involved in protein glycosylation is of great significance for protein drug discovery and manufacturing. The over-expression of ST6Gal1 indeed boosted protein N-glycosylation and led to increased level of sialylation, while the under-expression of ST3Gal4 showed opposite effect to less degree.

The results indicate QUANTITY is a robust tool to investigate the biological functions of protein glycosylation and understand their roles in drug discovery and development. For example, the terminal sialic acids on N-glycans are well known for their contribution to biological characteristics of many glycoproteins, such as stability, solubility, degradation, and antigenicity. They can prevent glycoproteins from being recognized and removed by the asialoglycoprotein receptor of hepatocyte cells to improve their circulatory lifespan. Bork, K., Horstkorte, R. & Weidemann, W. Increasing the sialylation of therapeutic glycoproteins: the potential of the sialic acid biosynthetic pathway. *J. Pharma. Sci.* 98, 3499-3508 (2009); Morell, A. G., Gregoriadis, G., Scheinberg, I. H., Hickman, J. & Ashwell, G. The role of sialic acid in determining the survival of glycoproteins in the circulation. *J. Biol. Chem.* 246, 1461-1467 (1971). Thus, maximizing sialic acid content in therapeutic glycoproteins is highly desirable by pharmaceutical industry to ensure their quality and consistency. The disclosure of the invention therefore demonstrates the power of glycomic analysis and provides a guideline for the bioengineering of CHO cells for better protein drug production.

Example 5

A total of 82 N-glycans were identified by HPLC-ESI-MS/MS (Q-Exactive; Thermo) according to the protocol of the disclosure. Sialic acids were derivatized via carbodiimide coupling using p-toluidine/EDC; N-glycans are further reacted with QUANTITY reagents as shown in FIG. 1A. Yang et al., "The Use of QABIT-ESI-HPLC-MS/MS-for Quantitation of Tissue Sialylation in a Mouse Model of GNE Myopathy," Poster Presentation, 30th Asilomar Conference on Mass Spectrometry Advances in Glycomics and Glycoproteomics: Methods and Applications October 10-14, 2014.

A total of 469 unique proteins were identified by ESI-MS/MS (1 μg peptides). Only 6 proteins were up-regulated in heterozygous (HET) mouse; 32 proteins were over-expressed in mutant (Mut over C or control). Among those proteins, 20 were up-regulated only in mutant. Sialylated N-glycans were down-regulated in mouse kidney with GNE myopathy. Matrix remodeling proteins were also overexpressed in mutant mice. Table 5 shows the results:

TABLE 5

| Accession | Protein | Gene | MW [kDa] | calc. pI | Het | Mut | Functions |
|---|---|---|---|---|---|---|---|
| 320548 | major urinary protein 1 | Mup1 | 5.4 | 5.9 | 1.10 | 2.54 | Energy metabolism |
| 16323033 | immunoglobin alpha heavy chain constant region | Ign-2 | 21.4 | 5.3 | 0.84 | 2.42 | Increased in GNE muscle |
| 148676839 | histone H3.3 | Anapl_06356 | 9.9 | 9.2 | 0.82 | 2.15 | |
| 117580250 | histone cluster 1, H2bj | Hst1h2bj | 13.6 | 10.4 | 0.85 | 1.99 | Nucleosome structure |
| 148679765 | dipeptidase 1 | Dpep1 | 45.7 | 6.4 | 0.99 | 1.92 | Kidney membrane enzyme |
| 148687981 | D-amino acid oxidase | Dao | 27.8 | 6.0 | 1.25 | 1.91 | A peroxisomal enzyme |
| 13435564 | annexin A2 | Anxa2 | 25.9 | 7.7 | 1.21 | 1.86 | Cell motility, fibrinolysis |
| 74178500 | integrin alpha V | Itgav | 69.5 | 6.7 | 1.06 | 1.77 | Associate with muscular dystrophy/myopathy |
| 2145139 | apolipoprotein A-I | Apoa1 | 30.5 | 5.7 | 1.05 | 1.68 | GNE-specific proteins |
| 12836375 | enoyl-Coenzyme A, hydratase/3-hydroxyacyl Coenzyme A dehydrogenase | Ehhadh | 78.2 | 9.2 | 1.14 | 1.64 | Fatty acid metabolism |
| 19343781 | enoyl-Coenzyme A hydratase domain containing 2 | Echdc2 | 14.5 | 9.3 | 0.91 | 1.63 | Associated with progressive myopathy (J Clin Invest: 1998) |
| 387090 | actin, alpha, cardiac muscle 1 | Actc1 | 41.8 | 3.4 | 1.05 | 1.61 | Actin sliding velocity of the mutant myosin decreased |

TABLE 5-continued

| Accession | Protein | Gene | MW [kDa] | calc. pI | Het | Mut | Functions |
|---|---|---|---|---|---|---|---|
| 143707063 | transgelin 2 | Tagln2 | 22.4 | 8.2 | 1.00 | 1.58 | Actin binding protein |
| 143680652 | profilin 1 | Pfn1 | 13.9 | 5.2 | 1.24 | 1.55 | Mutation in Pfn1 causes familial amyotrophic lateral sclerosis |
| 33991500 | glutathione peroxidase 1 | Gpx1 | 22.3 | 7.2 | 1.08 | 1.52 | Enzyme for peroxidase activity |

Figure 16:
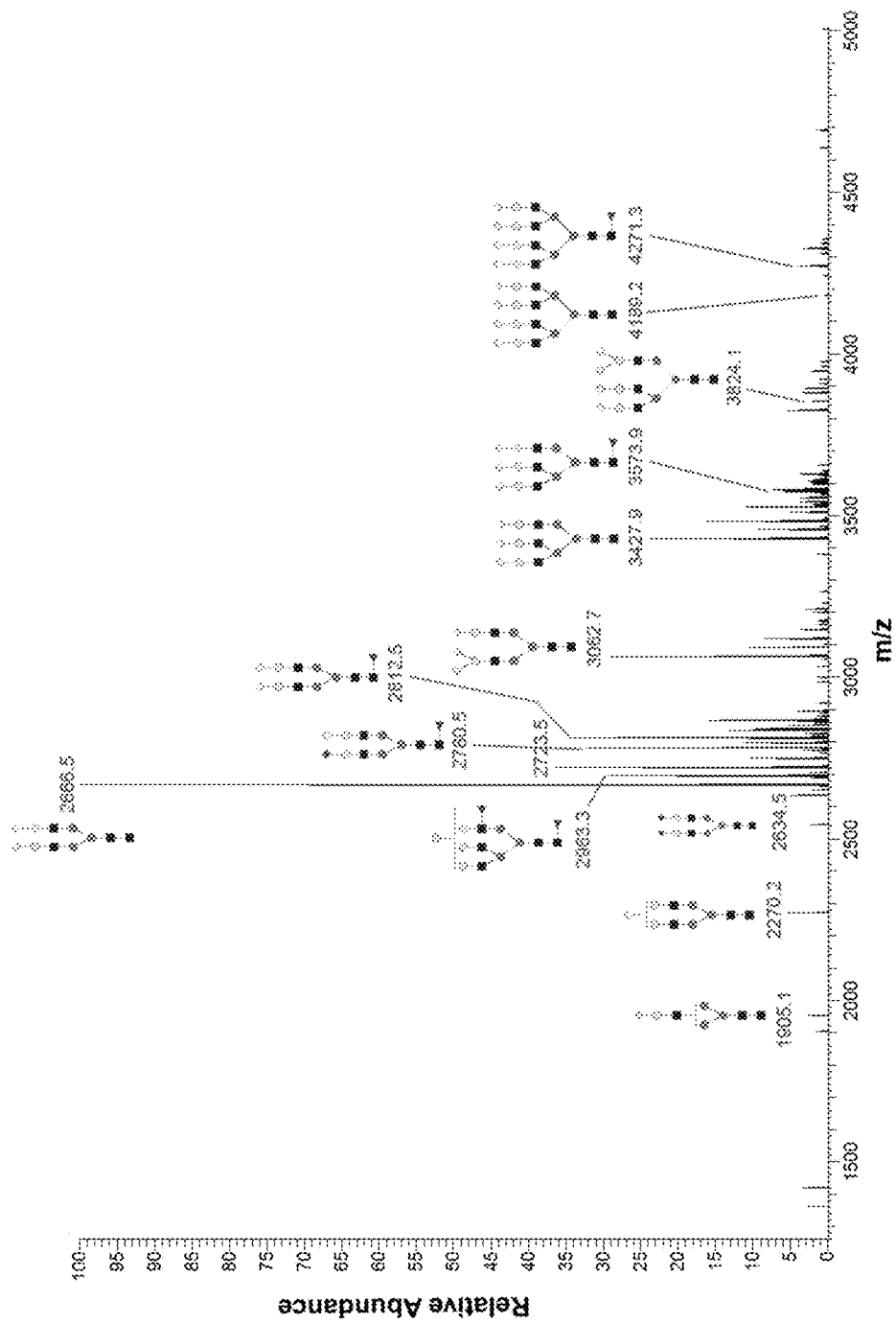
FIG. 16 is a MS of N-glycans from mouse kidney as described in Example 5.
Figure 17:
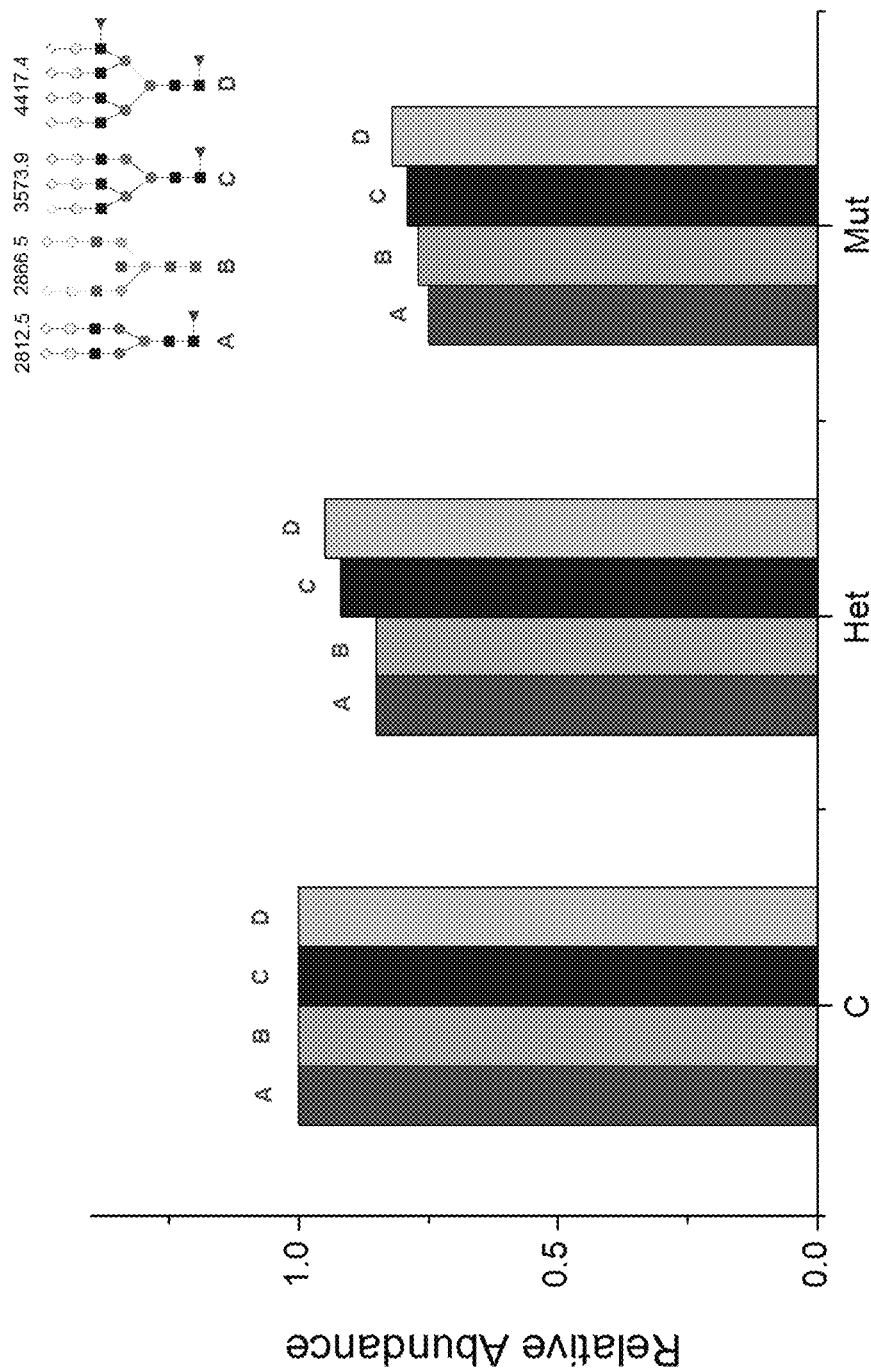
FIG. 17 is a graphical representation of downregulated expression I Het and Mut as described in Example 5.
Figure 18:
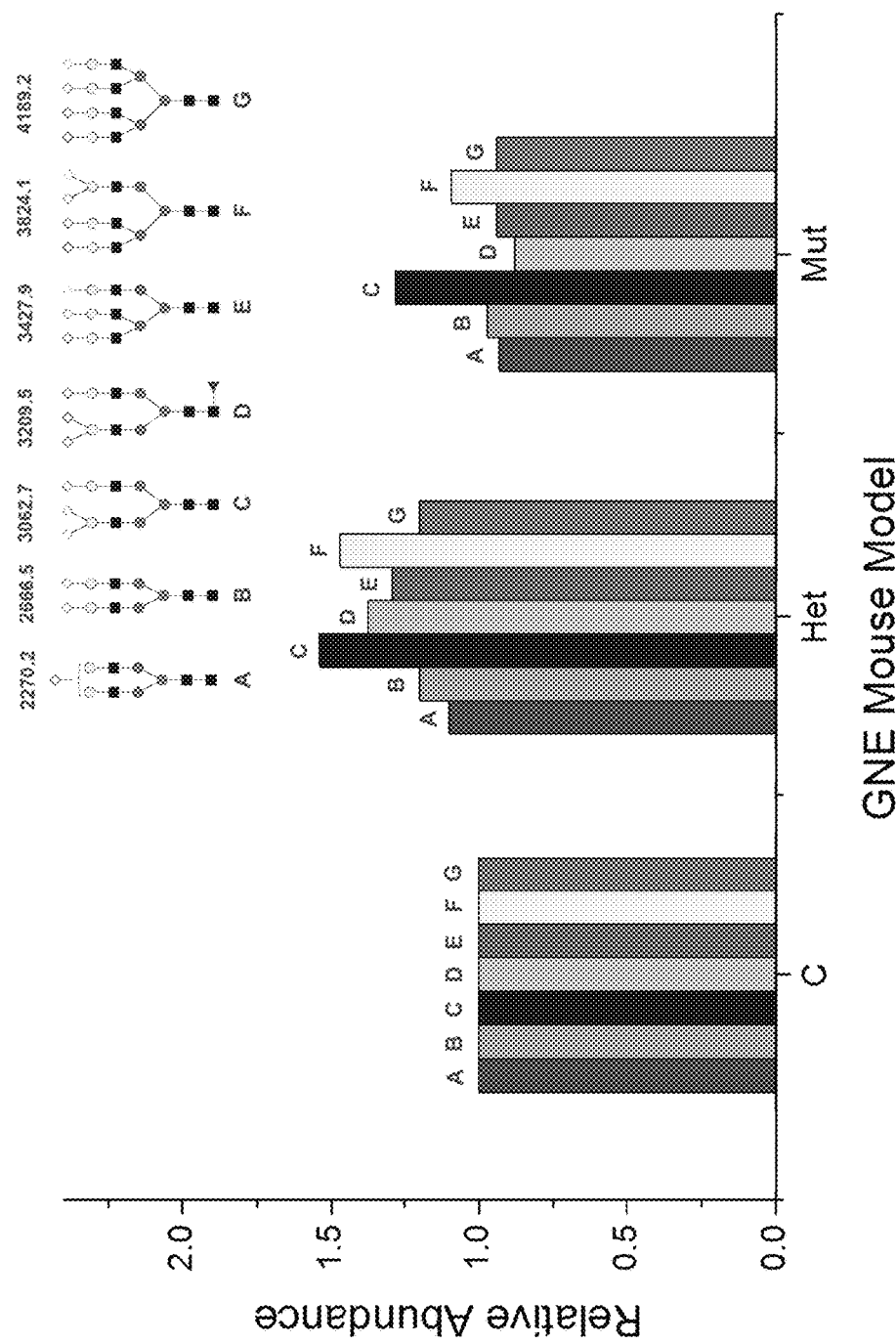
FIG. 18 is a graphical representation of upregulated expression in Het as described in Example 5.

FIG. 16 shows N-glycans from mouse kidney. FIG. 17 shows downregulated expression in Het and Mut. FIG. 18 shows upregulated expression in Het.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the claimed is intended to be broadly construed and interpreted, as including all such variations, modifications and alternative embodiments, within its spirit and scope.

What is claimed is:

1. A quaternary ammonium containing isobaric tag reagent comprising the formula:

reporter group-balancer group-reactive group, wherein the reagent has the structure:

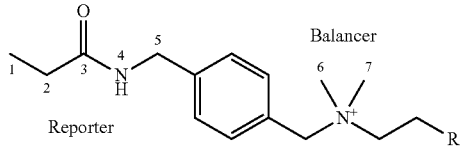

wherein at least one of positions 1-7 comprises a heavy isotope atom, the reporter group and balancer group are linked by an MS/MS scissionable bond, and R is a reactive group capable of conjugating with glycans.

2. The quaternary ammonium containing isobaric tag reagent of claim 1, wherein the reporter group has a mass in a range of from 176 to 179 Da, the reagent contains 2 or 3 heavy isotope atoms independently selected from $^{13}$C and $^{2}$H, and the reactive group R comprises a reactive primary amine capable of conjugating with glycans via reductive amination.

3. The quaternary ammonium containing isobaric tag reagent of claim 2 wherein the quaternary amine containing isobaric tag has the structure (I):

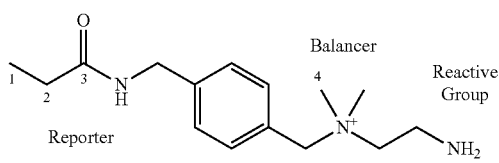

and wherein the methyl group at position 4 is $^{13}$CHD$_2$.

4. The quaternary amine ammonium containing isobaric tag reagent of claim 2 wherein the quaternary amine containing isobaric tag has the structure (I):

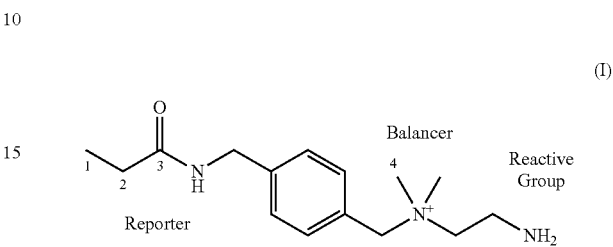

and wherein the methyl group at position 4 is CHD$_2$ and the carbon at position 3 is $^{13}$C.

5. The quaternary ammonium containing isobaric tag reagent of claim 2 wherein the quaternary ammonium containing isobaric tag has the structure (I):

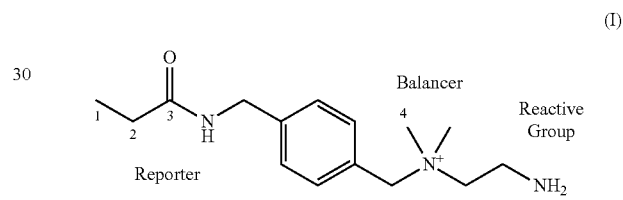

and wherein the carbon at each of positions 1, 2 and 4 is $^{13}$C.

6. The quaternary ammonium containing isobaric tag reagent of claim 1 wherein the quaternary ammonium containing isobaric tag has the structure (I):

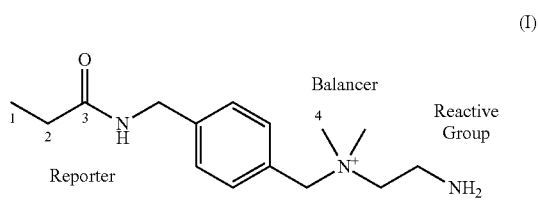 [SMILES: CCC(=O)NCc1ccc(C[N+](C)(C)CCN)cc1]

and wherein the carbon at each of positions 1, 2 and 3 is $^{13}$C.

7. The quaternary ammonium containing isobaric tag reagent of claim 1, wherein the reagent has the structure (A):

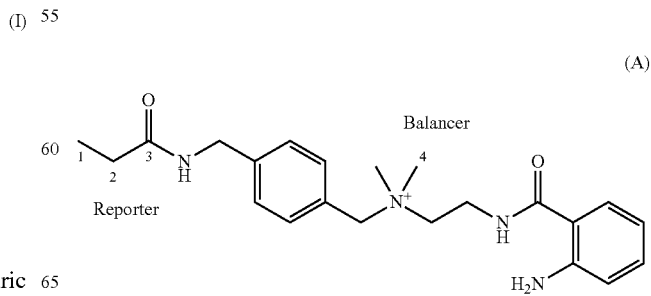

wherein at least one of positions 1-4 of the structure (A) comprises said heavy isotope atom.

8. A method of N-glycan analysis comprising labeling N-glycans with a quaternary ammonium containing isobaric tag reagent comprising the formula:

reporter group-balancer group-reactive group, wherein the reagent has the structure:

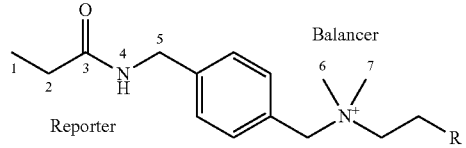

wherein at least one of positions 1-7 comprises a heavy isotope atom, the reporter group and balancer group are linked by an MS/MS scissionable bond, and R is a reactive group capable of conjugating with N-glycans.

9. The method of claim 8, wherein the reporter group has a mass in a range from 176 to 179 Da and the reagent contains 2 or 3 heavy isotope atoms independently selected from $^{13}C$ and $^{2}H$.

10. The method of claim 8, wherein the reactive group comprises a reactive primary amine capable of conjugating with glycans via reductive amination.

11. The method of claim 8, further comprising quantitatively analyzing the labeled N-glycans.

12. The method of claim 11, wherein the quantitatively analyzing step comprises fragmenting the reagent and quantitating the N-glycans.

13. The method of claim 12, wherein fragmenting the reagent comprises MS/MS scission of the MS/MS scissionable bond.

14. The method of claim 11, wherein Na$^+$ is not used in quantitatively analyzing the labeled glycans.

15. The method of claim 8, wherein the N-glycans are obtained by
(a) immobilizing glycoproteins comprising the N-glycans on a solid support;
(b) chemically modifying the N-glycans; and
(c) releasing the N-glycans from the solid support.

16. The method of claim 15, wherein the glycoproteins are obtained from human or nonhuman animal serum.

17. The method of claim 15, wherein the N-glycans carry sialic acids and the chemical modification of the N-glycans comprises carbodiimide coupling of the sialic acids.

18. The method of claim 8, wherein the quaternary ammonium containing isobaric tag reagent comprises the structure (II):

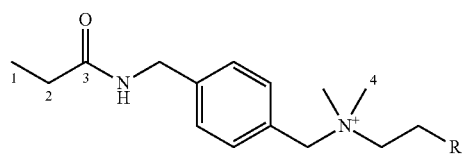

wherein at least one of positions 1-4 of the structure (II) comprises said heavy isotope atom.

19. The method of claim 8, wherein the quaternary ammonium containing isobaric tag reagent has the structure (A):

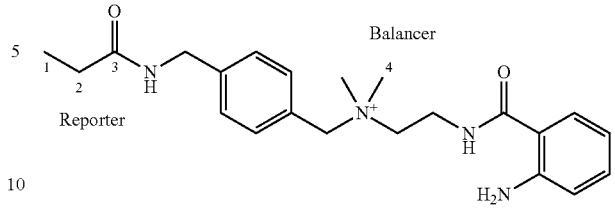

wherein at least one of positions 1-4 of the structure (A) comprises said heavy isotope atom.

20. A method of making a quaternary ammonium-containing isobaric tag reagent comprising the formula:

reporter group-balancer group-reactive group, wherein the reagent has the structure:

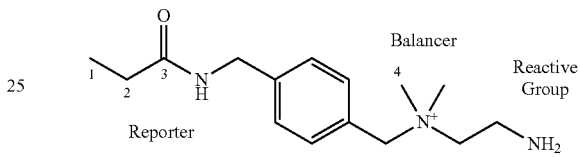

wherein the reporter group and balancer group are linked by an MS/MS scissionable bond, the reporter group has a mass in a range of from 176 to 179 Da, the reagent contains 2 or 3 heavy isotope atoms independently selected from $^{13}C$ and $^{2}H$, and the reactive group comprises a reactive primary amine capable of conjugating with glycans via reductive amination; the method comprising the steps of:
(a) reacting Boc-(4-(aminomethyl)benzyl)-amine and triethylamine with 2-nitrobenzenesulfonyl chloride to obtain a first reaction product;
(b) reacting the first reaction product with sodium carbonate and methyl iodide to obtain a second reaction product;
(c) reacting the second reaction product with β-mercaptoacetic acid to obtain a third reaction product;
(d) reacting the third reaction product with a first intermediate reaction product of a carboxybenzyl-protected 3-amino-1,2-propanediol and sodium periodate to form a fourth reaction product;
(e) removing the tert-butyloxycarbonyl (Boc) protecting group from the fourth reaction product;
(f) reacting the deprotected fourth reaction product with a second intermediate reaction product of propionic acid, 1-ethyl-3-(3-dimethylaminopropyl)carbodiimide and N-hydroxysuccinimide to form a fifth reaction product;
(g) reacting the fifth reaction product with methyl iodide to obtain a crude final product; and
(h) removing the carboxybenzyl (Cbz) protecting group from the crude final product to obtain the quaternary ammonium-containing isobaric tag reagent;
wherein the propionic acid and methyl iodide are selected from one of the following reactant pairs (i)-(iv) comprising heavy isotope labeled reactant:
(i) isotope-unlabeled propionic acid of the formula $CH_3CH_2COOH$, and isotope-labeled methyl iodide of the formula $^{13}CHD_2I$;
(ii) isotope-labeled propionic acid of the formula $CH_3CH_2^{13}COOH$, and isotope-labeled methyl iodide of the formula $CHD_2I$;

(iii) isotope-labeled propionic acid of the formula $^{13}CH_3^{13}CH_2COOH$, and isotope-labeled methyl iodide of the formula $^{13}CH_3I$; and
(iv) isotope-labeled propionic acid of the formula $^{13}CH_3^{13}CH_2^{13}COOH$, and isotope-unlabeled methyl iodide of the formula $CH_3I$.

* * * * *

UNITED STATES PATENT AND TRADEMARK OFFICE
CERTIFICATE OF CORRECTION

PATENT NO. : 10,254,291 B2
APPLICATION NO. : 14/880972
DATED : April 9, 2019
INVENTOR(S) : Shuwei Li et al.

It is certified that error appears in the above-identified patent and that said Letters Patent is hereby corrected as shown below:

In the Specification

In Table 5 at Columns 37-40:
Under Heading "Accession" – first entry "320548" should be -- 520548 --.
Under Heading "Accession" – thirteenth entry "143707063" should be -- 148707063 --.
Under Heading "Accession" – fourteenth entry "143680652" should be -- 148680652 --.
Under Heading "Accession" – fifteenth entry "33991500" should be -- 55991500 --.
Under heading "Gene" – second entry "Ign-2" should be -- Igh-2 --.
Under heading "Gene" – third entry "Anapl_06356" should be -- Anapl_06856 --.
Under heading "Functions" – fourth entry "Kidney membrane enzyme" should be -- Kidney membrane structure --.

In the Claims

Column 39, Line 65, in Claim 4, "quaternary amine ammonium" should be -- quaternary ammonium --.

Signed and Sealed this
Fourteenth Day of May, 2019

Andrei Iancu
*Director of the United States Patent and Trademark Office*